(12) United States Patent
Murakami

(10) Patent No.: US 12,734,298 B2
(45) Date of Patent: Sep. 15, 2026

(54) DRUG CARTRIDGE, DRUG INJECTION DEVICE, AND DRUG INJECTION SYSTEM

(71) Applicant: PHC Holdings Corporation, Tokyo (JP)

(72) Inventor: Kenji Murakami, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 432 days.

(21) Appl. No.: 18/293,556

(22) PCT Filed: Jun. 23, 2022

(86) PCT No.: PCT/JP2022/025109
§ 371 (c)(1),
(2) Date: Jan. 30, 2024

(87) PCT Pub. No.: WO2023/032432
PCT Pub. Date: Mar. 9, 2023

(65) Prior Publication Data
US 2024/0335610 A1 Oct. 10, 2024

(30) Foreign Application Priority Data
Aug. 31, 2021 (JP) ................................ 2021-141849

(51) Int. Cl.
*A61M 5/24* (2006.01)
*A61M 5/20* (2006.01)
*A61M 5/32* (2006.01)

(52) U.S. Cl.
CPC ........ *A61M 5/2429* (2013.01); *A61M 5/3204* (2013.01); *A61M 5/326* (2013.01); *A61M 2005/206* (2013.01)

(58) Field of Classification Search
CPC .............. A61M 5/2429; A61M 5/3204; A61M 5/326; A61M 2005/206; A61M 5/002;
(Continued)

(56) References Cited

U.S. PATENT DOCUMENTS

2014/0330203 A1* 11/2014 McLoughlin ........... A61M 5/20 604/131
2015/0045729 A1 2/2015 Denzer et al.
(Continued)

FOREIGN PATENT DOCUMENTS

JP 2014-516634 7/2014
JP 2016-515406 5/2016
(Continued)

OTHER PUBLICATIONS

International Search Report issued Sep. 6, 2022 in International (PCT) Application No. PCT/JP2022/025109.

*Primary Examiner* — Chelsea E Stinson
*Assistant Examiner* — Eric A Lange
(74) *Attorney, Agent, or Firm* — Wenderoth, Lind & Ponack, L.L.P.

(57) ABSTRACT

A drug cartridge includes a pre-filled syringe, a cassette outer sheath, a cap, a needle guard, a sleeve and a cassette spring, wherein when the cap is fitted into the cassette front opening of the cassette outer sheath, the cap is capable of assuming a locked state where the cap cannot be detached from the cassette outer sheath and an unlocked state where the cap can be detached from the cassette outer sheath.

19 Claims, 45 Drawing Sheets

(58) Field of Classification Search
CPC ........ A61M 5/3243; A61M 2005/3247; A61M 2205/583; A61M 5/24; A61M 5/3202; A61M 5/20; A61M 2005/2073
See application file for complete search history.

(56) References Cited

U.S. PATENT DOCUMENTS

| | | | | |
|---|---|---|---|---|
| 2016/0022914 | A1* | 1/2016 | Mounce | A61M 5/3271 604/189 |
| 2019/0282767 | A1 | 9/2019 | Pedersen et al. | |
| 2020/0254189 | A1* | 8/2020 | Dumet | A61M 5/3202 |
| 2024/0316277 | A1* | 9/2024 | Lemming | A61M 5/2422 |
| 2024/0424223 | A1* | 12/2024 | Spork | A61M 5/2033 |

FOREIGN PATENT DOCUMENTS

| | | | |
|---|---|---|---|
| JP | 2019-519337 | | 7/2019 |
| JP | 2019-208575 | | 12/2019 |
| JP | 2019208575 A | * | 12/2019 |

* cited by examiner 110
130
150
152g
111e
130e 110
130
150
152g
152j
130e 130
12
150

130
140
150

201a
203j
201C
204
203

279
224
225
230
221

279
225
224
224c
230
230c
222a
222e
222d
222b
222c
221
221b
221a
221j 233d
233g
120b
152h
152g
120k
152f
120
152(150)
221
286(230)
100

286(230)
233d
120b
152h
152g
233g
120k
152f
120
152(150)
100
221

286(230)
233d
152h
152g
233g
152f
152(150)
100

268
212
265
279
214
224
221
286

214
268
212
265
279
224
221
286

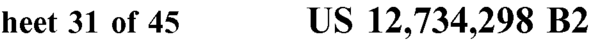
*FIG.24A*
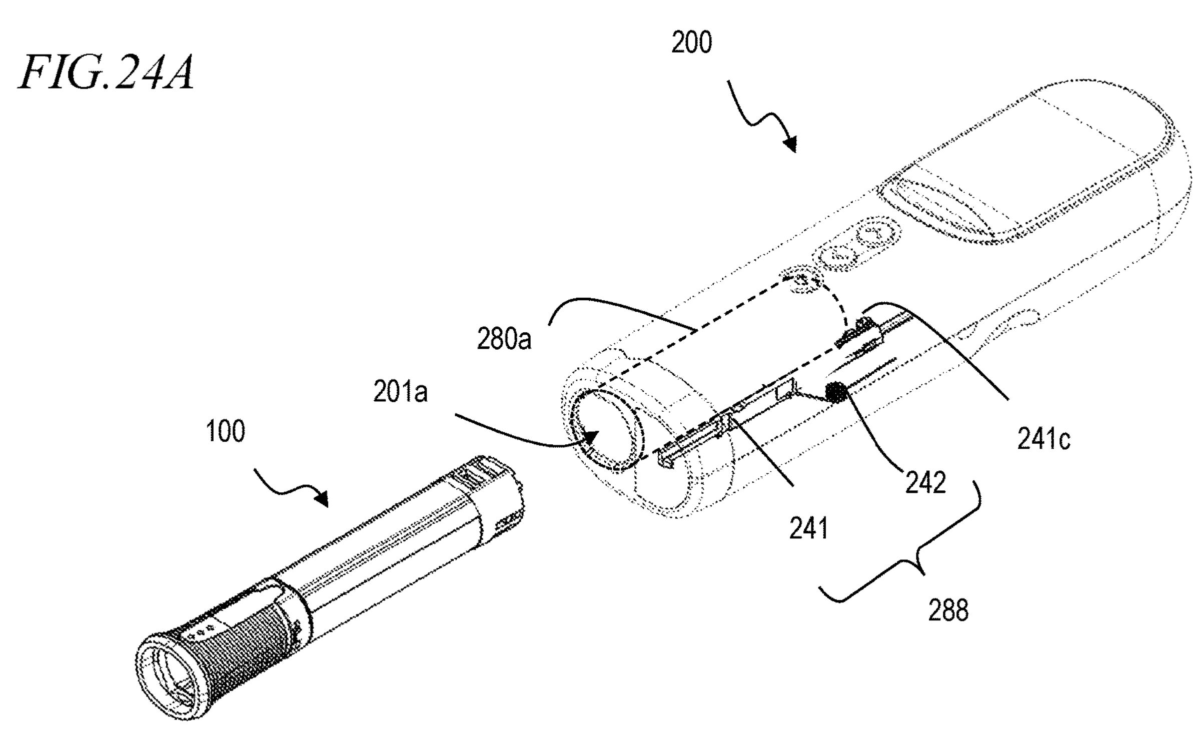
*FIG.24B*
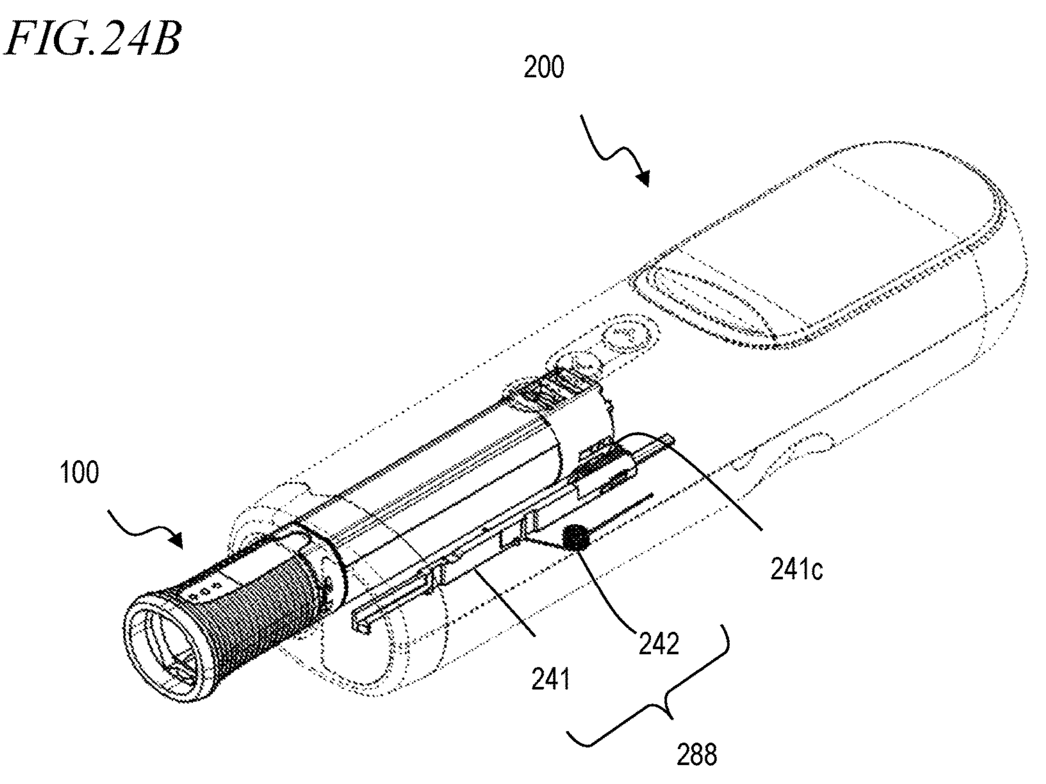

DRUG CARTRIDGE, DRUG INJECTION DEVICE, AND DRUG INJECTION SYSTEM

TECHNICAL FIELD

The present application relates to a drug cartridge, a drug injection device and a drug injection system for injecting a drug.

BACKGROUND ART

Treatment by self-injection, in which a patient injects himself/herself, is becoming popular, and drug injection devices for self-injection have been developed. Pre-filled syringes are known as a type of syringe used for such self-injection. A pre-filled syringe is a syringe that has been pre-filled with a drug and an injection needle may also be attached to the syringe. The use of pre-filled syringes eliminates the need for the patient to fill the drug and attach the injection needle, and allows the drug to be injected while maintaining the cleanliness of the pre-filled syringe at the time of its manufacture. For example, Patent Document No. 1 discloses a drug injection device that uses such a pre-filled syringe.

CITATION LIST

Patent Literature

Patent Document No. 1: Japanese National Phase PCT Laid-open Publication No. 2014-516634

SUMMARY OF INVENTION

Technical Problem

There is a demand for a drug injection device that has better operability and safety. A non-limiting illustrative embodiment of the present application provides a drug injection device and a drug injection system with superior operability and safety, and a drug cartridge for use therewith.

Solution to Problem

A drug cartridge according to one embodiment of the present disclosure includes: a pre-filled syringe including a drug, a syringe barrel having a syringe columnar space in which the drug is arranged and a syringe opening located at one end of the syringe columnar space, an injection needle located on an opposite side of the syringe barrel from the syringe opening and being in communication with the syringe columnar space, a stopper movable in the syringe columnar space and arranged on the syringe opening side, and a needle shield that covers a tip of the injection needle and is removable; a cassette outer sheath including a cassette front opening, a cassette rear opening and a cassette columnar space located between the cassette rear opening and the cassette front opening, wherein the cassette outer sheath holds the pre-filled syringe in the cassette columnar space so that a part of the injection needle and a part of the needle shield protrude from the cassette front opening; a cap mated with the needle shield and fitted into the cassette front opening so as to cover the needle shield, wherein the cap is removable from the cassette outer sheath together with the needle shield; a needle guard including a guard portion and movable in an axis direction of the cassette columnar space in the cassette columnar space, wherein the needle guard is movable between a first engagement position and a second engagement position, wherein in the first engagement position, a front end of the guard portion is further backward than the tip of the injection needle protruding from the cassette front opening, and in the second engagement position, the front end of the guard portion protrudes from the tip of the injection needle protruding from the cassette front opening where the cap is detached; a sleeve movable in the axis direction in the cassette columnar space between a first position located on the cassette rear opening side and a second position located on the cassette front opening side relative to the first position, wherein the sleeve is engaged with the cassette outer sheath in the first position; and a cassette spring that biases the needle guard toward the cassette front opening, wherein when the cap is fitted into the cassette front opening, the cap is capable of assuming a locked state where the cap cannot be detached from the cassette outer sheath and an unlocked state where the cap can be detached from the cassette outer sheath.

A drug injection device according to one embodiment of the present disclosure includes: a case including a cartridge space in which the above-mentioned drug cartridge can be loaded, and a cartridge opening in communication with the cartridge space; a piston unit including a piston, a piston gear that drives the piston in a piston axis direction, and a latch unit for gripping the drug cartridge, wherein a part of the latch unit is inserted into the cassette rear opening of the drug cartridge; a needle insertion/removal motor causing the piston unit to move forward and move backward in the piston axis direction; an injection motor causing the piston to move forward and move backward in the piston axis direction; a control circuit for controlling the needle insertion/removal motor and the injection motor; and an interface for inputting a command to the control circuit.

Advantageous Effects of Invention

According to at least one of the embodiments of the present disclosure, there is provided a drug injection device and a drug injection system with superior operability and safety, and a drug cartridge for use therewith.

BRIEF DESCRIPTION OF DRAWINGS

FIG. 24A is a perspective view illustrating the operation of the slider unit.

FIG. 24B is a perspective view illustrating the operation of the slider unit.

DESCRIPTION OF EMBODIMENTS

Figure 1A:
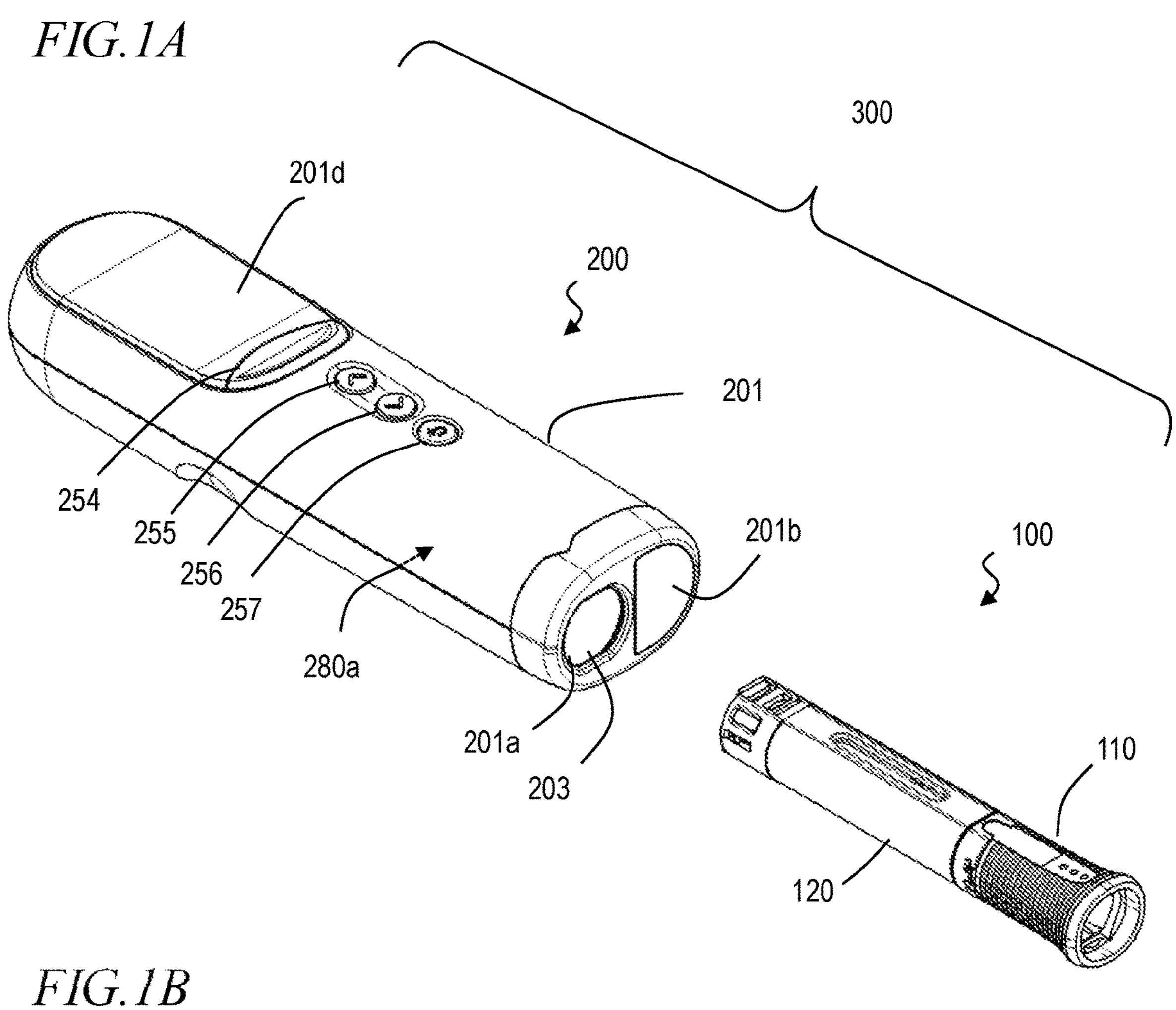
FIG. 1A is a perspective view showing the external appearance of a drug injection system including a drug cartridge and a drug injection device.

It is preferred that a drug injection device used by a patient to inject a drug themselves can be used properly without requiring skill. It is preferred that it is easy to operate and safe. The drug cartridge and the drug injection device of the present disclosure are compatible with a pre-filled syringe with an injection needle attached thereto, and suppress the possibility of the injection needle being exposed from the drug cartridge and the operator accidentally touching the injection needle other than during injection. The drug cartridge, the drug injection device and the drug injection system of the present disclosure will be outlined below.

[Item 1]

A drug cartridge including:

a pre-filled syringe including a drug, a syringe barrel having a syringe columnar space in which the drug is arranged and a syringe opening located at one end of the syringe columnar space, an injection needle located on an opposite side of the syringe barrel from the syringe opening and being in communication with the syringe columnar space, a stopper movable in the syringe columnar space and arranged on the syringe opening side, and a needle shield that covers a tip of the injection needle and is removable;

a cassette outer sheath including a cassette front opening, a cassette rear opening and a cassette columnar space located between the cassette rear opening and the cassette front opening, wherein the cassette outer sheath holds the pre-filled syringe in the cassette columnar space so that a part of the injection needle and a part of the needle shield protrude from the cassette front opening;

a cap mated with the needle shield and fitted into the cassette front opening so as to cover the needle shield, wherein the cap is removable from the cassette outer sheath together with the needle shield;

a needle guard including a guard portion and movable in an axis direction of the cassette columnar space in the cassette columnar space, wherein the needle guard is movable between a first engagement position and a second engagement position, wherein in the first engagement position, a front end of the guard portion is further backward than the tip of the injection needle protruding from the cassette front opening, and in the second engagement position, the front end of the guard portion protrudes from the tip of the injection needle protruding from the cassette front opening where the cap is detached;

a sleeve movable in the axis direction in the cassette columnar space between a first position located on the cassette rear opening side and a second position located on the cassette front opening side relative to the first position, wherein the sleeve is engaged with the cassette outer sheath in the first position; and a cassette spring that biases the needle guard toward the cassette front opening, wherein when the cap is fitted into the cassette front opening, the cap is capable of assuming a locked state where the cap cannot be detached from the cassette outer sheath and an unlocked state where the cap can be detached from the cassette outer sheath.

[Item 2]

The drug cartridge according to item 1, wherein:

where the cap is fitted into the cassette front opening; and the needle guard is in contact with the cap and is located in the first engagement position against a biasing force of the cassette spring.

[Item 3]

The drug cartridge according to item 2, wherein:

where the cap is fitted into the cassette front opening and the sleeve is in the first position, the cap is locked; and where the cap is fitted into the cassette front opening and the sleeve is in the second position, the sleeve renders the cap in an unlocked state and the needle guard in a locked state in which the needle guard is unmovable in the first engagement position.

[Item 4]

The drug cartridge according to item 3, wherein:

one end of the cassette spring is in contact with the needle guard and the other end of the cassette spring is in contact with the sleeve; and where the cap is fitted into the cassette front opening, the sleeve moves from the first position to the second position by an external force against the biasing force of the cassette spring, thereby removing the cap.

[Item 5]

The drug cartridge according to item 4, wherein:

after the cap is removed, the external force is removed so that the sleeve moves from the second position to the first position by the biasing force of the cassette spring; and as the sleeve unlocks the needle guard, the needle guard moves from the first engagement position to the second engagement position by the biasing force of the cassette spring.

[Item 6]

The drug cartridge according to item 5, wherein in the second engagement position, the needle guard is engaged with the cassette outer sheath so that the needle guard is unmovable toward the first engagement position.

[Item 7]

The drug cartridge according to item 1, wherein in the first position, the sleeve is engaged with the cassette outer sheath so that the sleeve is unmovable toward the second position.

[Item 8]

The drug cartridge according to item 1, wherein:

the syringe barrel includes a flange arranged in the vicinity of the syringe opening;

the cassette outer sheath includes a slit located in the vicinity of the cassette rear opening; and as the flange of the syringe barrel is inserted into the slit of the cassette outer sheath, the pre-filled syringe is held in the cassette outer sheath.

[Item 9]

The drug cartridge according to item 1, wherein:

the cap includes a cap main body and a cap spring that mates with the needle shield, wherein the cap main body includes a cylindrical trunk portion, a first elastic support portion one end of which is located at one end of the trunk portion, and a first engagement claw located at the other end of the first elastic support portion and including a contact surface at a tip thereof, wherein the cap spring is arranged in the trunk portion;

the cassette outer sheath includes a cap engagement portion located on an inner surface on a side of the cassette front opening; and where the cap is fitted into the cassette front opening, the cap main body surrounds the cassette front opening, the first engagement claw is inserted into the cassette outer sheath through the cassette front opening, and the cap is engaged with the cap engagement portion so that the cap is undetachable from the cassette front opening.

[Item 10]

The drug cartridge according to item 9, wherein:

the guard portion of the needle guard includes an end face portion and a needle guard opening provided at the end face portion, and has a cylindrical shape that defines a needle guard columnar space capable of housing a part of the syringe barrel of the pre-filled syringe;

the needle guard further includes a second elastic support portion one end of which is connected to one end of the guard portion opposite from the needle guard opening, and a protrusion provided at the other end of the second elastic support portion;

the cassette outer sheath includes a first opening located on the cassette rear opening side, and a second opening located on the cassette front opening side relative to the first opening;

where the needle guard is in the first engagement position, the protrusion is engaged with the first opening; and where the needle guard is in the second engagement position, the protrusion is engaged with the second opening.

[Item 11]

The drug cartridge according to item 10, wherein:

the protrusion includes a slope portion located on the guard portion side and sloped on the cassette outer sheath side, a recess provided in the slope portion, an apex portion adjacent to the slope portion, a side portion adjacent to the apex portion on an opposite side from the slope portion, and an inner surface portion located on an inner side relative to the slope portion, the apex portion and the side portion;

the cassette outer sheath includes an in-opening protrusion protruding from an edge of the second opening on the cassette front opening side toward a center of the second opening; and where the protrusion is engaged with the second opening, the slope portion of the protrusion is in contact with an edge of the second opening on the cassette front opening side, and the in-opening protrusion is engaged with the recess of the slope portion.

[Item 12]

The drug cartridge according to item 11, wherein:

the sleeve includes an inner cylinder portion including a sleeve front opening and a space that houses a part of the pre-filled syringe, an outer cylinder portion arranged separated outward relative to the inner cylinder portion and including a sleeve rear opening, a sleeve contact surface located on the sleeve front opening side of the outer cylinder portion, and a slit provided in each of the inner cylinder portion and the outer cylinder portion; and in the cassette columnar space of the cassette outer sheath, the sleeve contact surface is located on the cassette front opening side, at least the protrusion and the second elastic support portion of the needle guard are located between the inner cylinder portion and the outer cylinder portion, and the slit of the inner cylinder portion and the slit of the outer cylinder portion are aligned in the radial direction with the second elastic support portion and the protrusion on a cross section perpendicular to an axis of the cassette columnar space.

[Item 13]

The drug cartridge according to item 12, wherein:

where the cap is fitted into the cassette front opening and the sleeve is in the second position, the sleeve contact surface of the sleeve is in contact with a contact surface of the first engagement claw of the cap;

engagement between the first engagement claw and a cap engagement portion of the cassette outer sheath is disengaged by deformation of the first elastic support portion; and the inner cylinder portion of the sleeve and an inner surface of the protrusion of the needle guard are in contact with each other, thereby suppressing deformation of the second elastic support portion.

[Item 14]

The drug cartridge according to item 12, wherein:

where the cap is removed from the cassette front opening and the sleeve is in the first position, an edge of the first opening and the slope portion of the protrusion are in contact with each other by the biasing force of the cassette spring, and the second elastic support portion deforms inward into the slit of the inner cylinder portion, thereby causing the protrusion to detach inward from the first opening, and the needle guard to move from the first engagement position to the second engagement position; and in the second engagement position, the inner cylinder portion of the sleeve and the inner surface of the protrusion of the needle guard are in contact with each other, thereby suppressing deformation of the second elastic support portion.

[Item 15]

The drug cartridge according to item 14, wherein:

the sleeve includes a third elastic support portion one end of which is located in the vicinity of the sleeve rear opening, and a second engagement claw located at the other end of the third elastic support portion and including a contact surface at a tip thereof;

the cassette outer sheath includes a sleeve engagement portion located on an inner surface on the cassette rear opening side; and where the sleeve is in the first position, the second engagement claw of the sleeve and the sleeve engagement portion of the cassette outer sheath are engaged with each other, thereby suppressing the sleeve from moving to the second position.

[Item 16]

A training drug cartridge including:

a cassette outer sheath including a cassette rear opening, a cassette front opening and a cassette columnar space located between the cassette rear opening and the cassette front opening;

a cap fitted into the cassette front opening;

a needle guard including a guard portion and movable in an axis direction of the cassette columnar space in the cassette columnar space, wherein the needle guard is movable between a first engagement position located on the cassette rear opening side and a second engagement position in which a front end of the guard portion protrudes from the cassette front opening where the cap is detached;

a sleeve movable in the axis direction between a first position located on the cassette rear opening side and a second position located on the cassette front opening side relative to the first position, between a pre-filled syringe and the cassette outer sheath in the cassette columnar space; and a cassette spring that biases the needle guard so as to protrude from the cassette front opening, wherein when the cap is fitted into the cassette front opening, the cap is capable of assuming a locked state where the cap cannot be detached from the cassette outer sheath and an unlocked state where the cap can be detached.

[Item 17]

A drug injection device including:

a case including a cartridge space in which the drug cartridge according to any one of items 1 to 15 can be loaded, and a cartridge opening in communication with the cartridge space;

a piston unit including a piston, a piston gear that drives the piston in a piston axis direction, and a latch unit for gripping the drug cartridge, wherein a part of the latch unit is inserted into the cassette rear opening of the drug cartridge;

a needle insertion/removal motor causing the piston unit to move forward and move backward in the piston axis direction;

an injection motor causing the piston to move forward and move backward in the piston axis direction;

a control circuit for controlling the needle insertion/removal motor and the injection motor; and an interface for inputting a command to the control circuit.

[Item 18]

The drug injection device according to item 17, wherein:

the latch unit includes a cartridge latch to engage with the cassette outer sheath of the drug cartridge, and a sleeve contact portion to be in contact with the sleeve of the drug cartridge;

when the drug cartridge is inserted into the cartridge space through the cartridge opening, the sleeve contact portion of the latch unit enters inside through the cassette rear opening to be in contact with the sleeve of the drug cartridge, thereby disengaging the engagement between the sleeve and the cassette outer sheath;

in response to the insertion of the drug cartridge, the sleeve contact portion moves the sleeve toward the second position relative to the cassette outer sheath, and the cartridge latch enters inside through the cassette rear opening; and at completion of loading of the drug cartridge, the sleeve reaches the second position, and the cartridge latch engages with the cassette outer sheath.

[Item 19]

The drug injection device according to item 18, wherein:

based on an input from the interface, the control circuit is configured to:

rotate the needle insertion/removal motor and cause the piston unit to move forward, thereby performing needle insertion;

rotate the injection motor and cause the piston to move forward from an initial position, thereby moving the stopper and injecting the drug; and after rotating the injection motor by a predetermined amount, reversing the needle insertion/removal motor and cause the piston unit to move backward, thereby performing needle removal.

[Item 20]

The drug injection device according to item 19, further including:

a needle guard detector that detects ejection of the needle guard, wherein:

after the needle removal, the control circuit reverses the injection motor to cause the piston to move backward to a needle guard ejection position, which is further backward than the initial position;

in response the piston moving backward, the latch unit rotates around the piston axis, thereby disengaging the contact between the sleeve contact portion and the sleeve;

as the sleeve moves from the second position to the first position by the biasing force of the cassette spring to unlock the needle guard, the needle guard moves from the first engagement position to the second engagement position by the biasing force of the cassette spring; and the needle guard detector detects ejection of the needle guard.

[Item 21]

The drug injection device according to item 20, wherein the needle guard detector includes a light-emitting element that irradiates light onto a part of the needle guard, and a light-receiving element that detects light emitted from the light-emitting element and reflected by the needle guard or transmitted through the needle guard.

[Item 22]

The drug injection device according to item 21, wherein:

the control circuit reverses the injection motor based on a detection signal of the needle guard detector to cause the piston to move backward to a cartridge ejection position, which is further backward than the needle guard ejection position; and in response to the piston moving backward, the latch unit rotates around the piston axis, thereby disengaging the engagement of the cartridge latch with the cassette outer sheath.

[Item 23]

The drug injection device according to any one of items 20 to 22, wherein:

the piston includes a helical contact surface located on the tip side;

the latch unit includes a through hole into which the piston is inserted, and a restricting portion located on an inner surface of the through hole; and as the contact surface of the piston and the restricting portion of the latch unit come into contact with each other, the piston moves forward and backward, thereby rotating the latch unit around the piston axis.

[Item 24]

The drug injection device according to any one of items 17 to 23, further including a door capable of opening and closing to cover the cartridge opening.

[Item 25]

A drug injection system including:

the drug cartridge according to any one of items 1 to 15; and the drug injection device according to any one of items 17 to 24.

One example of the drug cartridge, the drug injection device and the drug injection system of the present embodiment will now be described in detail with reference to the drawings. The drug injection system, etc., described below are one example of the embodiment. The embodiment is not limited to the following, and various modifications are possible. In the drawings to be referred to in the following description, for the sake of clarity, reference signs in the drawings not mentioned in the description may be omitted.

(Configuration of Drug Injection System)

[Outline of Drug Injection System]

FIG. 1A is a perspective view showing the external appearance of a drug injection system 300 including a drug cartridge 100 and a drug injection device 200. Each of FIG. 1B to FIG. 18 is a perspective view showing the drug injection system 300 in one state during use.

The drug cartridge 100 includes a cap 110 and a cassette outer sheath 120, further including a pre-filled syringe 10 (FIG. 2) inside the cassette outer sheath 120 (FIG. 1A does not show the pre-filled syringe 10 held within the cassette outer sheath 120). As described in more detail below, the pre-filled syringe 10 is filled with a drug and an injection needle 12 is attached. The cap 110 covers the injection needle 12 of the pre-filled syringe 10 being held. Note however that the cap 110 is locked and is configured in such a way that it is difficult to remove the cap 110 even if the operator attempts to remove it by hand.

The drug injection device 200 includes an outer case 201. For example, the outer case 201 has a cylindrical shape having a thickness that is easy for the operator to grip by one hand. In the present embodiment, the outer case 201 has a cylindrical shape composed of two generally flat surfaces and curved surfaces connecting together the two flat surfaces. However, the shape of the outer case 201 is not limited to this and may be cylindrical or square cylindrical, etc.

A cartridge opening 201*a* is provided at one end face of the cylindrical shape of the outer case 201. The cartridge opening 201*a* is in communication with a cartridge space 280*a*, which is located within the outer case 201 and in which the drug cartridge 100 can be loaded. The cartridge opening 201*a* is provided with a door 203 that opens toward the inside of the cartridge space 280*a*.

A skin contact surface 201*b* is further provided at the end face of the outer case 201 on which the cartridge opening 201*a* is provided. A display window 201*d*, an injection button 254, a select (up) button 255, a select (down) button 256 and a back button 257 are arranged on the outer case 201.

In order to use the drug injection system 300, a door 203 is pressed at the rear end of the drug cartridge 100, and the drug cartridge 100 is inserted into the cartridge space 280*a* inside the drug injection device 200 via the cartridge opening 201*a*.

Figure 1B:
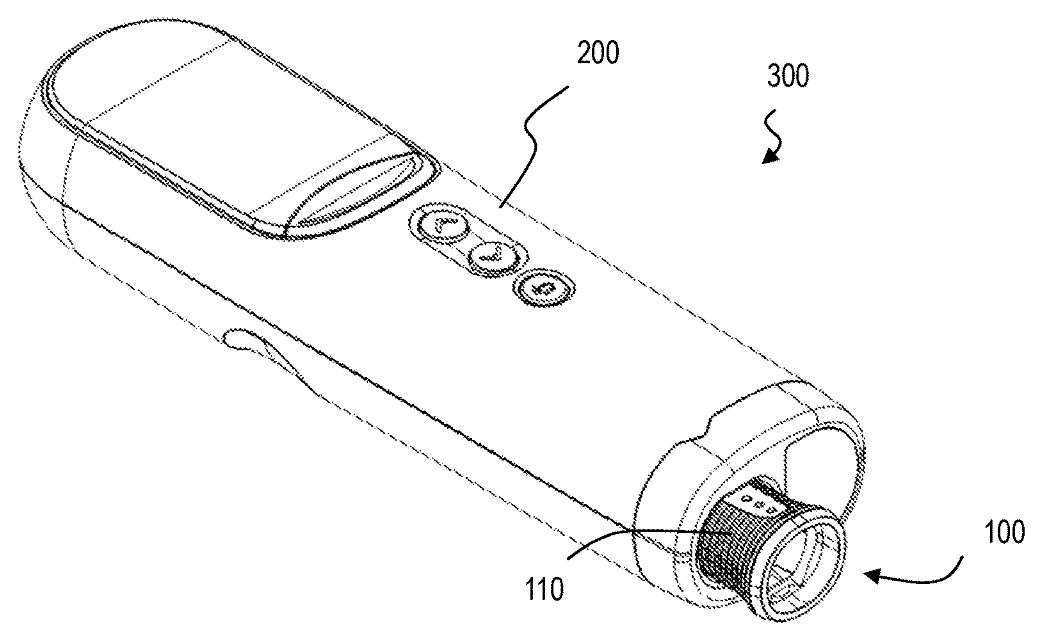
FIG. 1B is a perspective view showing the drug injection system in one state during use.
Figure 1C:
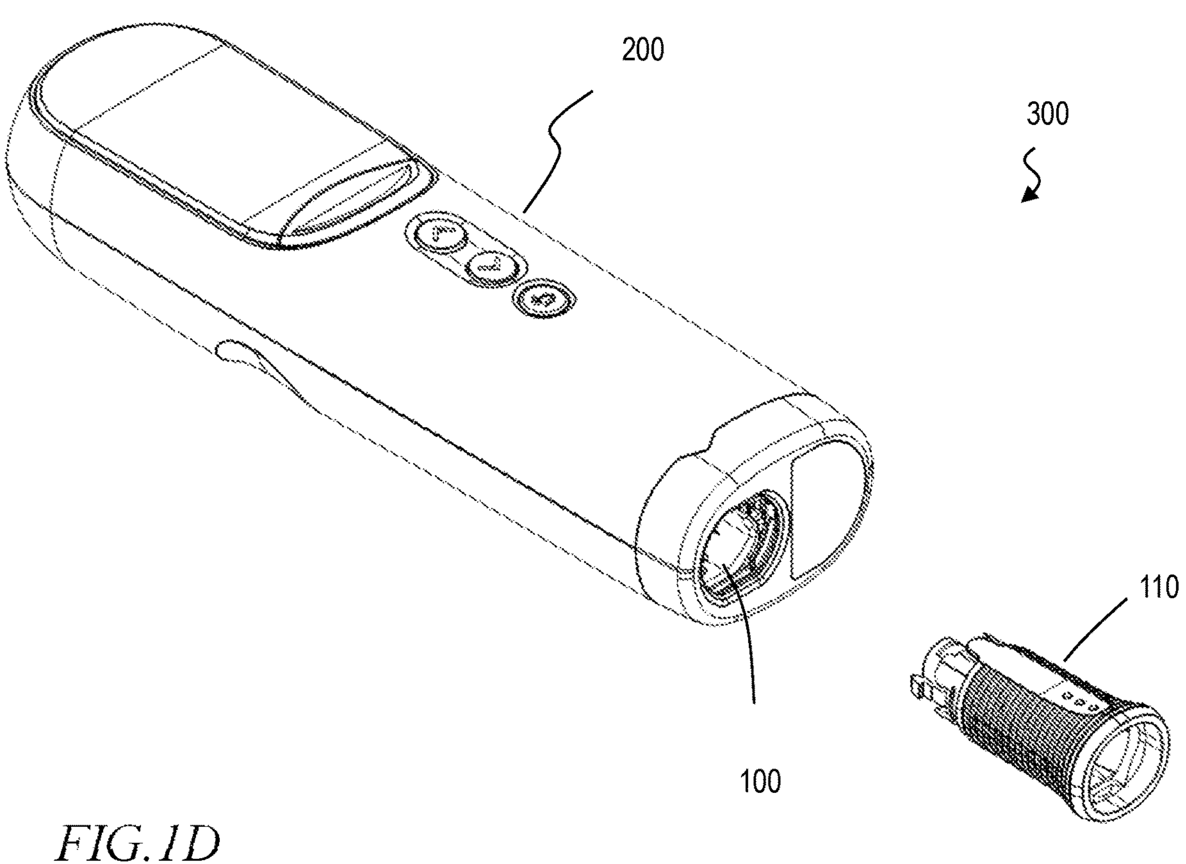
FIG. 1C is a perspective view showing the drug injection system in one state during use.

As shown in FIG. 1B, with loading of the drug cartridge 100 into the drug injection device 200 complete, a portion of the cap 110 is exposed from the outer case 201. When loading of the drug cartridge 100 is complete, the cap 110 is unlocked. This allows the cap 110 to be removed, as shown in FIG. 1C. At this point, the injection needle 12 of the pre-filled syringe 10 is located on the inner side of the outer case 201 relative to the cartridge opening 201*a*. Therefore, with normal handling, the injection needle is suppressed from coming into contact with a part of the body, such as a finger.

Figure 1D:
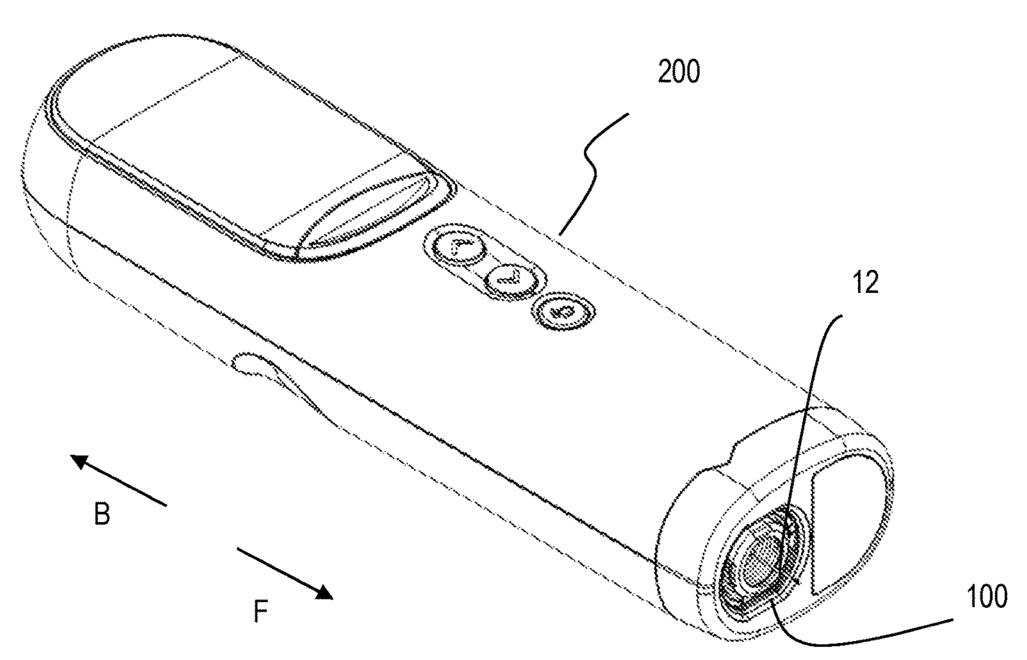
FIG. 1D is a perspective view showing the drug injection system in one state during use.

When the operator presses the tip of the drug injection device 200 against the injection site on the body and depresses the injection button 254, the drug cartridge 100 including the pre-filled syringe 10 moves forward and the injection needle 12 is inserted into the body, as shown in FIG. 1D. In the present specification, the movement of the components, etc., of the drug cartridge 100 and the drug injection device 200 in the direction F of sticking the injection needle 12 into the injection site is referred to as moving forward, and the movement in the direction B of removing the needle as moving backward. When the components of the drug cartridge 100 and the drug injection device 200 have a shape having a length along the direction F and the direction B, the side of each component closer to the injection needle 12 may be referred to as "front" and the side of each component away from the injection needle 12 as "rear". Instead of "before" and "after," they may be referred to as "first" and "second", or "second" and "first".

Figure 1E:
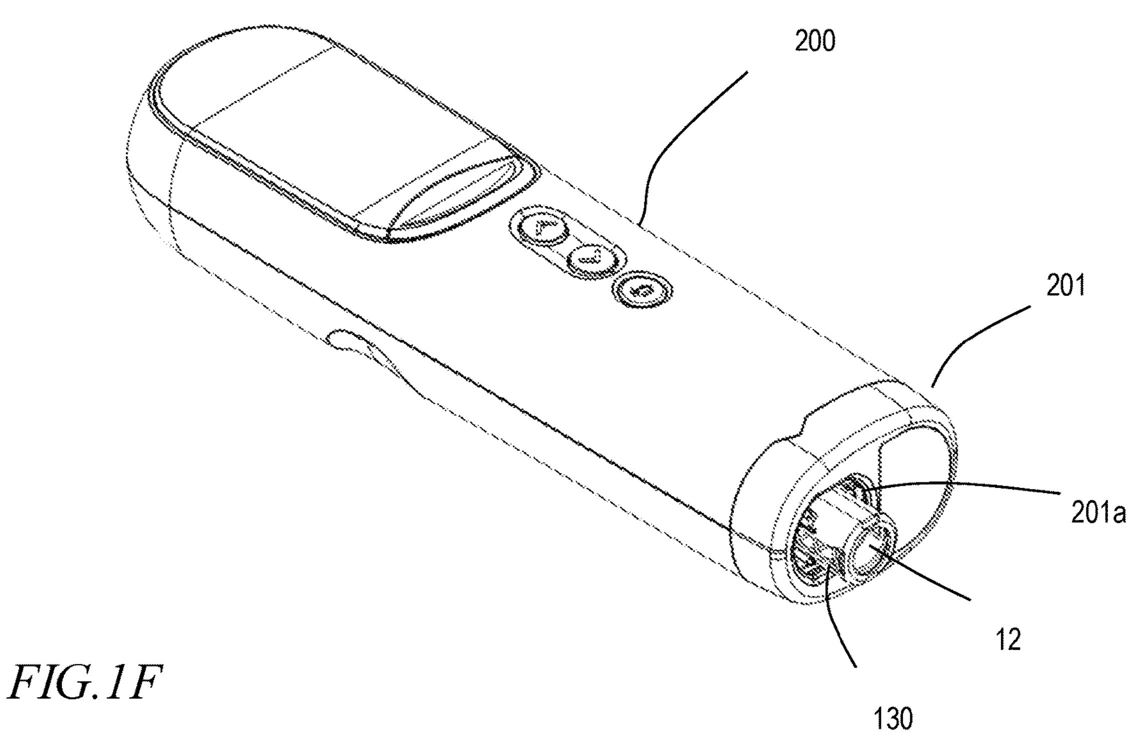
FIG. 1E is a perspective view showing the drug injection system in one state during use.
Figure 1F:
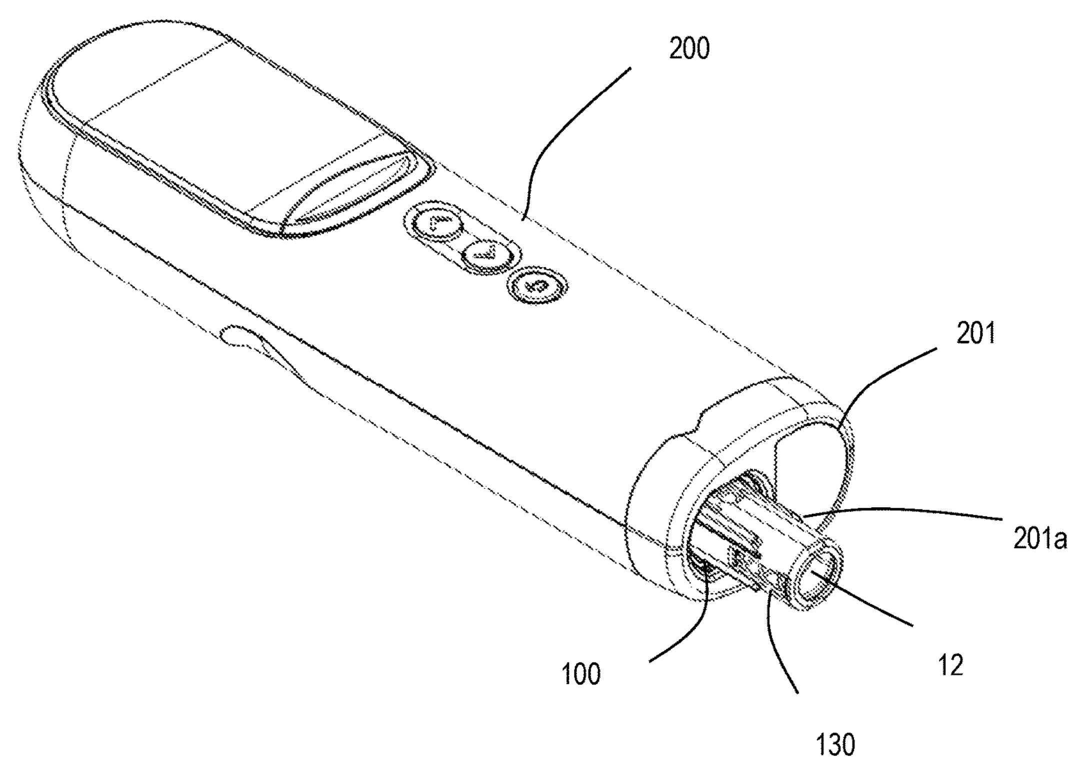
FIG. 1F is a perspective view showing the drug injection system in one state during use.

When drug administration is complete, the drug cartridge 100 moves backward and the injection needle 12 is housed in the outer case 201. When the drug injection device 200 is detached from the injection site, as shown in FIG. 1E, a needle guard 130 of the drug cartridge 100 moves forward to cover the injection needle 12 with a portion thereof protruding from the cartridge opening 201*a*. Then, the drug cartridge 100 is de-coupled from the drug injection device 200, and the drug cartridge 100 further protrudes slightly from the cartridge opening 201*a* as shown in FIG. 1F.

Figures 1G, 1H:
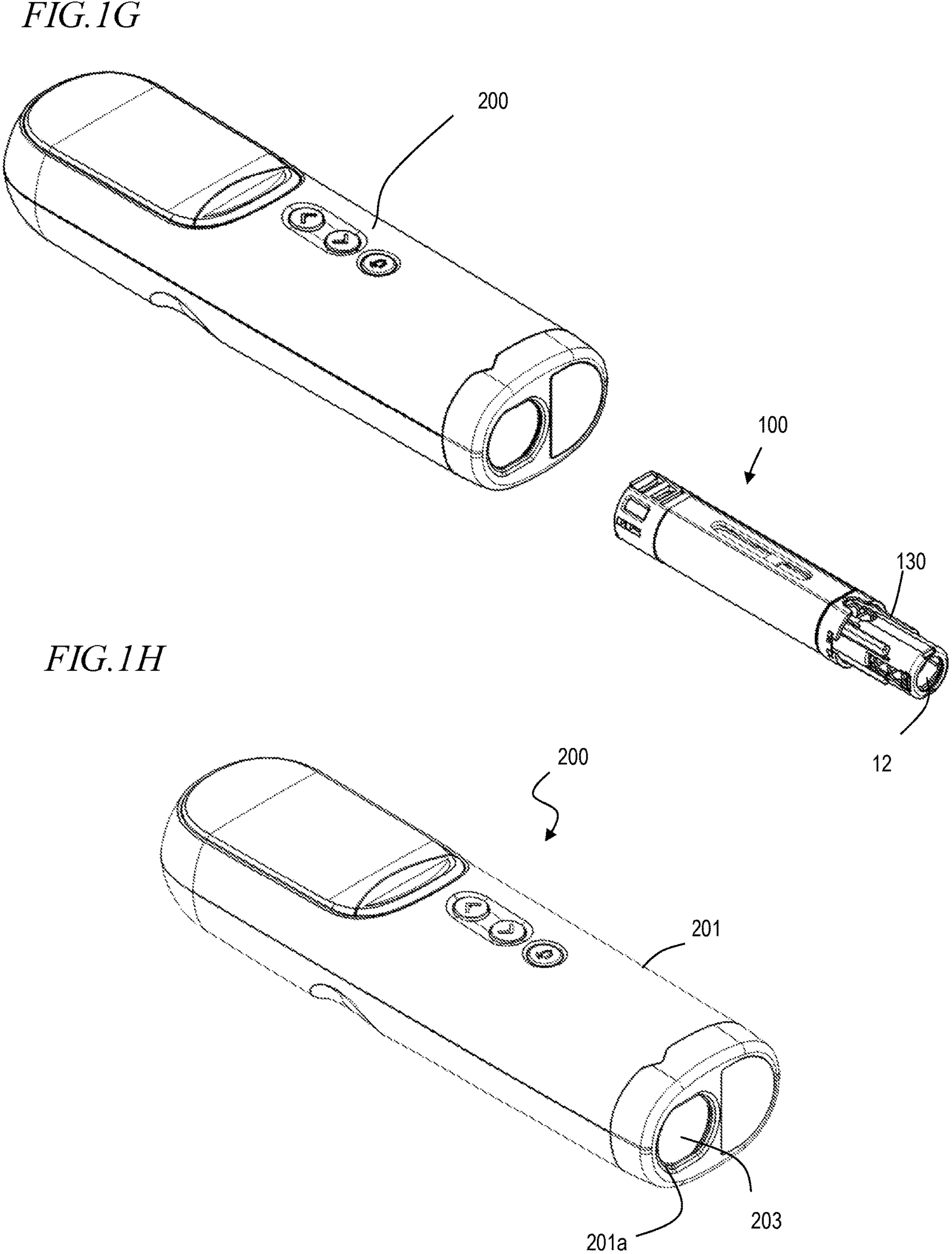
FIG. 1G is a perspective view showing the drug injection system in one state during use.
FIG. 1H is a perspective view showing the drug injection system in one state during use.

The operator picks the needle guard 130 of the drug cartridge 100 and removes the drug cartridge 100 from the drug injection device 200. At this point, as shown in FIG. 1G, the injection needle 12 of the drug cartridge 100 is covered by the needle guard 130. Therefore, the injection needle 12 is suppressed from coming into contact with a part of the body, such as a finger. Then, the door 203 closes the cartridge opening 201*a*, as shown in FIG. 18.

Thus, with the drug injection system 300, the operator can load the drug cartridge 100 into the drug injection system 300 and remove the used drug cartridge 100 without touching the injection needle 12 with no special attention. Since the pre-filled syringe 10 is filled with the drug and the injection needle is attached, injection can be done in a clean (sterile) state at the time of manufacture. The structure of the drug cartridge 100 and the drug injection device 200 will now be described in detail.

[Structure of Pre-Filled Syringe 10 and Drug Cartridge 100]

<Pre-Filled Syringe 10>

Figures 2, 3:
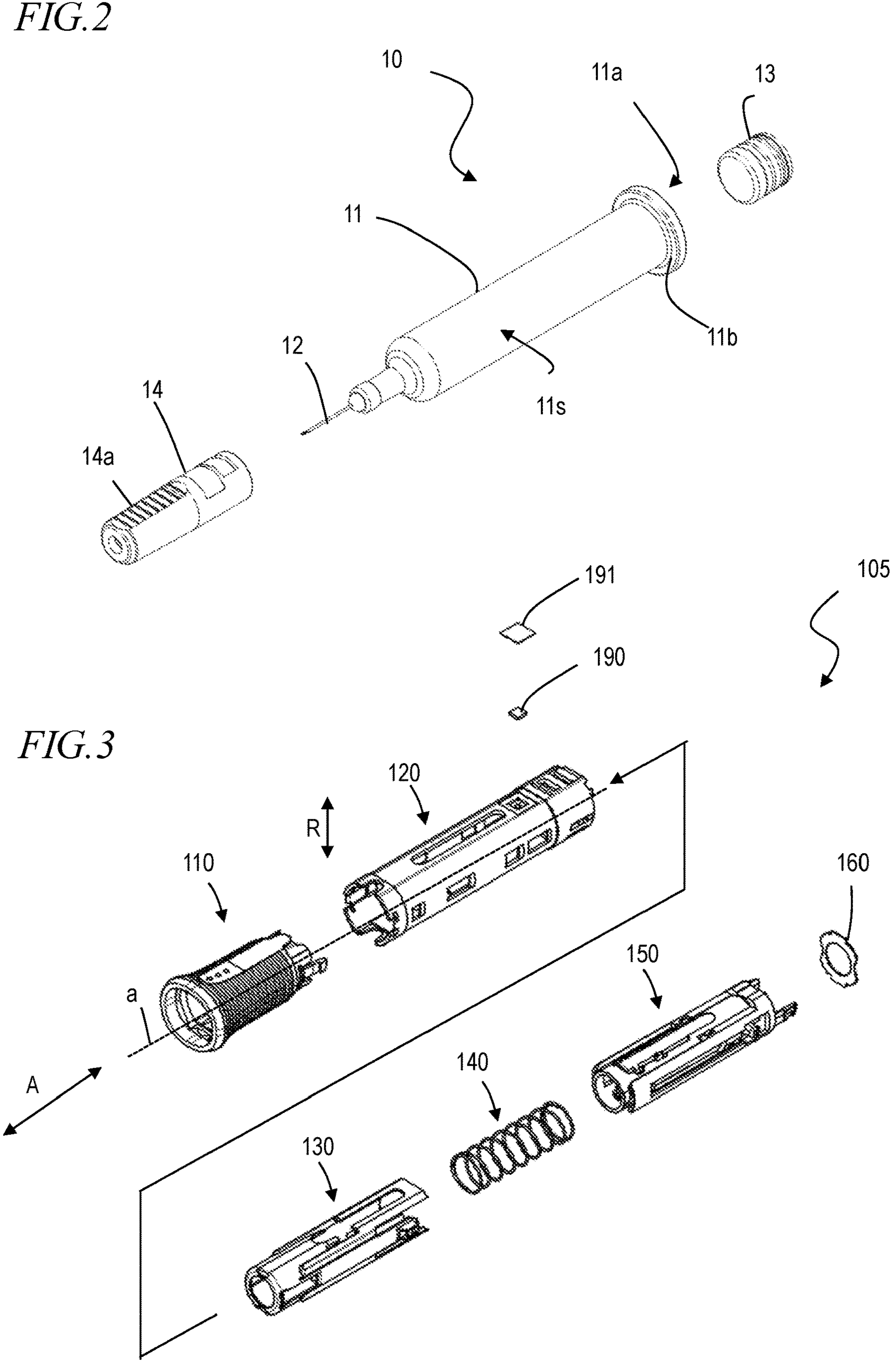
FIG. 2 is an exploded perspective view of a pre-filled syringe.
FIG. 3 is an exploded perspective view of a drug cartridge (excluding the pre-filled syringe).

FIG. 2 is an exploded perspective view of the pre-filled syringe 10. The pre-filled syringe 10 includes a syringe barrel 11, the injection needle 12, a stopper 13 and a needle shield 14. The syringe barrel 11 includes a syringe columnar space 11*s* and a syringe opening 11*a* located at one end of the syringe columnar space 11*s*, and the syringe columnar space 11*s* is filled with the drug. The injection needle 12 is located on the opposite side of the syringe barrel 11 from the syringe opening 11*a*, and is in communication with the syringe columnar space 11*s*. The syringe barrel 11 has a flange 11*b* provided on the syringe opening 11*a* side. The stopper 13 is arranged on the syringe opening 11*a* side of the syringe columnar space 11*s*. The stopper 13 is movable along the axis of the columnar shape within the columnar space of the syringe barrel 11, and when the piston 221 of the drug injection device 200 described below pushes the stopper 13, the drug is released from the tip of the injection needle 12.

The injection needle 12 of the pre-filled syringe 10 is covered by the needle shield 14 to protect the injection needle 12, maintain sterility, and prevent the operator from accidentally sticking the injection needle 12. The outer surface of the needle shield 14 is provided with an engagement portion 14*a*. The engagement portion 14*a* is, for example, an uneven surface provided on the outer surface of the needle shield 14. The needle shield 14 is inserted into the hole in the cap 110 of the drug cartridge 100 to be described below, and is removed from the pre-filled syringe 10 together with the cap 110. The engagement portion 14*a* engages the needle shield 14 with the cap 110 so that the needle shield 14 is removed from the pre-filled syringe 10 together with the cap 110 during this removal. The engagement portion 14*a* is not limited to the form shown in FIG. 2 and may have other forms. The engagement portion 14*a* may be a rough surface that contacts the inner surface of the hole in the cap 110 with great friction. Alternatively, the needle shield 14 may be frictionally coupled to the cap 110 when the needle shield 14 is press-fitted into the hole in the cap 110 by having an outer diameter slightly larger than the hole in the cap 110 without the engagement portion 14*a*.

There may be one or more types of drugs to be filled in the pre-filled syringe 10. There may also be one or more variations in the amount of drug. In other words, even pre-filled syringes 10 having the same shape may have different types and/or amounts of drug filled therein.

<Drug Cartridge 100>

FIG. 3 is an exploded perspective view of the drug cartridge 100 with the pre-filled syringe 10 removed. The drug cartridge 100 with the pre-filled syringe 10 removed is referred to also as a cassette 105.

The drug cartridge 100 includes the cap 110, the cassette outer sheath 120, the needle guard 130, a cassette spring 140, a sleeve 150 and a syringe retaining sheet 160. The components other than the cassette spring 140 are made of resin, for example. The cassette spring 140 is made of, for example, a steel material.

The drug cartridge 100 has a cylindrical shape. The direction parallel to the axis a of the cylindrical shape of the drug cartridge 100 is referred to as the axial direction A. Also define the radial direction R centered on the axis a in the cross section perpendicular to the axis a. These directions may be referred to similarly with respect to the axis of the cassette outer sheath 120, the needle guard 130, the cassette spring 140 and the syringe retaining sheet 160.

Figure 4:
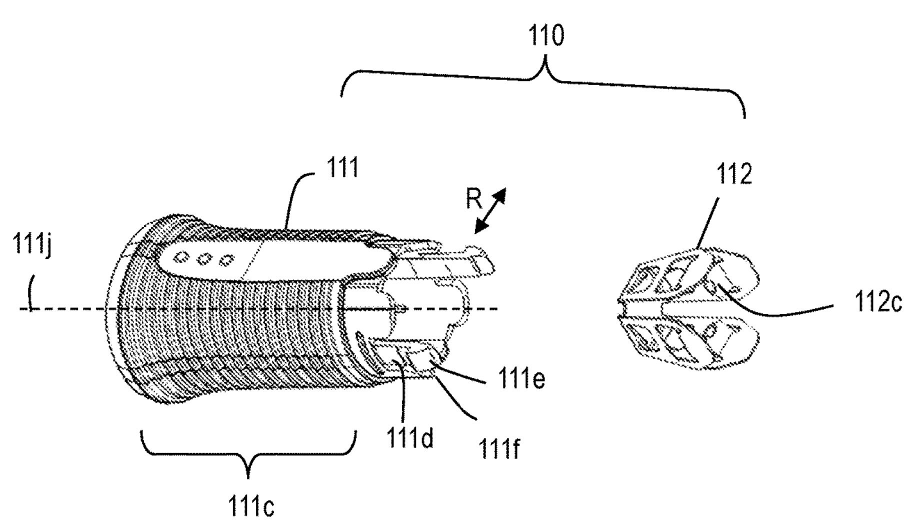
FIG. 4 is an exploded perspective view of a cap.

FIG. 4 is an exploded perspective view of the cap 110. The cap 110 includes a cap main body 111 and a cap spring 112. The cap main body 111 includes a cylindrical trunk portion 111*c*, an elastic support portion 111*d* (the first elastic support portion), and an engagement claw 111*e* (the first engagement claw). In the present embodiment, the cap main body 111 includes a pair of elastic support portions 111*d*. A pair of elastic support portions 111*d* are arranged separated from each other in the radial direction with respect to an axis 111*j* of the cylindrical trunk portion 111*c*, and one end of each is located at one end of the trunk portion 111*c*. An engagement claw 111*e* is located at the other end of each elastic support portion 111*d*. The engagement claw 111*e* has a contact surface 111*f* on the outer side in the radial direction. The elastic support portion 111*d* can flex toward the center of the radial direction R.

The cap spring 112 is arranged in the trunk portion 111*c* of the cap main body 111. In the present embodiment, the cap spring 112 includes a plurality of claws 112*c*. The claws 112*c* are arranged so that their tips point toward the tip of the trunk portion 111*c* and toward the axis 111*j* in the space within the trunk portion 111*c*. The claw 112*c* can mate with the engaging portion 14*a* of the needle shield 14 of the pre-filled syringe 10.

Figure 5:
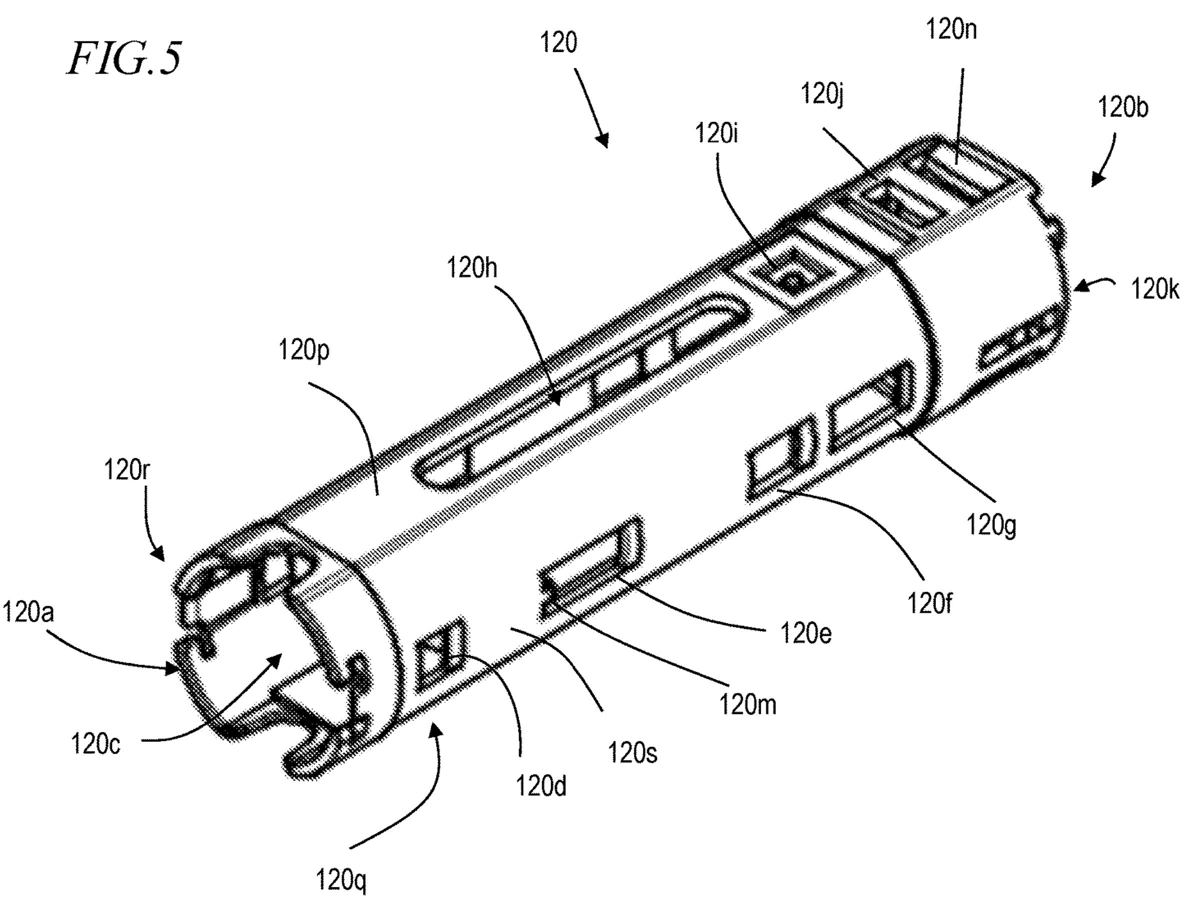
FIG. 5 is a perspective view of a cassette outer sheath.

FIG. 5 is a perspective view of the cassette outer sheath 120. The cassette outer sheath 120 has a cylindrical shape. In the present embodiment, the cassette outer sheath 120 is composed of flat portions 120*p* and 120*q*, which are generally flat, and curved portions 120*r* and 120*s*, which have a partially cylindrical side surface shape. The curved portions 120*x* and 120*s* connect together the flat portions 120*p* and 120*q*. With such a shape, the drug cartridge 100 is less likely to roll on a desk, etc. When the operator loads the drug cartridge 100 into the drug injection device 200, it is easy to specify the loading angle (the angle of rotation around the axis of the cylindrical shape) of the drug cartridge 100. For example, if the loading angle of the drug cartridge 100 is adjusted so that the two flat surfaces of the cylindrical shape of the cassette outer sheath 120 are parallel to the two flat surfaces of the outer case 201 of the drug injection device 200, the drug cartridge 100 can be correctly loaded into the drug injection device 200.

Figure 9A:
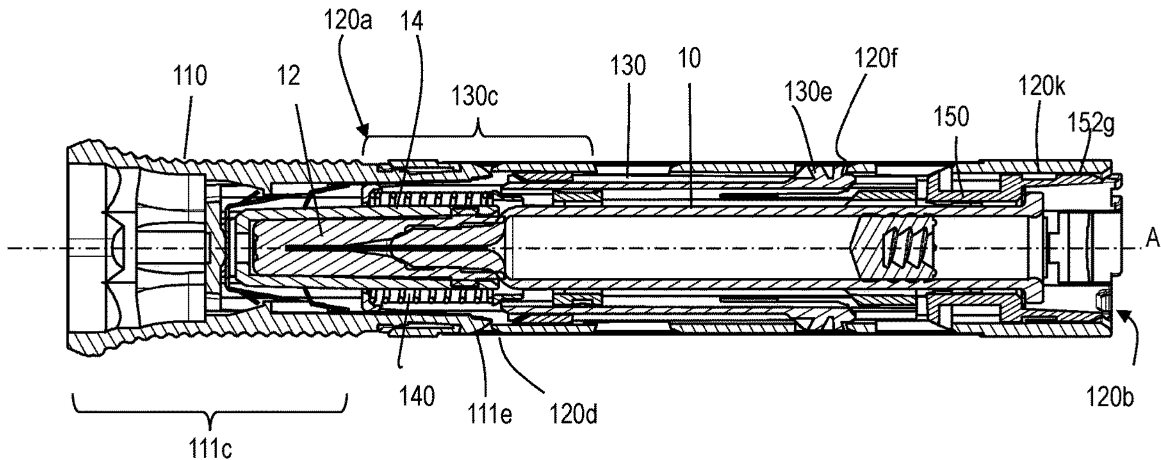
FIG. 9A is a schematic axial cross-sectional view showing the drug cartridge in one state.

The cassette outer sheath 120 includes a cassette rear opening 120*b* located at the rear end, a cassette front opening 120*a* located at the front end, and a cassette columnar space 120*c* located between the cassette rear opening 120*b* and the cassette front opening 120*a*. The cassette outer sheath 120 further includes a pair of sleeve engagement portions 120*k* on the inner surface on the side of the cassette rear opening 120*b* (FIG. 9A). The sleeve engagement portions 120*k* may be openings, claws, recesses, etc.

The cassette outer sheath 120 includes a cap engagement portion 120*d*, a first opening 120*f*, a second opening 120*e*, a third opening 120*g*, a window 120*h*, a recess 120*i*, a slit 120*j* and a piston unit engagement portion 120*n*. In the present embodiment, the cassette outer sheath 120 includes two each of cap engagement portions 120*d*, second openings 120*e*, first openings 120*f* and third openings 120*g*. One each of the cap engagement portion 120*d*, the second opening 120*e*, the first opening 120*f* and the third opening 120*g* are provided on the curved portion 120*x* and on the curved portion 120*s*. In the present embodiment, the cap engagement portion 120*d*, the second opening 120*e*, the first opening 120*f* and the third opening 120*g* are aligned in a row parallel to the axis of the cylindrical shape of the cassette outer sheath 120.

The cap engagement portion 120*d* is located on the cassette front opening 120*a* side of the cassette outer sheath 120. The first opening 120*f* is located on the cassette rear opening 120*b* side of the cassette outer sheath 120. The second opening 120*e* is located on the cassette front opening 120*a* side of the cassette outer sheath 120 relative to the first opening 120*f*. The third opening 120*g*, for example, is located on the cassette rear opening 120*b* side relative to the first opening 120*f*.

The cap engagement portion 120*d* is a recess, an opening, a protrusion, etc., capable of engaging with an engagement claw, a protrusion, etc. Hereinafter, in the present specification, an engagement portion is a recess, an opening, a protrusion, etc., capable of engaging with an engagement claw, a protrusion, etc., unless a particular shape is mentioned.

Each of the first opening 120*f*, the second opening 120*e* and the third opening 120*g* is a through opening reaching the outer surface and the inner surface of the cassette outer sheath 120. The cassette outer sheath 120 further includes an in-opening protrusion 120*m* protruding from an edge of the second opening 120*e* on the cassette front opening 120*a* side toward the center of the second opening 120*e*.

The window 120*h*, the recess 120*i* and the slit 120*j* are located on the flat portion 120*p*. The window 120*h*, for example, has a length along the axis of the cassette outer sheath 120. The slit 120*j* is located on the cassette rear opening 120*b* side of the cassette outer sheath 120 and extends in a direction perpendicular to the axis of the cassette outer sheath 120. The recess 120*i* is located, for example, between the window 120*h* and the slit 120*j*.

The piston unit engagement portion 120*n* engages with a piston unit 286 of the drug injection device 200, as described below. In the present embodiment, the piston unit engagement portion 120*n* is an opening.

Figure 6:
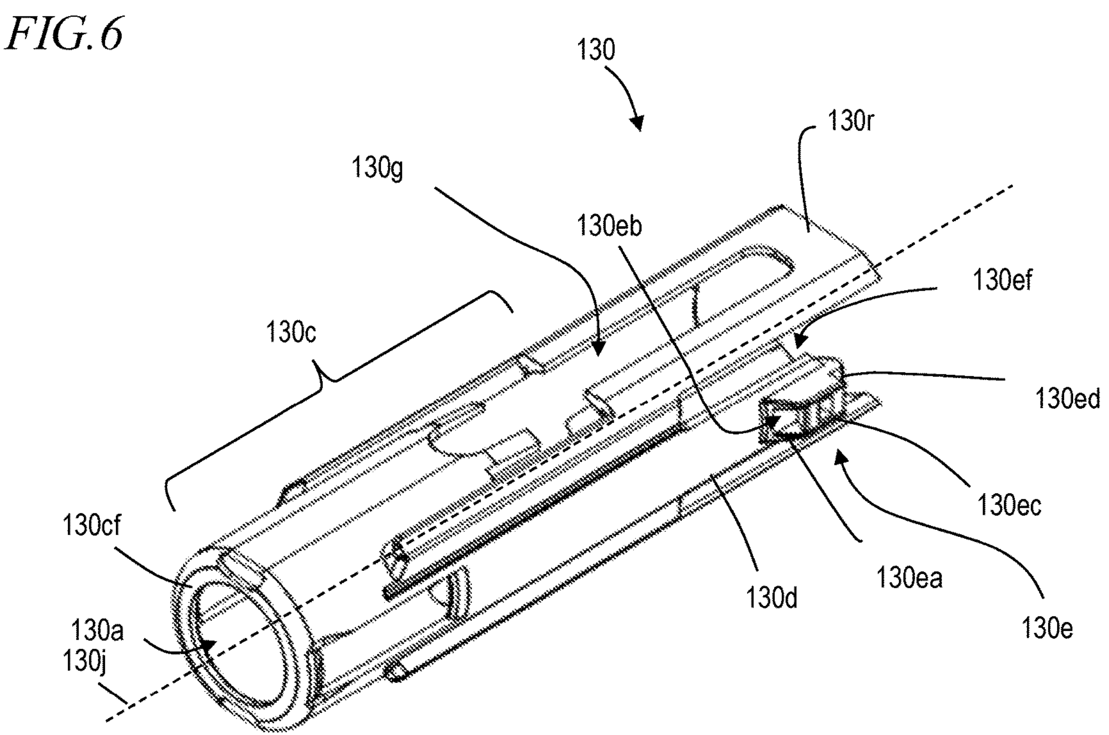
FIG. 6 is a perspective view of a needle guard.

FIG. 6 is a perspective view of the needle guard 130. The needle guard 130 includes a guard portion 130*c*, an elastic support portion 130*d* (the second elastic support portion) and a protrusion 130*e*. The needle guard 130 also includes an opening 130*g* and a reflective portion 130*r* located closer to the rear end than the opening 130*g*.

The guard portion 130*c* has a cylindrical shape that defines a needle guard columnar space that can house a portion of the syringe barrel 11 of the pre-filled syringe 10. The guard portion 130*c* includes an end face portion 130*cf* and a needle guard opening 130*a* provided at the end face portion 130*cf*.

One end of the elastic support portion 130*d* is connected to one end of the guard portion 130*c* opposite to the end face portion 130*cf*. The protrusion 130*e* is arranged at the other end of the elastic support portion 130*d*. In the present embodiment, the needle guard 130 includes a pair of protrusions 130*e* and a pair of elastic support portions 130*d*, and the pair of elastic support portions 130*d* are arranged in symmetry with an axis 130*j* of the needle guard 130 interposed therebetween.

The protrusion 130*e* includes a slope portion 130*ea* located on the guard portion 130*c* side and sloping outward, i.e., toward the cassette outer sheath 120 as the needle guard 130 is inserted into the cassette outer sheath 120, a recess 130*eb* located on the slope portion 130*ea*, a top portion 130*ec* adjacent to the slope portion 130*ea*, a side portion 130*ed* adjacent to the top portion 130*ec* on the opposite side of the slope portion 130*ea* in the direction in which the elastic support portion 130*d* extends, and an inner surface portion 130*ef* located inward relative to the slope portion 130*ea*, the top portion 130*ec* and the side portion 130*ed*.

Figure 7:
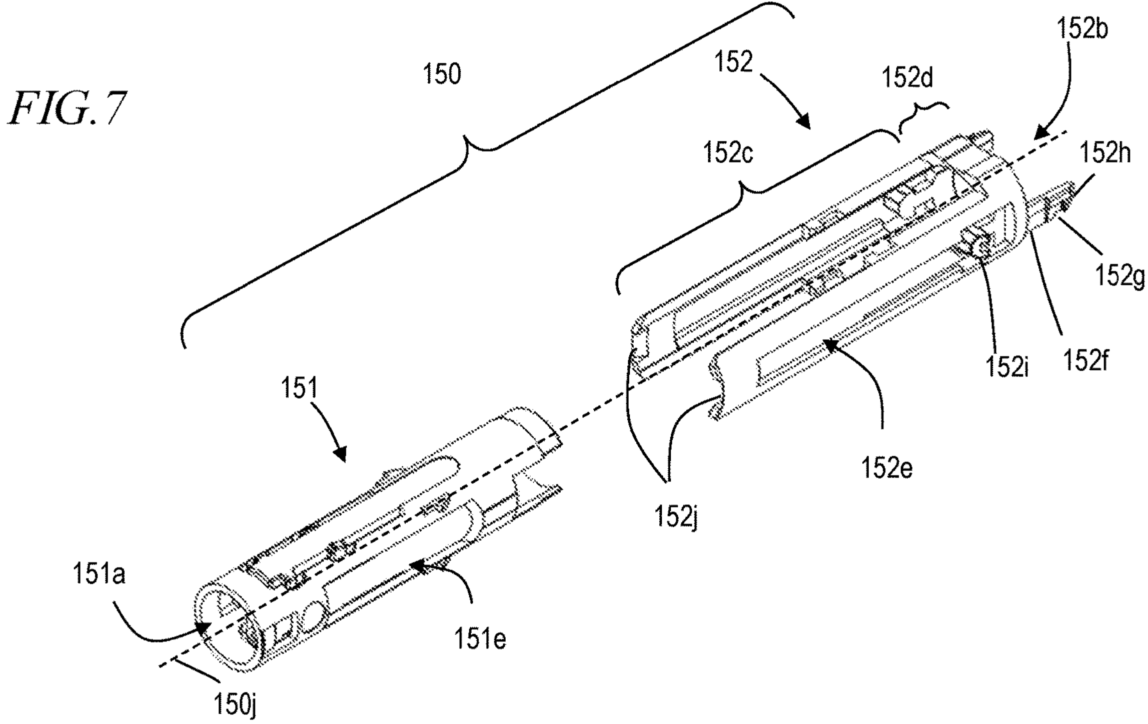
FIG. 7 is an exploded perspective view of a sleeve.

FIG. 7 is an exploded perspective view of the sleeve 150. The sleeve 150 includes an inner cylinder portion 151 and a sleeve main body 152. The inner cylinder portion 151 has a cylindrical shape having a space that houses a portion of the pre-filled syringe, and includes a sleeve front opening 151*a* on the front bottom surface of the cylindrical shape. The inner cylinder portion 151 also includes a pair of slits 151*e* on the side surface of the cylindrical shape. The slits 151*e* have a length in a direction parallel to an axis 150*j*.

The sleeve main body 152 includes an outer cylinder portion 152*c* and a base portion 152*d*. In the present embodiment, the sleeve main body 152 includes a pair of outer cylinder portions 152*c*. The pair of outer cylinder portions 152*c* are connected to the front end of the base portion 152*d*. A sleeve rear opening 152*b* is provided on the rear side of the base portion 152*d*.

Each of the outer cylinder portions 152*c* has a partially cylindrical side surface shape. These outer cylinder portions 152*c* are arranged in symmetry with the axis 150*j* of the sleeve 150 interposed therebetween. A wedge-shaped portion 152*j* is provided at the tip of each outer cylinder portion 152*c* to disengage the engagement between the engagement claw 111*e* of the cap 110 and the cap engagement portion 120*d* of the cassette outer sheath 120. Each outer cylinder portion 152*c* has a slit 152*e* having a length in a direction parallel to the axis 150*j*.

The sleeve main body 152 further includes an elastic support portion 152*f*, an engagement claw 152*g* (the second engagement claw) and a protrusion 152*i*. In the present embodiment, the sleeve main body 152 includes a pair of elastic support portions 152*f*, the engagement claw 152*g* and the protrusion 152*i*. One end of each of the pair of elastic support portions 152*f* is connected near the sleeve rear opening 152*b*. The engagement claw 152*g* is connected to the other end of the elastic support portion 152*f*. The engagement claw 152*g* has a contact surface 152*h* on the outer side in the radial direction. The elastic support portion 152*f* can flex in the radial direction. The protrusion 152*i* is provided on the base portion 152*d* adjacent to the slit 152*e*.

The inner cylinder portion 151 is connected to the front end of the base portion 152*d* of the sleeve main body 152. As shown in FIG. 3, a pair of outer cylinder portions 152*c* are arranged separated from each other in the radial direction centered on the axis 150*j* with respect to the inner cylinder portion 151. The slit 151*e* of the inner cylinder portion 151 and the slit 152*e* of the outer cylinder portion 152*c* are aligned in the radial direction. As described below, the needle guard 130 is inserted between the inner cylinder portion 151 and the outer cylinder portion 152*c*.

The components of the drug cartridge described above are assembled in the arrangement shown in FIG. 3. The cap 110 is fitted into the cassette front opening 120*a* of the cassette outer sheath 120. The needle guard 130 is inserted between the inner cylinder portion 151 and the outer cylinder portion 152*c* of the sleeve 150 with the cassette spring 140 inserted within the needle guard columnar space. The needle guard 130, the cassette spring 140 and the sleeve 150 are inserted into the cassette columnar space 120*c* of the cassette outer sheath 120.

As described above with reference to FIG. 7 and FIG. 3, the slit 151*e* of the inner cylinder portion 151 and the slit 152*e* of the outer cylinder portion 152*c* are aligned in the radial direction. Furthermore, the needle guard 130 and the sleeve 150 are aligned so that at least the protrusion 130*e* and the elastic support portion 130*d* of the needle guard 130 are aligned in the radial direction (the same orientation) with the slit 151*e* of the inner cylinder portion 151 of the sleeve 150 and the slit 152*e* of the outer cylinder portion 152*c* on a cross section perpendicular to the axis a. Thus, although the needle guard 130 is located between the inner cylinder portion 151 and the outer cylinder portion 152*c*, the elastic support portion 130*d* can flex in the radial direction.

Figure 8:
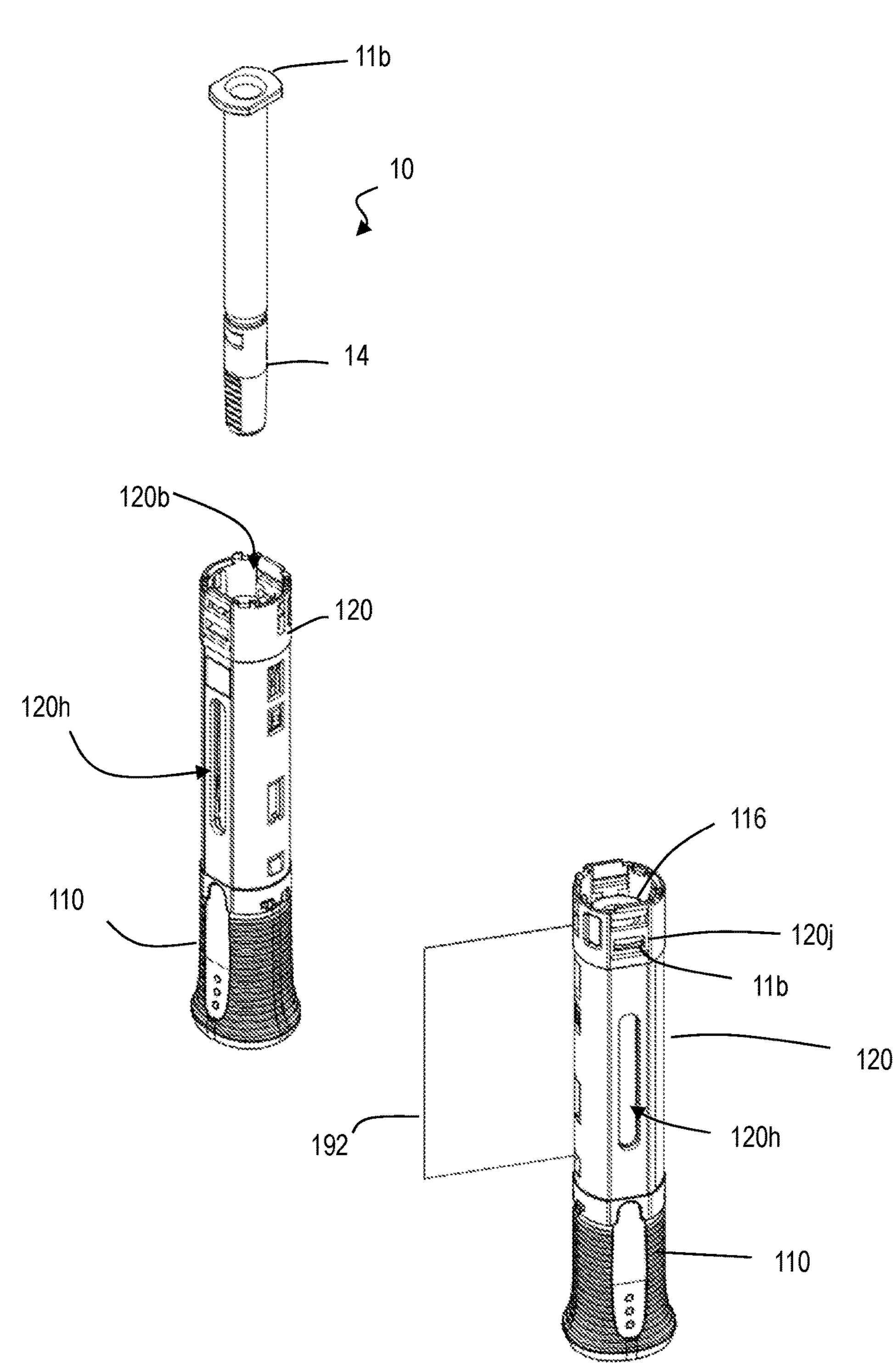
FIG. 8 is a diagram showing the procedure for assembling a drug cartridge.

The pre-filled syringe 10 is inserted into the cassette 105 thus assembled. As shown in FIG. 8, the pre-filled syringe 10 is inserted through the cassette rear opening 120*b* of the cassette outer sheath 120, the needle shield 14 first. By inserting the flange 11*b* of the syringe barrel 11 into the slit 120*j* of the cassette outer sheath 120 and similarly inserting the outer edge of the syringe retaining sheet 160 into the slit 120*j*, the pre-filled syringe 10 is retained in the cassette outer sheath 120.

In this state, the pre-filled syringe 10 held inside can be seen through the window 120*h* of the cassette outer sheath 120. It is also possible to check if the pre-filled syringe 10 is filled with the drug.

A label 192 may be affixed to the outer surface of the cassette outer sheath 120, indicating information regarding the type and amount of drug filled in the pre-filled syringe 10, as well as the date of manufacture and expiration date of the pre-filled syringe 10. If the drug cartridge 100 has the label 192 thereon, the label 192 preferably does not cover the window 120*h*.

A radio tag 190 may be provided in the recess 120*i* of the cassette outer sheath 120. The radio tag 190 is also called RFID (Radio Frequency Identification) and is capable of transmitting and receiving information by short-range communication using, for example, UHF or HF band radio waves. The radio tag 190 has a memory that stores, for example, information regarding the type and amount of drug filled in the pre-filled syringe 10, as well as the date of manufacture and expiration date of the pre-filled syringe 10. The radio tag 190 is covered by a seal 191. The radio tag 190 may be of a type that allows information to be appended or rewritten from outside in order to record usage. In this case, the radio tag 190 preferably has a security function, such as being able to append or rewrite information only from an authenticated writer, so that the recorded information cannot be tampered with.

[Operation of Drug Cartridge 100]

Next, the operation of the drug cartridge 100 will be described. In general use, the drug cartridge 100 is loaded into the drug injection device 200, the cap 110 is removed, and the needle guard 130 is made to protrude (ejected), etc. However, for ease of understanding, the operation of the drug cartridge 100 will be described as separated from the drug injection device 200. FIG. 9A to FIG. 9D are schematic cross-sectional views through the axis A of the drug cartridge 100 in various states. FIG. 10A to FIG. 10D are perspective views of the drug cartridge 100 corresponding to the states shown in FIG. 9A to FIG. 9D, respectively, with the cassette outer sheath 120 removed. For ease of understanding, a part of the structure of the drug cartridge 100 is not shown in FIG. 9A to FIG. 9D.

TABLE 1

| State of drug cartridge 100 | Position and/or state of each section | | |
|---|---|---|---|
| | Cap 110 | Needle guard 130 | Sleeve 150 |
| (1) Before loading | Locked | First engagement position (unlocked) | First position (locked) |
| (2) Loading (initial state) | Unlocked | First engagement position (locked) | Second position (Locked by latch unit) |
| (3) Removed cap | Removed | First engagement position (locked) | Second position (Locked by latch unit) |
| (4) Eject needle guard | — | Second engagement position (locked) | First position (locked) |

Figures 10A, 10B, 10C, 10D:
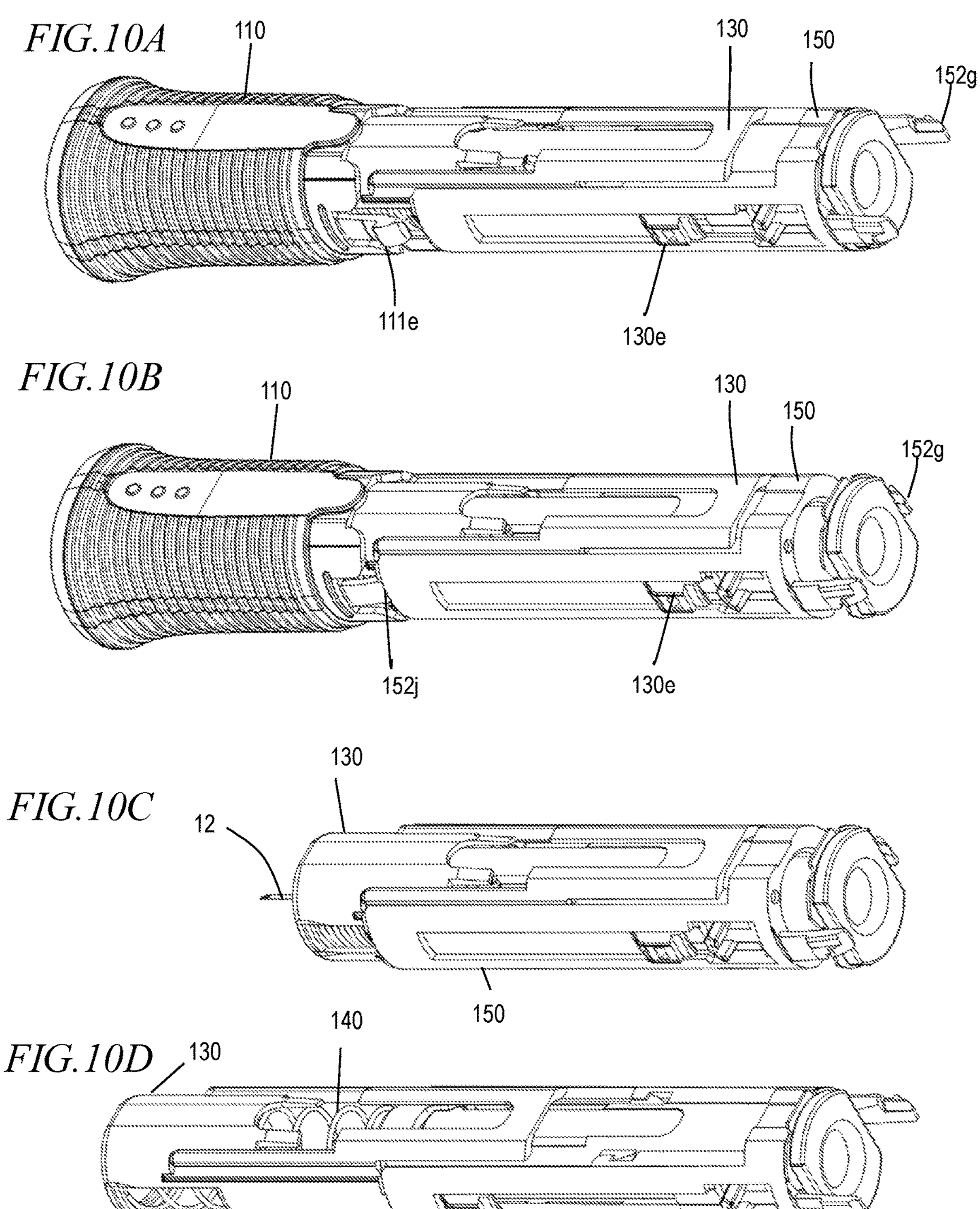
FIG. 10A is a perspective view of the drug cartridge in one state with the cassette outer sheath removed.
FIG. 10B is a perspective view of the drug cartridge in one state with the cassette outer sheath removed.
FIG. 10C is a perspective view of the drug cartridge in one state with the cassette outer sheath removed.
FIG. 10D is a perspective view of the drug cartridge in one state with the cassette outer sheath removed.

(1) Before Loading (FIG. 9A, FIG. 10A)

The drug cartridge 100 is in a state prior to loading into the drug injection device 200. As described above with reference to FIG. 8, the pre-filled syringe 10 is unmovably supported in the cassette columnar space by inserting the flange 11*b* of the syringe barrel 11 into the slit 120*j* of the cassette outer sheath 120. In this state, a part of the injection needle 12 and a part of the needle shield 14 of the pre-filled syringe 10 protrude from the cassette front opening 120*a*.

The cap 110 is fitted into the cassette front opening 120*a* of the cassette outer sheath 120. In this state, the cap main body 111 surrounds the cassette front opening 120*a*, and the engagement claw 111*e* is inserted through the cassette front opening 120*a* into the cassette outer sheath 120 and engages with the cap engagement portion 120*d* of the cassette outer sheath 120. Thus, the cap 110 cannot be detached from the cassette front opening 120*a*. The cap 110 is mated with the needle shield 14 and covers the needle shield 14.

The sleeve 150 is arranged outside the syringe barrel 11 of the pre-filled syringe 10 and is movable in the cassette columnar space in the axial direction A. In the initial state, as shown in FIG. 9A, the sleeve 150 is arranged in the first position on the cassette rear opening 120*b* side. In this state, the engagement claw 152*g* of the sleeve 150 engages with the sleeve engagement portion 120*k* located on the inner surface of the cassette outer sheath 120 on the cassette rear opening 120*b* side, and the sleeve 150 is engaged with the cassette outer sheath 120. Thus, the sleeve 150 is suppressed from moving to the second position, which is the forward position.

The needle guard 130 is movable in the cassette columnar space in the axial direction A, and in the initial state, the needle guard 130 is arranged in the first engagement position, where the tip of the guard portion 130*c* has moved backward relative to the tip of the injection needle 12 protruding from the cassette front opening 120*a*. In this state, the protrusion 130*e* of the needle guard 130 is engaged with the first opening 120*f* of the cassette outer sheath 120.

As shown in FIG. 9A, the cassette spring 140 is arranged within the guard portion 130*c* of the needle guard 130. One end of the cassette spring 140 is in contact with the needle guard 130 and the other end of the cassette spring 140 is in contact with the sleeve 150. Specifically, one end of the cassette spring 140 is in contact with the inner surface of the end face portion 130*cf* (FIG. 6) of the needle guard 130 and the other end is in contact with the front end (FIG. 7) of the inner cylinder portion 151 of the sleeve 150. In the initial state, the cassette spring 140 is pushed down against its biasing force.

In the state prior to loading into the drug injection device, the cap 110 is fitted into the cassette front opening 120*a* of the cassette outer sheath 120. The cap 110 is locked and cannot be detached from the cassette outer sheath 120 as the engagement claw ille of the cap 110 is engaged with the cap engagement portion 120*d* of the cassette outer sheath 120. At this point, the front end of the guard portion 130*c* of the needle guard 130 is in contact with the rear end of the trunk portion 111*c* of the cap 110.

Thus, when the drug cartridge 100 is not loaded into the drug injection device 200, the cap 110 is attached to the cassette front opening 120*a* of the drug cartridge 100 and is locked. Therefore, even if the operator accidentally attempts to remove the cap 110, it is difficult to remove, thereby suppressing the cap 110 from detaching from the cassette outer sheath 120 to expose the injection needle 12, and suppressing the operator from touching the exposed injection needle 12.

The sleeve 150 is suppressed from moving in the axial direction A as the engagement claw 152*g* of the sleeve 150 is engaged with the sleeve engagement portion 120*k* of the cassette outer sheath 120. Therefore, even if the operator accidentally or intentionally attempts to push the sleeve 150 through the cassette rear opening 120*b* with a finger or the like, the sleeve 150 is suppressed from moving.

Figure 9B:
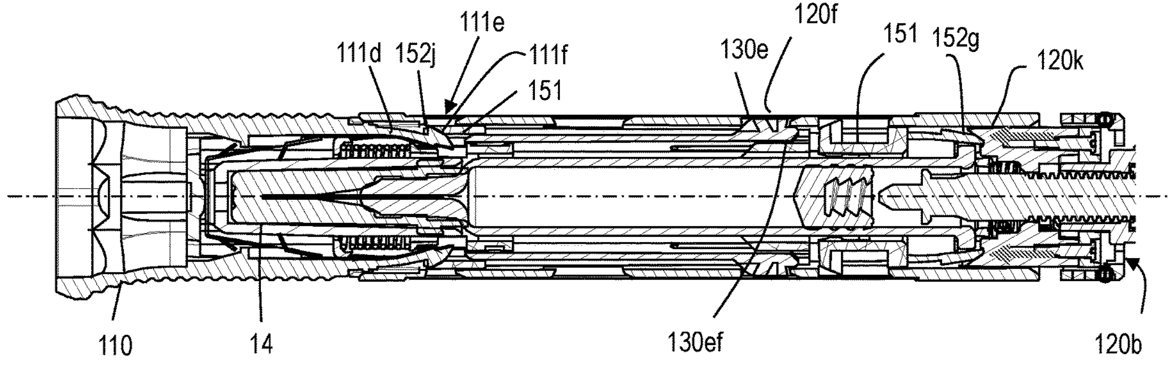
FIG. 9B is a schematic axial cross-sectional view showing the drug cartridge in one state.

(2) Loading State of Drug Cartridge 100 (FIG. 9B, FIG. 10B)

When the drug cartridge 100 is loaded into the drug injection device 200, a latch unit 230 is inserted through the cassette rear opening 120*b* and pushes the engagement claw 152G of the sleeve 150 in the forward direction while tilting the engagement claw 152G inward, as will be described in detail below. Thus, as shown in FIG. 9B, the sleeve 150 moves forward against the biasing force of the cassette spring 140 to move to the second position. Since the latch unit 230 is engaged with the cassette outer sheath 120, the sleeve 150, which is in contact with the latch unit 230, is in an unmovable locked position.

At this point, the wedge-shaped portion 152*j* of the tip of the outer cylinder portion 152*c* of the sleeve main body 152 of the sleeve 150 enters between the contact surface 111*f* of the engagement claw 111*e* of the cap 110 and the inner surface of the cassette outer sheath 120, thereby causing the elastic support portion 111*d* to flex inward, and disengaging the engagement between the engagement claw 111*e* and the cap engagement portion 120*d*. Thus, the cap 110 is in an unlocked state where the cap 110 can be detached from the cassette outer sheath 120. As the sleeve 150 moves to the second position, the inner surface portion 130*ef* of the protrusion 130*e* of the needle guard 130 contacts or comes close to the side surface of the inner cylinder portion 151 of the sleeve 150.

In this state, the operator can remove the cap 110 with their fingers. When the cap 110 is removed, the needle shield 14 is also removed together.

Figure 9C:
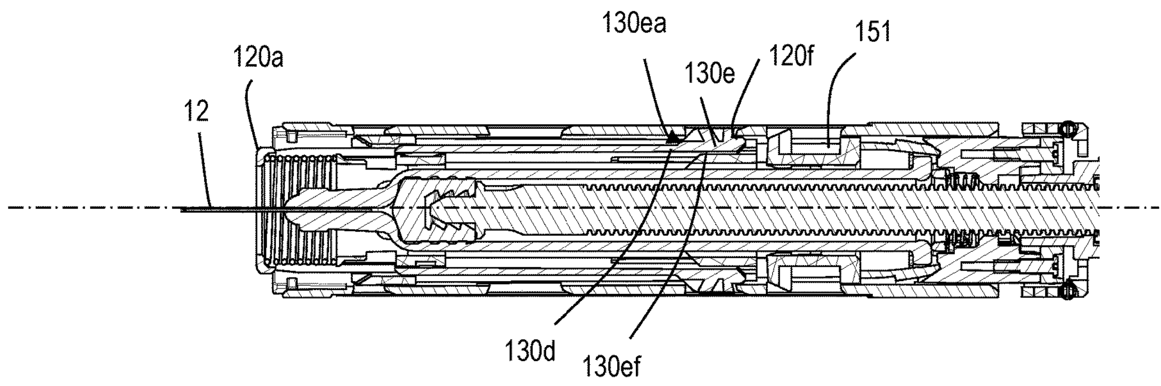
FIG. 9C is a schematic axial cross-sectional view showing the drug cartridge in one state.

(3) State where Cap is Removed (FIG. 9C, FIG. 10C)

With the cap 110 removed, there are no components that physically inhibit the needle guard 130 from moving forward. Thus, the needle guard 130 is biased in the direction of moving forward (protruding) by the biasing force from the cassette spring 140. Accordingly, the slope portion 130*ea* of the protrusion 130*e* contacts the edge of the first opening 120*f*, causing the elastic support portion 130*d* to flex inward. However, as the inner surface portion 130*ef* of the protrusion 130*e* contacts the inner cylinder portion 151 of the sleeve 150, the elastic support portion 130*d* is suppressed from further deforming. Thus, the needle guard 130 remains locked by the sleeve 150 in the second position.

In this state, the injection needle 12 protrudes from the cassette front opening 120*a*. As discussed below, in the pre-injection state, the injection needle 12 is located within the outer case 201 (FIG. 1C). When the operator depresses the injection button 254, the entire drug cartridge 100 moves forward and the injection needle 12 is inserted into the injection site of the operator.

Figure 9D:
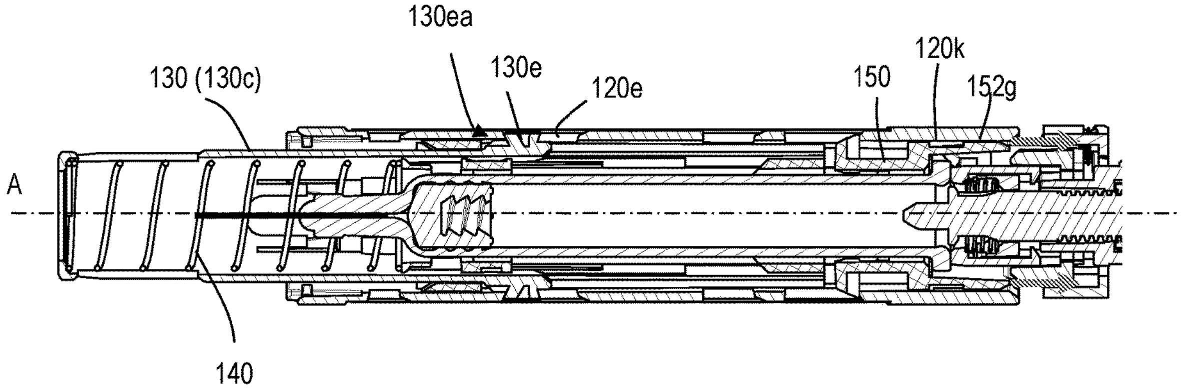
FIG. 9D is a schematic axial cross-sectional view showing the drug cartridge in one state.

(4) State where Needle Guard is Ejected (FIG. 9D, FIG. 10D)

When the injection is complete, the entire drug cartridge 100 moves backward, thereby removing the needle. This causes the injection needle 12 to move backward into the outer case 201 (FIG. 1C). As described below, when the latch unit 230 then rotates as the piston 221 moves backward, the contact between the latch unit 230 and the engagement claw 152*g* of the sleeve 150 is disengaged, allowing the sleeve 150 to move backward. As a result, the sleeve 150 moves backward by the biasing force of the cassette spring 140 and moves from the second position to the first position shown in FIG. 9D. The engagement claw 152*g* of the sleeve 150 engages with the sleeve engagement portion 120*k* located on the inner surface of the cassette outer sheath 120. This renders the sleeve 150 unmovable in the first position.

As the sleeve 150 moves to the first position, a space is formed on the inner side (on the axis a side) of the protrusion 130*e* of the needle guard 130, allowing deformation of the elastic support portion 130*d*. As a result, the slope portion 130*ea* of the protrusion 130*e* contacts the edge of the first opening 120*f* and the elastic support portion 130*d* flexes inward (toward the axis a) (FIG. 9C). Therefore, the protrusion 130*e* detaches from the first opening 120*f* inward (toward the axis a), and the needle guard 130 moves from the first engagement position to the second engagement position by the biasing force of the cassette spring 140. Thus, as shown in FIG. 9D, the protrusion 130*e* of the needle guard 130 engages with the second opening 120*e* of the cassette outer sheath 120. In this state, the guard portion 130*c* of the needle guard 130 surrounds the injection needle 12, and the tip of the guard portion 130*c* protrudes relative to the tip of the injection needle 12 protruding from the cassette front opening 120*a*.

Figure 11A:
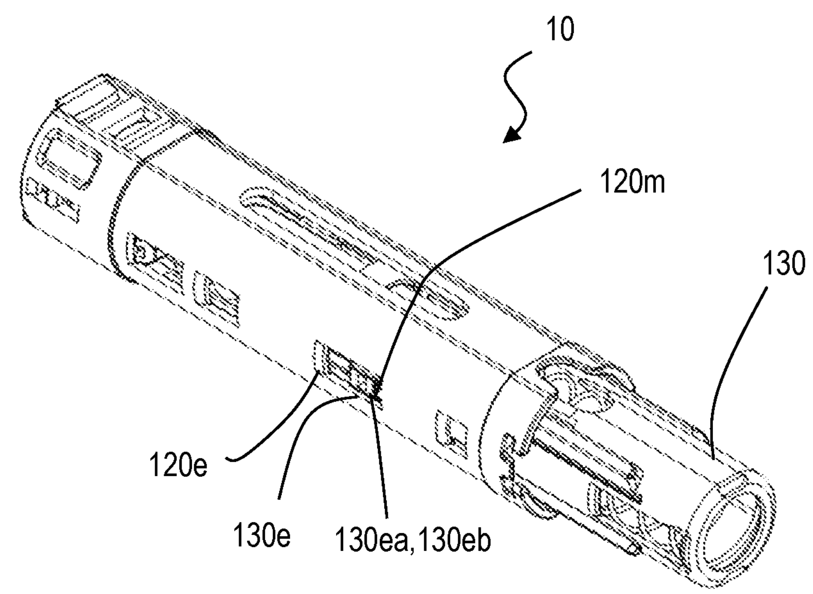
FIG. 11A is a perspective view of the drug cartridge with the needle guard protruding.
Figure 11B:
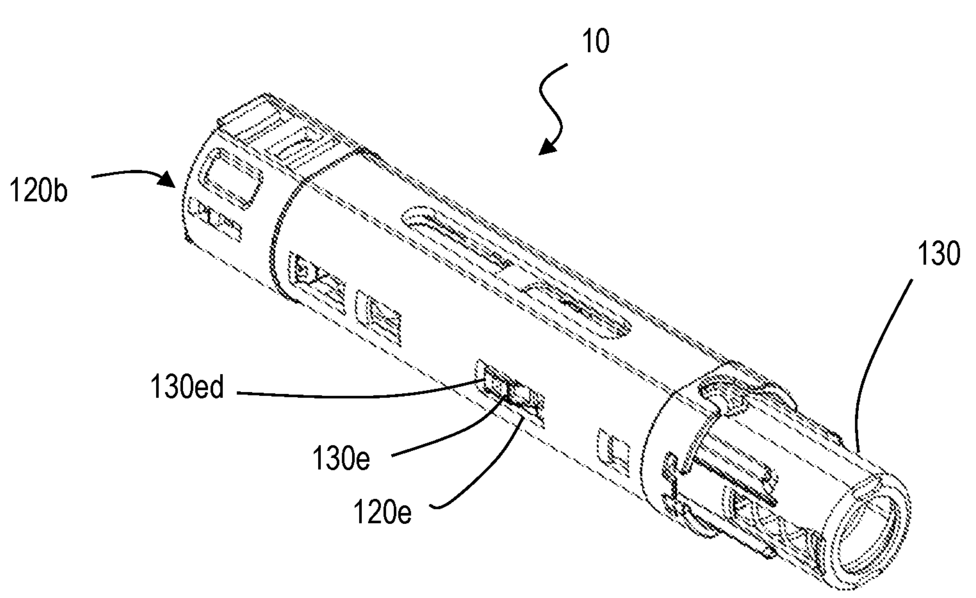
FIG. 11B is a perspective view of the drug cartridge with the needle guard protruding.

FIG. 11A and FIG. 11B are perspective views of the drug cartridge with the needle guard protruding. As shown in FIG. 11A, when the protrusion 130*e* is engaged with the second opening 120*e*, the slope portion 130*ea* of the protrusion 130*e* contacts the edge of the second opening 120*e* on the cassette front opening 120*a* side, and the in-opening protrusion 120*m* is engaged with the recess 130*eb* (FIG. 6) of the slope portion 130*ea*. Thus, this engagement suppresses deformation of the elastic support portion 130*d* and makes it difficult to pull out the needle guard 130 even if one attempts to pull out the needle guard 130 with fingers.

When one attempts to push in the needle guard 130 with fingers, the side portion 130*ed* of the protrusion 130*e* contacts the edge of the second opening 120*e* on the cassette rear opening 120*b* side, as shown in FIG. 11B. Because the side portion 130*ed* has a slope that is at an angle of bite relative to the edge on the cassette rear opening 120*b* side of the second opening 120*e* of the cassette outer sheath, the contact with the edge of the second opening 120*e* causes a force parallel to the direction in which the elastic support portion 130*d* extends to act upon the elastic support portion 130*d* (FIG. 6). Therefore, the elastic support portion 130*d* is suppressed from flexing as no force acts in the direction in which the elastic support portion 130*d* flexes. As a result, the protrusion 130*e* is suppressed from detaching from the second opening 120*e*. That is, it is difficult to push in the needle guard 130.

Thus, when the injection is complete, the injection needle 12 is covered by the needle guard 130. Thus, the operator is suppressed from accidentally touching the injection needle 12 when removing the used drug cartridge 100 from the drug injection device 200. The needle guard 130 is locked in a state where it is difficult to move forward or move backward. Thus, for example, when the removed drug cartridge 100 is disposed of or otherwise handled by the operator or a third party person, contact such as pricking a finger with the injection needle is suppressed even when the drug cartridge 100 is handled in various ways.

Accordingly, with the drug cartridge according to the present embodiment, the difficulty in removing the cap until the drug cartridge is loaded into the drug injection device suppresses inadvertent removal of the cap, resulting in fingers contacting the injection needle or contamination of the injection needle. Safety is maintained as the injection needle is located inside the drug injection device when the cap is removed. Furthermore, after injection, the needle guard covers the injection needle and the needle guard is locked in that state, thereby allowing safe handling of the used drug cartridge.

[Structure of Drug Injection Device 200]

<Outline of Configuration of Drug Injection Device 200>

Figures 12A, 12B:
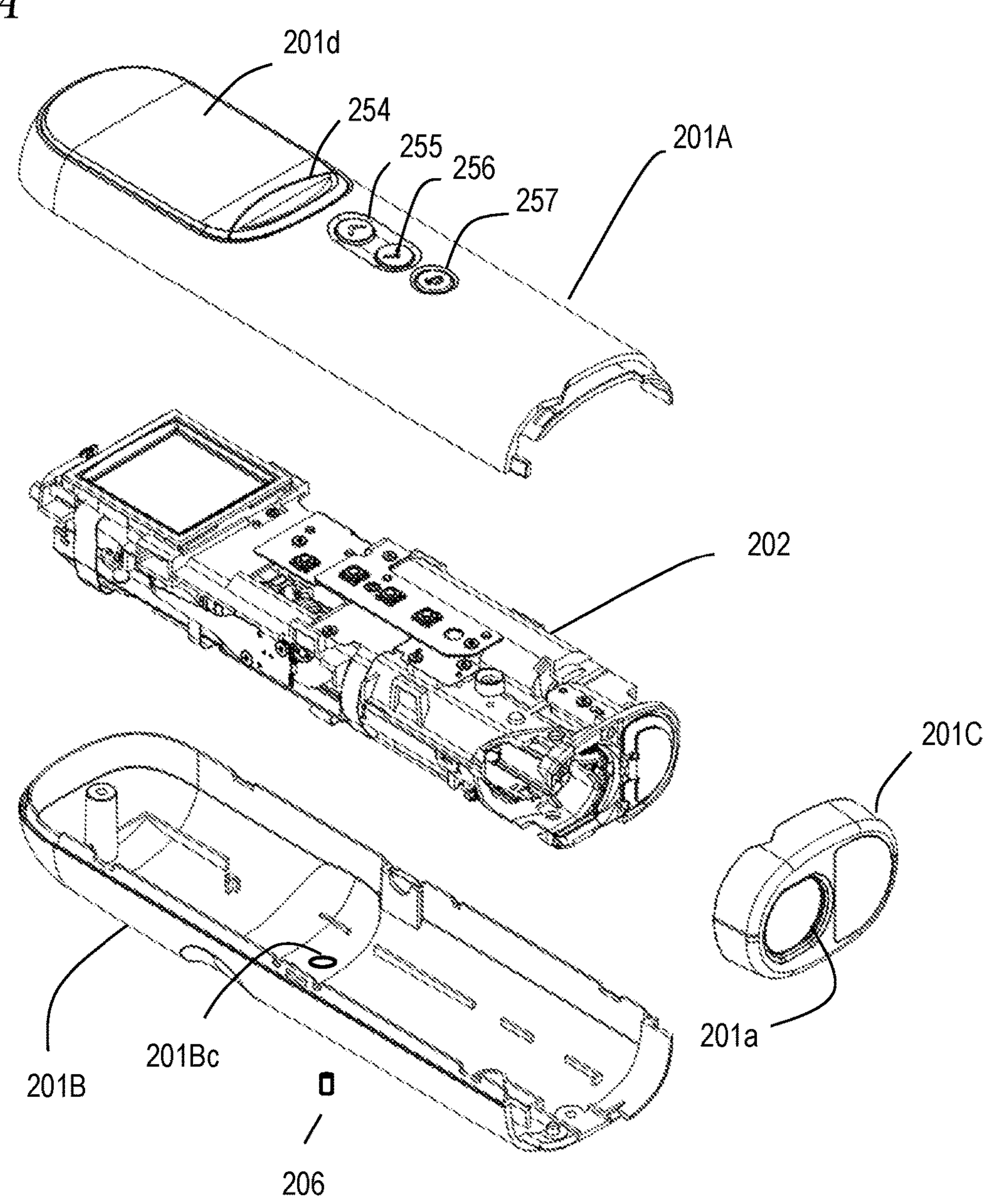
FIG. 12A is a perspective view where the outer case of the drug injection device is disassembled.
FIG. 12B is a perspective view showing a tip case as viewed from inside.

FIG. 12A is a perspective view of the outer case 201 of the drug injection device 200 disassembled. The drug injection device 200 includes a main body 202 housed in the outer case 201.

The outer case 201 includes an upper case 201A, a lower case 201B and a tip case 2010, for example. As described above, the display window 201D, the injection button 254, the select (upper) button 255, the select (lower) button 256 and the back button 257 are arranged in the upper case 201A. An emergency hole 201Bc may be provided in the lower case 201B. A removable screw 206 may be attached to the emergency hole 201Bc.

FIG. 12B is a perspective view of the tip case 201*c* as viewed from the inner side. The tip case 201C is provided with the cartridge opening 201*a*, and the door 203 is arranged inside. The door 203 is attached to the tip case 201C so that the door 203 can pivot inward around an axis 203*j*. The door 203 is biased in the direction of closing the cartridge opening 201*a* by a torsion spring 204.

Figure 13:
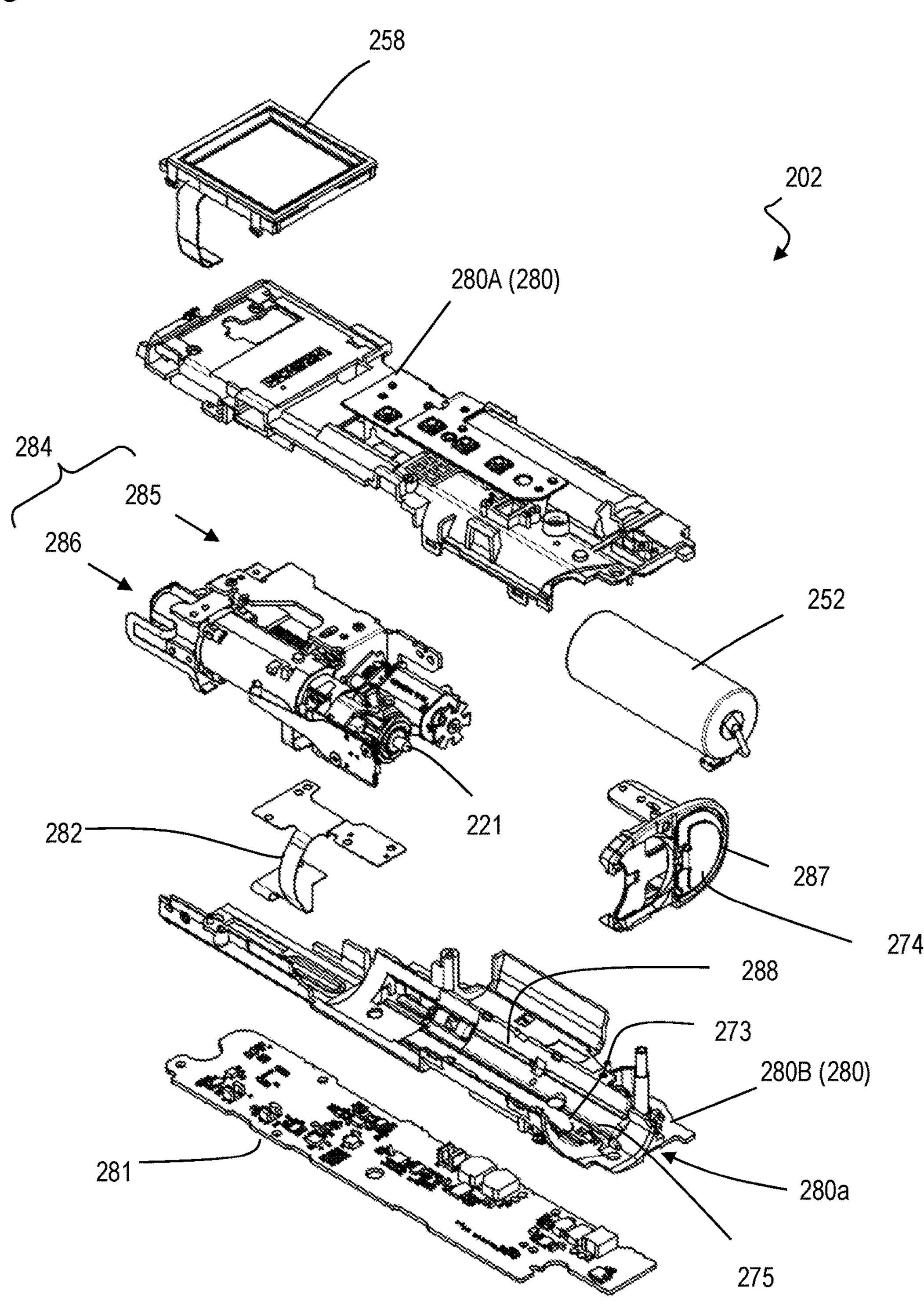
FIG. 13 is an exploded perspective view of the main body.

FIG. 13 is an exploded perspective view of the main body 202. The main body 202 includes an upper casing 280A, a lower casing 280B, a circuit board 281, a driver device 284, a touch sensor unit 287, a slider unit 288, a display device 258 and a battery 252. The upper casing 280A and the lower casing 280B, when combined, form a casing 280 having the cartridge space 280*a* (FIG. 1A) in which the drug cartridge 100 is loaded. A circuit that implements the functions of the block diagram shown in FIG. 14 is formed on the circuit board 281.

The driver device 284 includes a motor unit 285 and the piston unit 286. The motor unit 285 moves the piston unit 286 forward and backward, thereby moving the drug cartridge 100 engaged with the piston unit 286 forward and backward for needle insertion and needle removal. It also moves the piston 221 of the piston unit 286 forward and backward to inject the drug and disengage the engagement between the piston unit 286 and the drug cartridge 100.

The display device 258 displays information of the pre-filled syringe 10 held in the drug cartridge 100, displays the status of the drug injection device 200 and displays the operating procedures for the operator. The battery 252 supplies power to operate the drug injection device 200.

Figure 14:
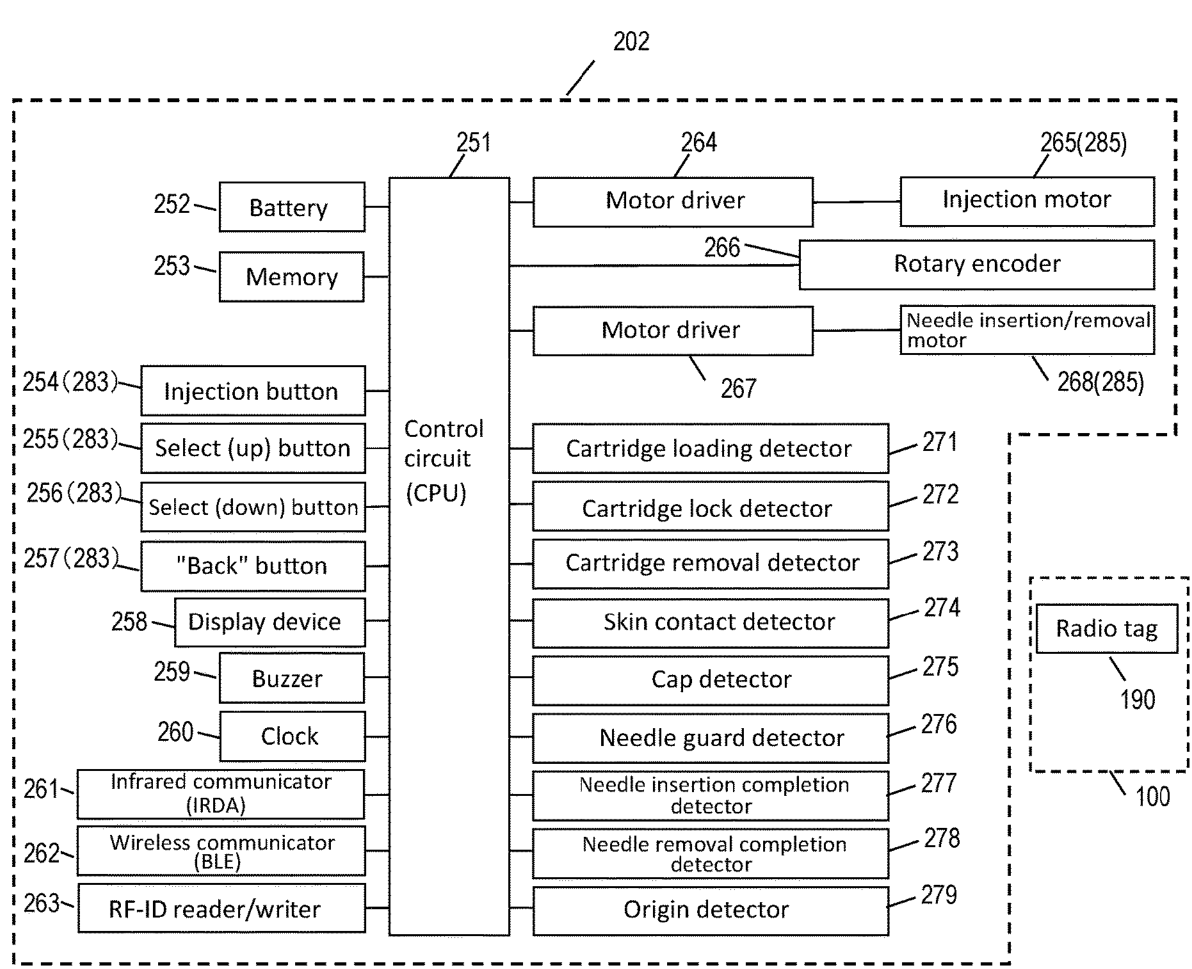
FIG. 14 is a block diagram showing a configuration of an electric circuit of the drug injection device.

FIG. 14 is a block diagram showing a configuration of an electric circuit of the drug injection device 200. The main body 202 includes a control circuit 251 that includes an arithmetic unit such as a CPU, a memory 253 that stores a computer program, data, etc., a buzzer 259 and a clock 260.

The control circuit 251 receives commands from an interface 283 (the injection button 254, the select (up) button 255, the select (down) button 256 and the back button 257), and at a timing based on the clock signal received from the clock 260, reads out the program stored in the memory 253 to control components including an injection motor 265 and a needle insertion/removal motor 268 to be described below according to the procedure of the computer program. The procedure of the computer program is illustrated in the description below and in the flow charts of the accompanying drawings. The buzzer 259 informs the operator by triggering an alarm based on the control by the control circuit 251.

The main body 202 further includes a motor driver 264, the injection motor 265, a motor driver 267 and the needle insertion/removal motor 268. The injection motor 265 and a needle insertion/removal motor 268 are incorporated into the motor unit 285 of the driver device 284 and serve as the power source. The motor driver 264 and the motor driver 267 generate current to drive these motors based on the control circuit 251.

The main body 202 further includes various sensors. Specifically, the main body 202 includes a rotary encoder 266, a cartridge loading detector 271, a cartridge lock detector 272, a cartridge removal detector 273, a skin contact detector 274, a cap detector 275, a needle guard detector 276, a needle insertion completion detector 277, a needle removal completion detector 278 and an origin detector 279. These detectors will be described in detail below.

The main body 202 may further include various communication devices. Specifically, the main body 202 may include an infrared communicator 261, a wireless communicator 262 and an RF-ID reader/writer 263. The infrared communicator 261 and the wireless communicator 262 transmit and receive information to and from the outside through infrared communications and wireless communications. The wireless communicator 262 may be a transmitter/receiver that uses a short-range wireless communication standard, such as BLE (Bluetooth Low Energy, Bluetooth is a registered trademark). For example, the time when the operator uses the drug injection device 200, the type of drug, the amount injected, and other information may be stored in the memory 253 at the time of use, and at a predetermined time, these information may be transmitted using the infrared communicator 261 or the wireless communicator 262 to a portable device such as a smartphone, a tablet terminal, or a device dedicated to managing the drug injection device 200. The information described above may also be transmitted from the portable device to a server, or the like, of a hospital or a drug manufacturer via a mobile telephone network or the Internet network.

The RF-ID reader/writer 263 reads the drug information transmitted from the radio tag 190 of the drug cartridge 100, including information regarding the type and amount of drug filled in the pre-filled syringe 10, the date of manufacture of the pre-filled syringe 10, and the expiration date. The information read is input to the control circuit 251 and may be displayed on the display 258 or used to control the operation of the drug injection device 200.

<Structure of Driver Device 284>

Figure 15:
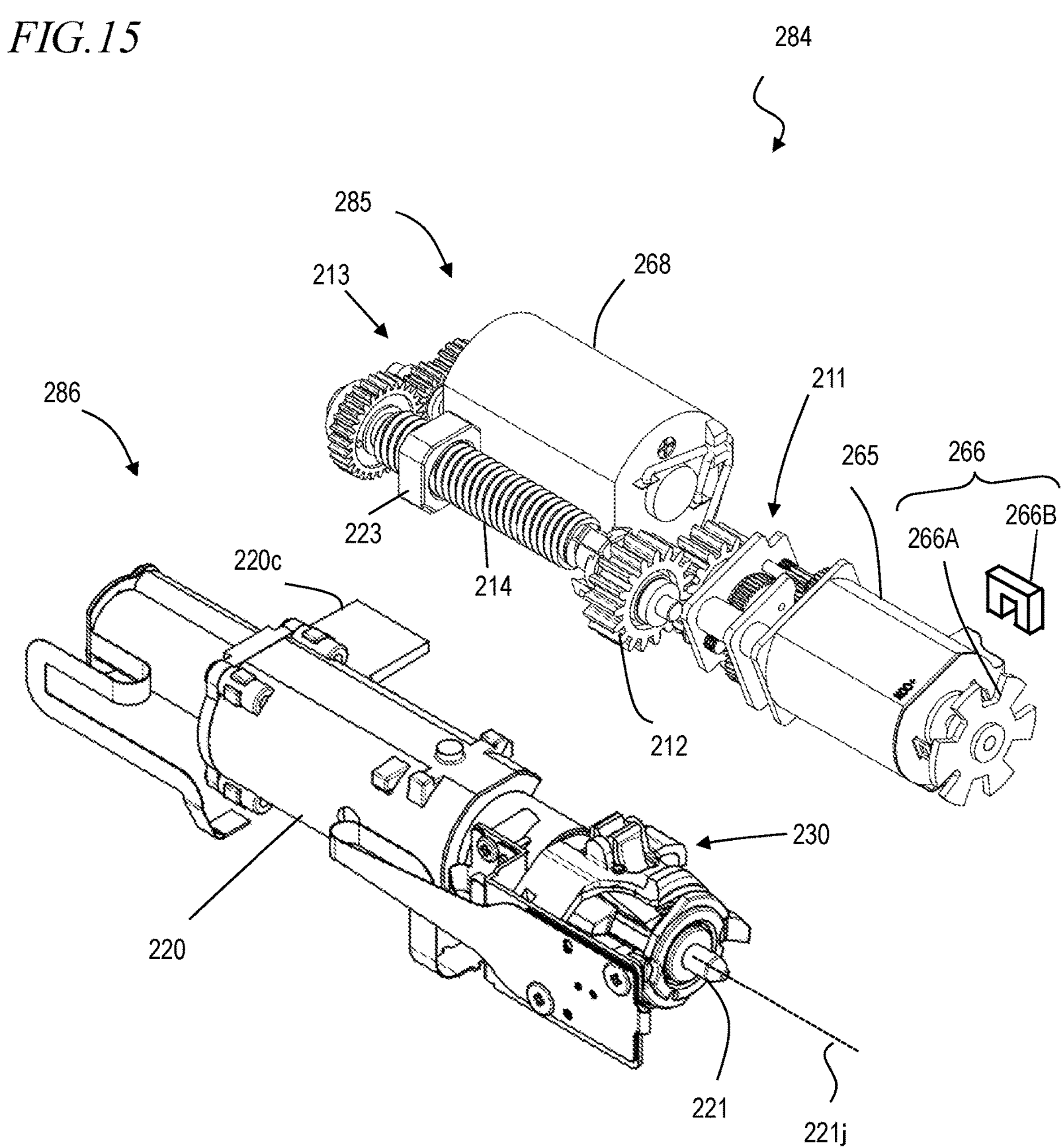
FIG. 15 is a perspective view of the driver device.

FIG. 15 is a perspective view of the driver device 284. For ease of understanding, some structures are not shown.

The driver device 284 includes the injection motor 265, the needle insertion/removal motor 268, and the piston unit 286 including the piston 221, wherein the needle insertion/removal motor 268 moves the entire piston unit 286 forward and backward in the direction of a piston axis 221*j*. The injection motor 265 moves the piston 221 forward and backward in the direction of the piston axis 221*j*. For this, the driver device 284 is composed of the motor unit 285 and the piston unit 286.

The motor unit 285 includes the injection motor 265, the rotary encoder 266, a gear device 211, a drive gear 212, a needle insertion/removal motor 268, a gear device 213 and a drive screw 214. The gear device 211 includes one or more gears and transmits the rotational force of the injection motor 265 to the drive gear 212. When the rotation of the injection motor 265 is reversed, the rotation of the drive gear 212 is also reversed. The gear device 213 also includes one or more gears and transmits the rotational force of the needle insertion/removal motor 268 to the drive screw 214. The drive screw 214 has a rod shape and has a male thread formed on the outer surface.

The piston unit 286 includes the piston 221, the latch unit 230, a piston case 220 and a nut 223. The piston case 220 supports the piston 221 so that the piston 221 is rotatable around the axis and movable in the axial direction. The piston case 220 includes a support portion 220*c* and the nut 223 is fixed to the support portion 220*c*. The nut 223 has a hole with a female thread formed therein and is inserted into the drive screw 214 of the motor unit 285 with their screws meshing with each other.

When the needle insertion/removal motor 268 of the motor unit 285 rotates, the rotational force is transmitted to the drive screw 214 via the gear device 213, causing the drive screw 214 to rotate. As the nut 223 is fixed to the piston unit 286, the nut 223 does not rotate together with the drive screw 214, but moves forward or backward relative to the drive screw 214. This causes the piston unit 286 to move forward or more backward.

The rotary encoder 266 includes an encoder plate 266A and a pulse encoder 266B, wherein the encoder plate 266A is attached to the rotary shaft of the injection motor 265. The encoder plate 266A has notches arranged at equal intervals along the circumference. The pulse encoder 266B includes a light-emitting element and a light-receiving element, and is arranged so that the outer circumference of the encoder plate 266A is positioned between the light-emitting element and the light-receiving element. As the encoder plate 266A rotates, light emitted from the light-emitting element is intermittently detected by the light-receiving element. Thus, the rotary encoder 266 generates a pulse signal having a pulse number corresponding to the number of revolutions (amount of rotation) of the injection motor 265, and detects the number of revolutions of the injection motor 265.

Figures 16A, 16B:
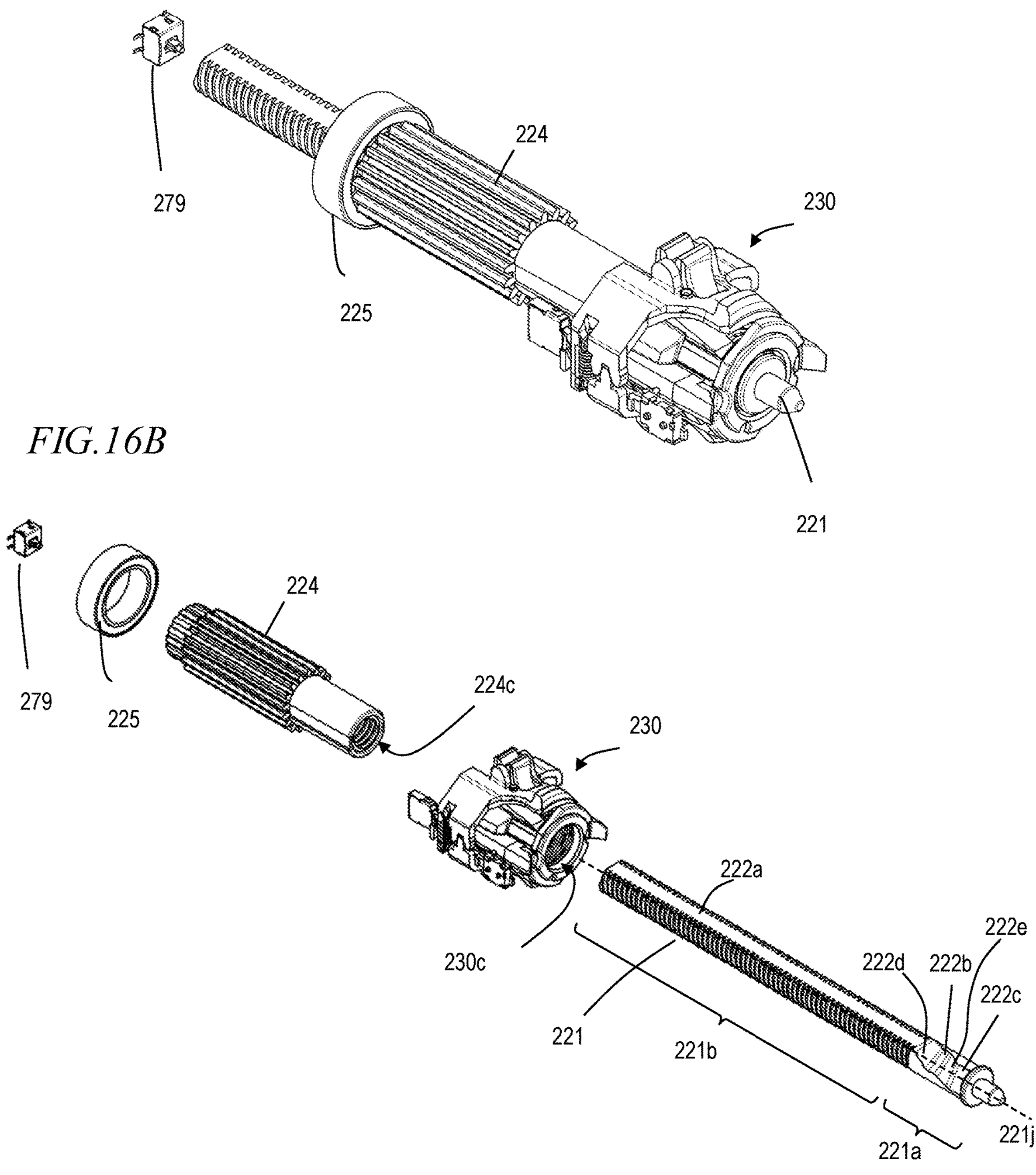
FIG. 16A is a perspective view of the piston unit with the piston case removed.
FIG. 16B is an exploded perspective view of the piston unit with the piston case removed.

FIG. 16A is a perspective view of the piston unit 286 with the piston case 220 removed, and FIG. 16B is an exploded perspective view of the piston unit 286 with the piston case 220 removed. The piston unit 286 includes the piston 221, the latch unit 230, a piston gear 224, a bearing 225 and the origin detector 279. The piston 221 moves forward the stopper 13 of the pre-filled syringe 10 supported by the drug cartridge 100 to inject the drug. The piston gear 224 drives the piston 221 in the direction of the piston axis 221*j*. The latch unit 230 is partially inserted into the cassette rear opening 120*b* of the drug cartridge 100 and grips the drug cartridge 100.

The piston 221 has a rod shape and includes a tip portion 221*a* and a base portion 221*b*. A male thread is formed on the side surface of the base portion 221*b*. The piston 221 has a shape that is notched parallel to the piston axis 221*j* on two flat surfaces that sandwich the piston axis 221*j* therebetween, and has an I-letter shape in a cross section perpendicular to the piston axis 221*j*.

The notch is twisted at the tip portion 221*a*, and the piston 221 has a helical contact surface at the tip portion 221*a*. Specifically, the piston 221 includes a pair of first flat surfaces 222*a* that sandwich the piston axis 221*j* therebetween at the base portion 221*b*. The piston 221 includes a pair of second flat surfaces 222*b* and a pair of third flat surfaces 222*c* at the tip portion 221*a*. The second flat surface 222*b* is located between the first flat surface 222*a* and the third flat surface 222*c*, and the third flat surface 222*c* is located furthest on the tip side of the piston 221. A helical surface 222*d* is arranged between the first flat surface 222*a* and the second flat surface 222*b*, and a helical surface 222*e* is arranged between the second flat surface 222*b* and the third flat surface 222*c*. The helical surface 222*d*, the second flat surface 222*b*, the helical surface 222*e* and the third flat surface 222*c* may be referred to as a helical structure.

Figure 16C:
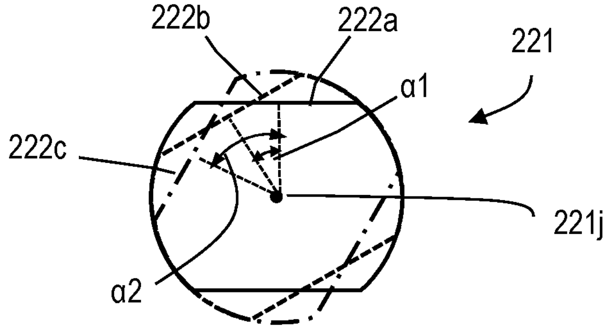
FIG. 16C is a diagram showing the positional relationship between the first flat surface, the second flat surface and the third flat surface as viewed from the tip side.

FIG. 16C shows the positional relationship between the first flat surface 222*a*, the second flat surface 222*b* and the third flat surface 222*c* in a cross section perpendicular to the piston axis 221*j* of the piston 221, as viewed from the tip side. The second flat surface 222*b* and the third flat surface 222*c* are arranged, with respect to the first flat surface 222*a*, at positions that are rotated counterclockwise around the piston axis 221*j*. The angle between the first flat surface 222*a* and the second flat surface 222*b* is $\alpha 1$ and the angle between the first flat surface 222*a* and the third flat surface 222*c* is $\alpha 2$ greater than $\alpha 1$ ($\alpha 1 < \alpha 2$).

Figure 16E:
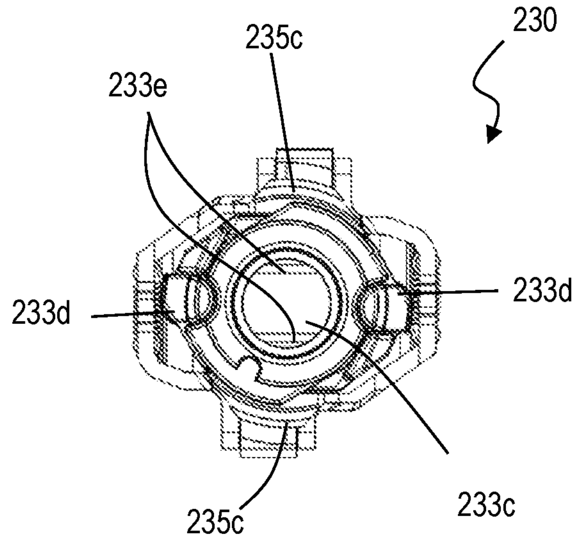
FIG. 16E is a front view of the latch unit.
Figure 16D:
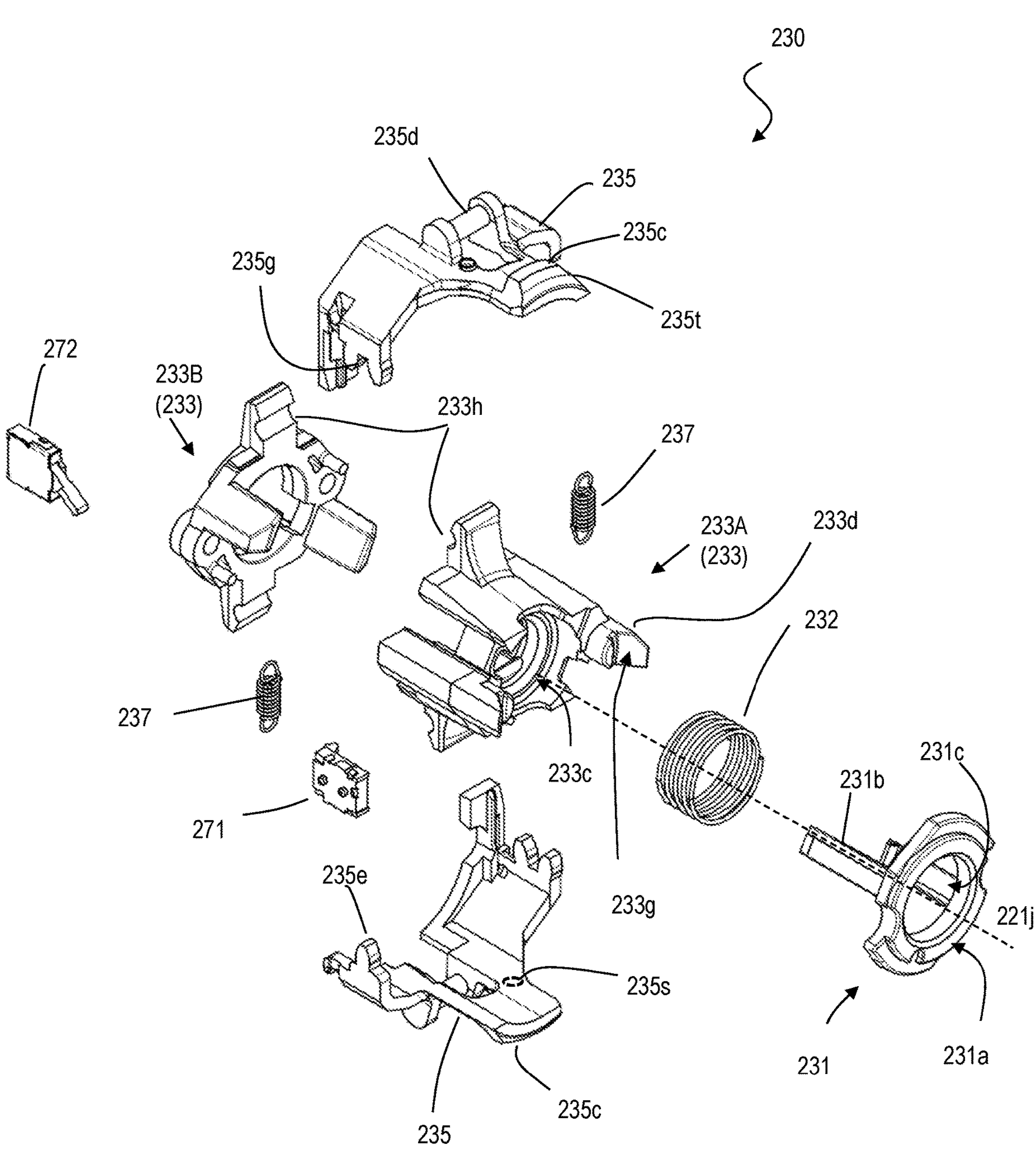
FIG. 16D is an exploded perspective view of the latch unit.

FIG. 16D is an exploded perspective view of the latch unit 230. FIG. 16E is a front view of the latch unit 230 as viewed from the front. The latch unit 230 includes a syringe biasing member 231, a syringe biasing spring 232, a front latch base 233A, a rear latch base 233B, a pair of cartridge latches 235, a pair of cartridge latch springs 237, a cartridge loading detector 271 and a cartridge lock detector 272.

The front latch base 233A and the rear latch base 2338, when combined, form a latch base 233 and support the syringe biasing member 231 and the cartridge latches 235. The latch base 233 has a through hole 233*e* and a pair of arms 233*d* located around the through hole 233*c*. A pair of restricting portions 233*e* are arranged inside the through hole 233*c*. As shown in FIG. 16E, the pair of restricting portions 233*e* are arranged in symmetry with respect to the piston axis 221*j*. Therefore, the through hole 233*c* has the same I-letter shape as the piston 221 in the plane perpendicular to the piston axis 221*j*. The pair of arms 233*d* extend toward the front end, and each arm includes a sleeve contact portion 233*g* at the tip. The sleeve contact portion 233*g* is a slope surface inclined so as to face the inner side (toward the axis 221*j*).

The syringe attachment member 231 includes a ring-shaped contact portion 231*a* with a hole 231*c*, and a pair of legs 231*b* connected to the contact portion 231*a*. The legs 231*b* are inserted into the latch base 233 and are supported by the latch base 233 so that the legs 231*b* are movable in a direction parallel to the piston axis 221*j* of the piston 221. A syringe biasing spring 232 is arranged between the latch base 233 and the syringe attachment member 231, and the syringe biasing spring 232 biases the syringe attachment member 231 in the forward direction. A claw is provided at the tip of the leg 231*b*, which engages the latch base 233, thereby suppressing the syringe-attaching member 231 from being pulled out.

A pair of cartridge latches 235 cover the latch base 233 from outside, each of the cartridge latches 235 having a protrusion 235*c* and a shaft 235*d*. The protrusion 235*c* is located on the front end side of the cartridge latch 235 and is protruding outward. A contact surface 235*t* that is sloped outward is provided on the front end circumferential side of the protrusion 235*c*. The shaft 235*d* extends in a direction perpendicular to the piston axis 221*j* and is located on the outer side relative to the protrusion 235*c*. The latch base 233 has a bearing portion 233*h* that receives the shaft 235*d* of the cartridge latch 235 and supports the shaft 235*d*. Each of the pair of cartridge latches 235 can swing about the corresponding shaft 235*d*.

Hooks at opposite ends of a cartridge latch spring 237 are hooked on the rear ends of the pair of cartridge latches 235. As a result, the rear end of the pair of cartridge latches 235 comes closer inward to the protrusion 235*c*, and the protrusion 235*c* located at the front end is biased outward.

A protrusion 235*e* and a recess 235*g* are provided at opposite ends of the pair of cartridge latches 235 in the circumferential direction adjacent to the cartridge latch spring 237, with the protrusion 235*e* of one cartridge latch 235 loosely mating with the recess 235*g* of the other cartridge latch 235. As will be described below, when the latch unit 230 is inserted into the drug cartridge 100, the cartridge latch spring 237 swings. At this point, as the engagement portions of the protrusion 235*e* and the recess 235*g* function as an axis, the cartridge latch spring 237 expands and contracts stably, and the cartridge latch spring 237 can swing smoothly.

In the latch unit 230, the sleeve contact portion 233*g* of an arm 233*d* contacts the contact surface 152*h* of the engagement claw 152*g* provided on the sleeve 150 of the drug cartridge 100 to disengage the lock of the sleeve 150 of the drug cartridge 100 in the first position and allow the sleeve 150 to move to the second position. On the other hand, the protrusion 235*c* engages with the cassette outer sheath 120 of the drug cartridge 100, and the latch unit 230 grips the drug cartridge 100.

The cartridge latch 235 may be provided with an emergency contact portion 235*s*. When the engagement between the piston unit 286 and the drug cartridge 100 cannot be disengaged for some reason, the protrusions 235*c* of a pair of cartridge latches 235 are moved inward by pressing the contact portion 235*s* from outside. Thus, the engagement between the protrusion 235*c* and the cassette outer sheath 120 of the drug cartridge can be disengaged from outside. In this case, the screw 206 can be removed from the emergency hole 201Bc (FIG. 12A), and an elongated pin can be inserted through the emergency hole 201Bc to push the contact portion 235*s* and swing the pair of cartridge latches 235.

As shown in FIG. 16B, the piston gear 224 has a cylindrical shape with a hole 224*c*, and a female thread is formed in the hole 224*c*. A spur gear is provided on the outer surface of the piston gear 224. The rear end of the piston gear 224 is inserted into the bearing 225, and the piston gear 224 is rotatably supported by the piston case 220 via the bearing 225.

The piston 221 is inserted into the through hole 233*c* of the latch base 233 of the latch unit 230 and the hole 224*c* of the piston gear 224.

The piston 221 inserted into the latch unit 230 and the piston gear 224, when housed in the piston case 220, is restricted from rotating around the piston axis 221*j* due to the restricting surface that is arranged inside the piston case 220 while being in contact with or close to the first flat surface 222*a* of the piston 221.

Reference is made to FIG. 15. When the drive gear 212 of the motor unit 285 rotates, the piston gear 224 (FIG. 16A) meshed with the drive gear 212 rotates. Accordingly, the piston 221 moves forward or moves backward. At this point, while a pair of restricting portions 233*e* protruding in the through hole 233*c* of the latch unit 230 are located at the base portion 221*b*, the first flat surface 222*a* of the piston 221 and the restricting portions 233*e* are close to each other or in contact with each other, and the latch unit 230 does not rotate. While the piston 221 moves backward and the restricting portion 233*e* of the latch unit 230 is located at the tip portion 221*a*, the latch unit 230 rotates around the piston axis 221*j* in accordance with the orientation of the helical surface 222*d*, the second flat surface 222*b*, the helical surface 222*e* and the third flat surface 222*c*.

<Gripping of Drug Cartridge 100 by Piston Unit 286>

Figures 17A, 17B, 17C:
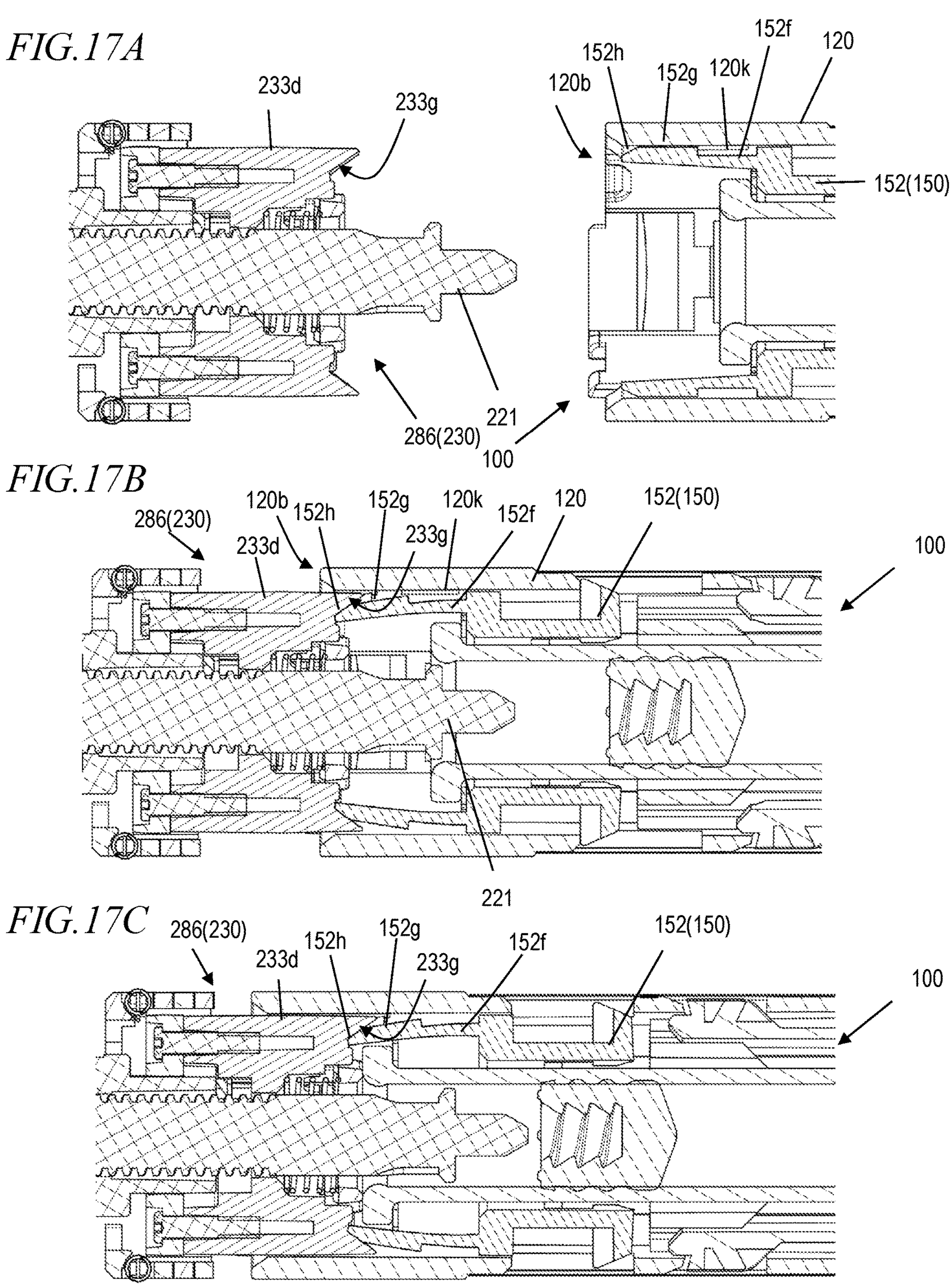
FIG. 17A is a cross-sectional view illustrating the piston unit gripping a drug cartridge.
FIG. 17B is a cross-sectional view illustrating the piston unit gripping a drug cartridge.
FIG. 17C is a cross-sectional view illustrating the piston unit gripping a drug cartridge.

Gripping of the drug cartridge 100 by the piston unit 286 will be described. FIG. 17A to FIG. 17C, FIG. 18A to FIG. 18D and FIG. 19A to FIG. 19C are diagrams illustrating how the piston unit 286 grips the drug cartridge 100. Of these figures, FIG. 17A to FIG. 17C show a cross sectional passing through the arms 233*d* of the latch unit 230, FIG. 18A to FIG. 18D show the outer cassette cylinder 120 of the drug cartridge 100 in cross section, and FIG. 19A to FIG. 19C are diagrams thereof as viewed from the side surface.

Figure 18A:
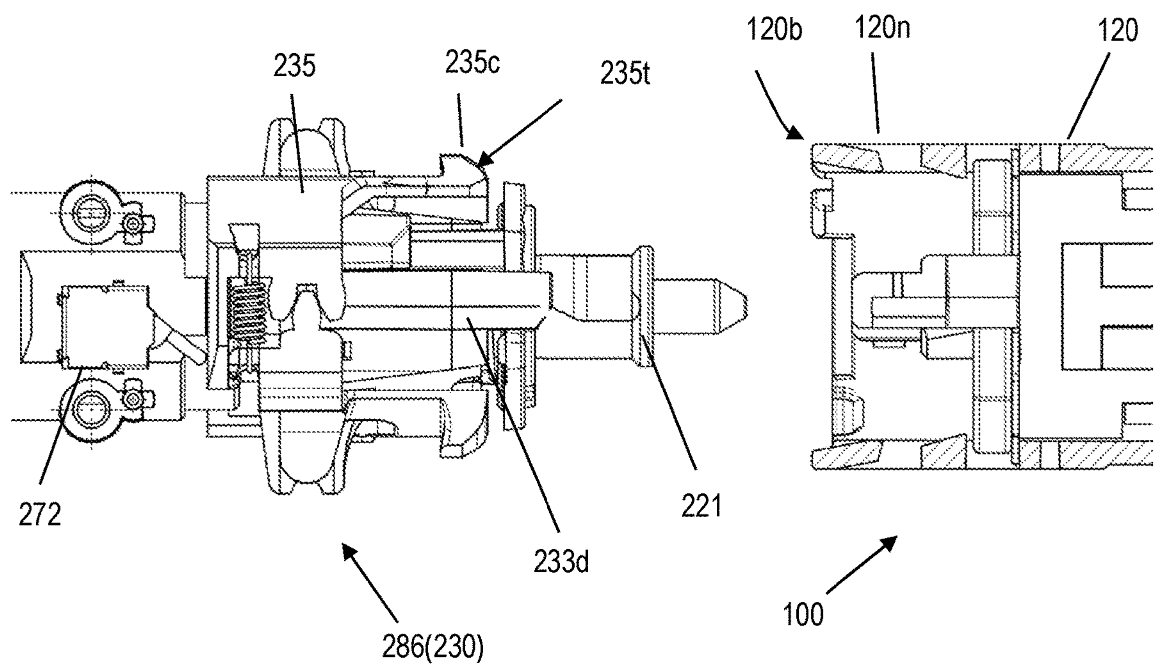
FIG. 18A is a partial cross-sectional view illustrating the piston unit gripping a drug cartridge.
Figure 19A:
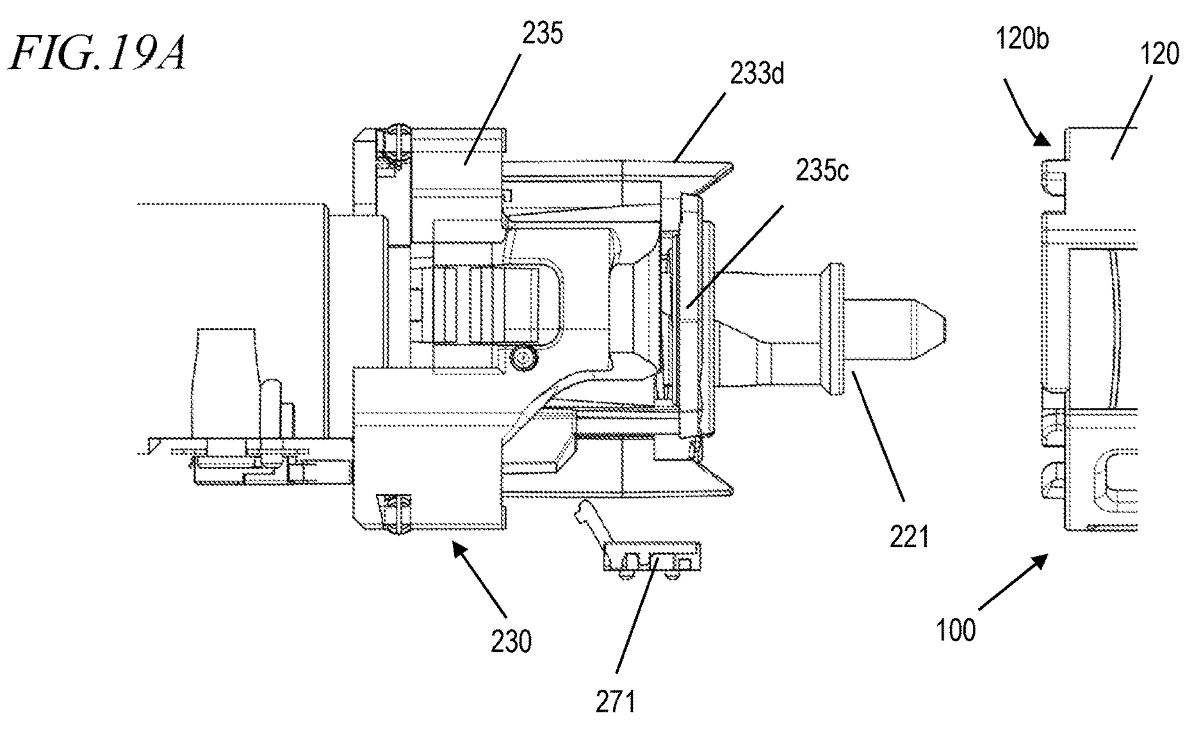
FIG. 19A is a side view illustrating the piston unit gripping a drug cartridge.
Figure 19B:
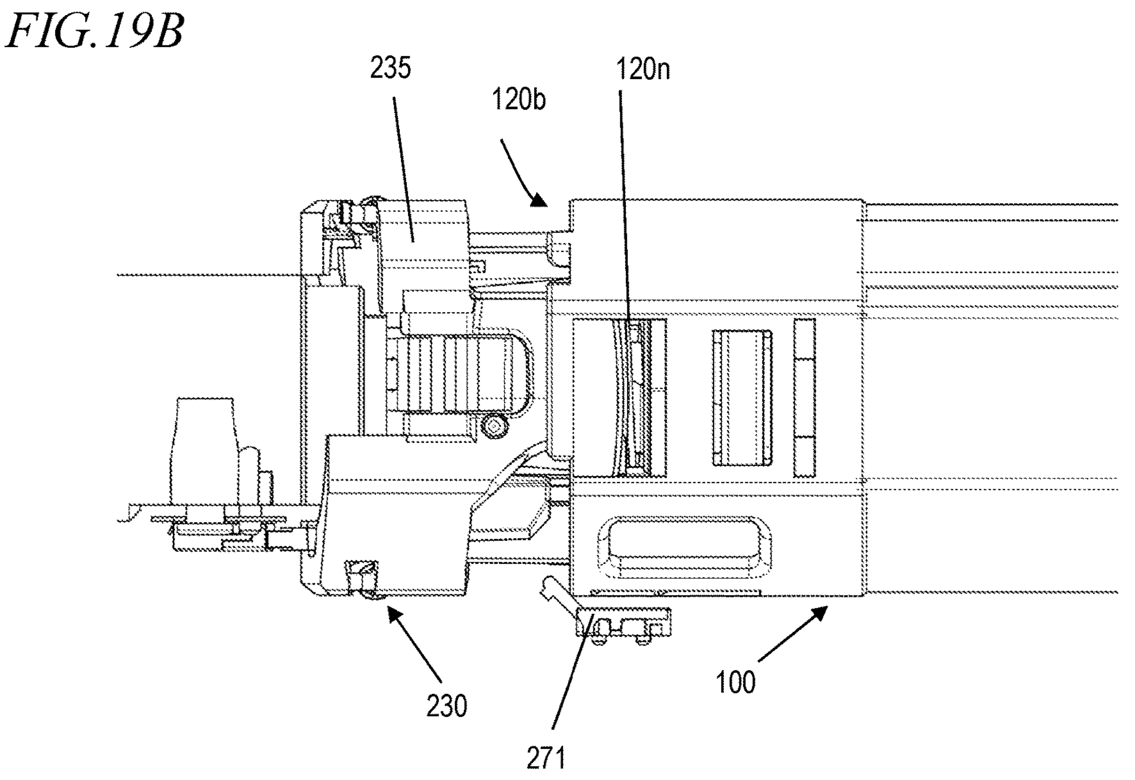
FIG. 19B is a side view illustrating the piston unit gripping a drug cartridge.
Figure 19C:
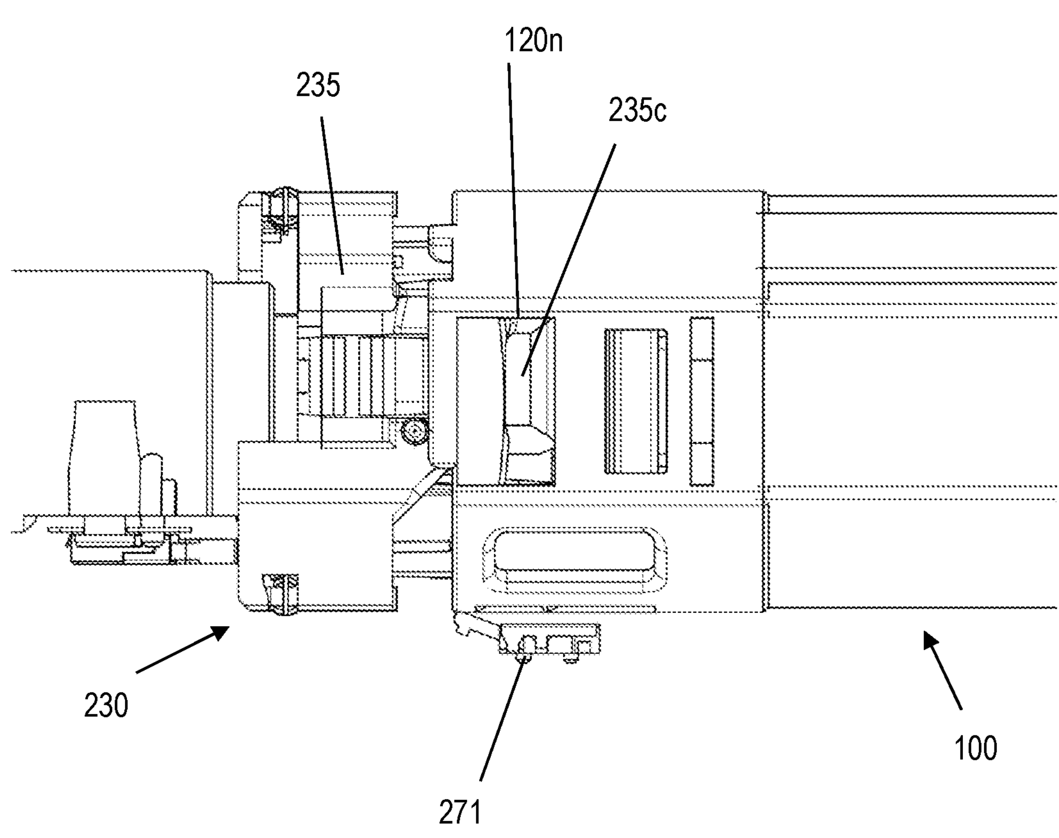
FIG. 19C is a side view illustrating the piston unit gripping a drug cartridge.

When the drug cartridge 100 is inserted through the cartridge opening 201*a* of the drug injection device 200 (FIG. 1A, FIG. 1B), as shown in FIG. 17A, FIG. 18A, FIG. 19A, the cassette rear opening 120*b* of the cassette outer sheath 120 of the drug cartridge 100 comes close to the piston unit 286. Since the cartridge loading detector 271 and the drug cartridge 100 are separated from each other, the cartridge loading detector 271 is not detecting the drug cartridge 100 (OFF state, FIG. 19A). Since the cartridge latch 235 is not pivoting, the cartridge lock detector 272 is also not detecting the pivoting of the cartridge latch 235 (OFF state, FIG. 18A).

Figure 18B:
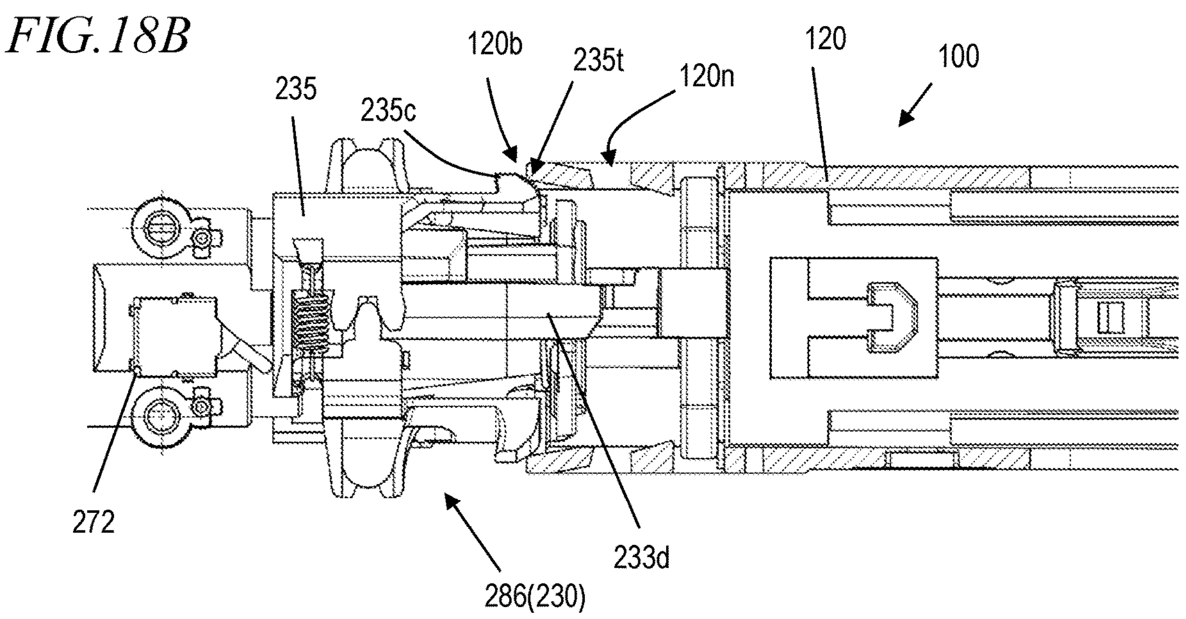
FIG. 18B is a partial cross-sectional view illustrating the piston unit gripping a drug cartridge.

As shown in FIG. 17B and FIG. 18B, insertion of the drug cartridge 100 into the drug injection device 200 proceeds, and the tip of the piston unit 286 is inserted into the cassette outer sheath 120 through the cassette rear opening 120*b* of the cassette outer sheath 120 of the drug cartridge 100. The sleeve contact portion 233*g* of an arm 233*d* of the piston unit 286 contacts the contact surface 152*h* of the engagement claw 152*g* located in the vicinity of the sleeve rear opening 152*b* of the sleeve 150, and the elastic support portion 152*f* flexes inward. Thus, the engagement between the sleeve engagement portion 120*k* of the cassette outer sheath 120 and the engagement claw 152*g* is disengaged.

When the drug cartridge 100 is further inserted into the drug injection device 200, the piston unit 286 relatively moves toward the front end of the drug cartridge 100, and the sleeve 150 is also pushed by the piston unit 286 to move toward the front end. At this point, as shown in FIG. 18B, the protrusion 235*c* of the latch unit 230 is not inserted into the cassette outer sheath 120. The cartridge loading detector 271 and the cartridge lock detector 272 remain OFF.

Figure 18C:
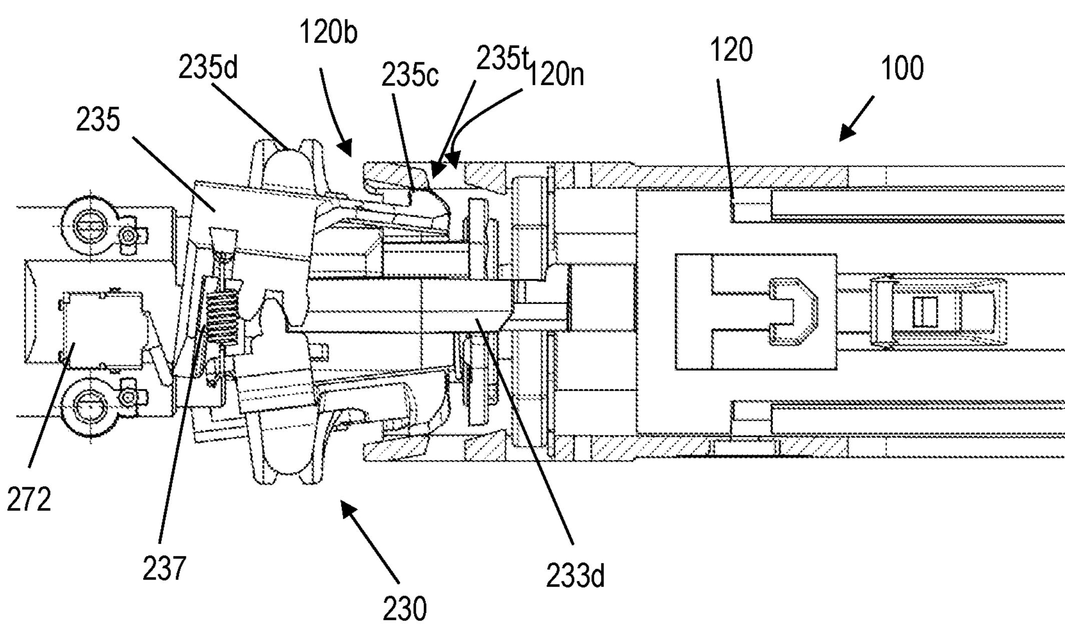
FIG. 18C is a partial cross-sectional view illustrating the piston unit gripping a drug cartridge.

As the drug cartridge 100 is further inserted into the drug injection device 200, the contact surface 235*t* of the protrusion 235*c* contacts the inner edge of the cassette rear opening 120*b*, causing the cartridge latch 235 to rotate inward about the shaft 235*d* against the biasing force of the cartridge latch spring 237. Thus, the protrusion 235*c* is inserted into the cassette outer sheath 120 through the cassette rear opening 120*b*, as shown in FIG. 18C. The cartridge lock detector 272 is turned ON by detecting the pivoting of the cartridge latch 235. As shown in FIG. 19B, at this point, the cartridge loading detector 271 remains OFF.

Figure 18D:
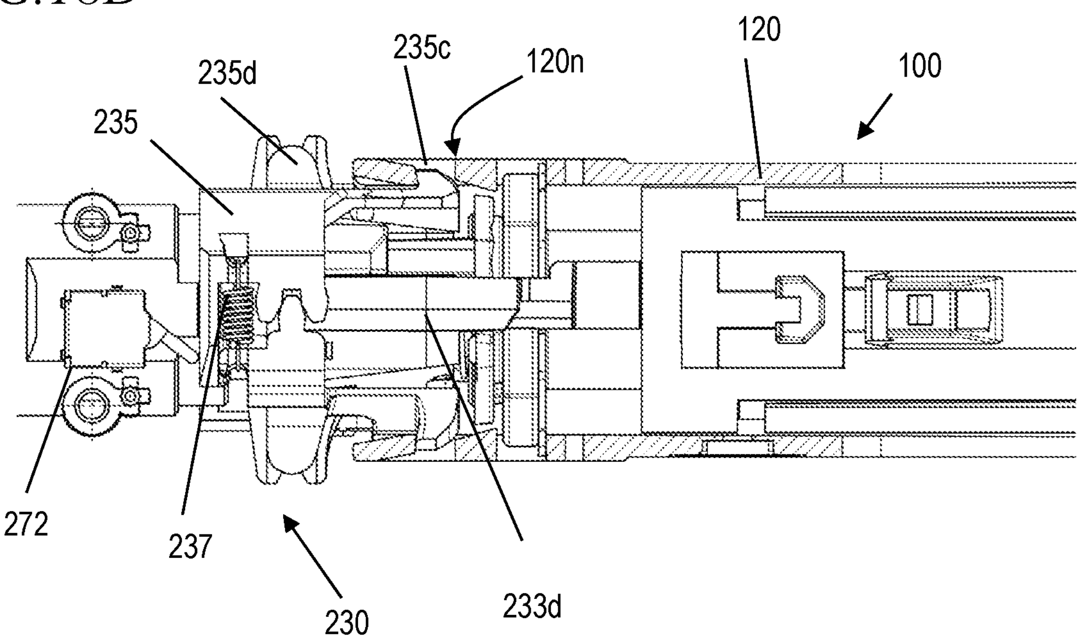
FIG. 18D is a partial cross-sectional view illustrating the piston unit gripping a drug cartridge.

As the drug cartridge 100 is further inserted into the drug injection device 200, the protrusion 235*c* engages with the piston unit engagement portion 120*n*, as shown in FIG. 18D. At this point, the cartridge latch 235 rotates outward about the shaft 235*d* by the biasing force of the cartridge latch spring 237. Thus, the cartridge lock detector 272 is turned OFF.

The protrusion 235*c* of the cartridge latch 235 engages with the piston unit engagement portion 120*n*, thereby completing the gripping of the drug cartridge 100 by the piston unit 286, and completing the loading of the drug cartridge 100 into the drug injection device 200. Since the protrusion 235*c* of the cartridge latch 235 is biased outward by the cartridge latch spring 237, the protrusion 235*c* remains inserted in the piston unit engagement portion 120*n*, which is an opening. That is, the piston unit 286 is locked while gripping the drug cartridge 100. As shown in FIG. 19C, at this point, the cartridge loading detector 271 detects complete loading of the drug cartridge 100 to be turned ON.

On the other hand, as shown in FIG. 17C, the arms 233*d* of the piston unit 286 move the sleeve 150 to the second position in the drug cartridge 100 while being in contact with the engagement claw 152*g* of the sleeve 150. Thus, when the loading of the drug cartridge 100 into the drug injection device 200 is complete, the cap 110 is in the unlocked state where it can be detached from the cassette outer sheath 120.

The outputs of the cartridge loading detector 271 and the cartridge lock detector 272 when loading the drug cartridge 100 into the drug injection device 200 are shown in the following table.

TABLE 2

| | Cartridge loading detector 271 | Cartridge lock detector 272 |
|---|---|---|
| Before loading | OFF | OFF |
| During loading | OFF | OFF |
| | OFF | ON |
| | ON | ON |
| Loading complete | ON | OFF |

Thus, by the cartridge loading detector 271 detecting that the cartridge is in the correct position at completion of loading and the cartridge lock detector 272 detecting that the latch unit 230 has operated, it is possible to correctly detect the loading of the drug cartridge 100 and the gripping of the drug cartridge 100 by the piston unit 286.

<Releasing Drug Cartridge 100 by Piston Unit 286>

Figure 20A:
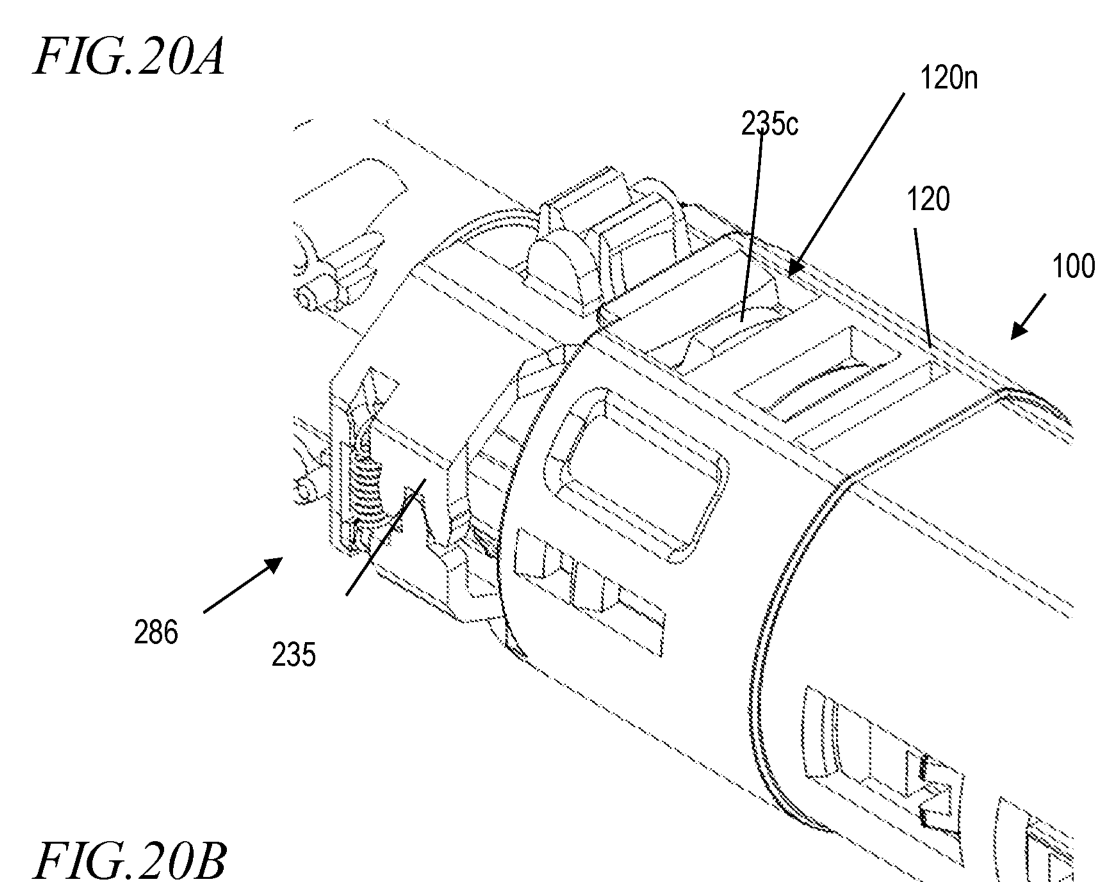
FIG. 20A is a perspective view showing the vicinity of the engagement portion between the piston unit and the drug cartridge when the drug cartridge is released by the piston unit.
Figure 20B:
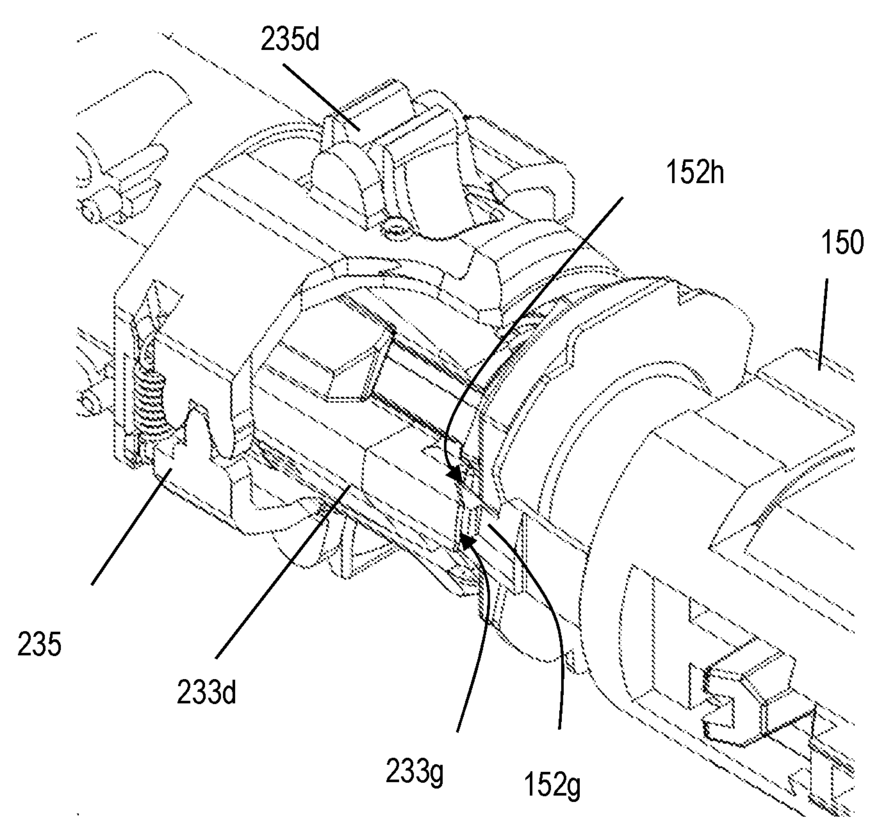
FIG. 20B is a perspective view showing the vicinity of the engagement portion between the piston unit and the drug cartridge when the drug cartridge is released by the piston unit.
Figure 21A:
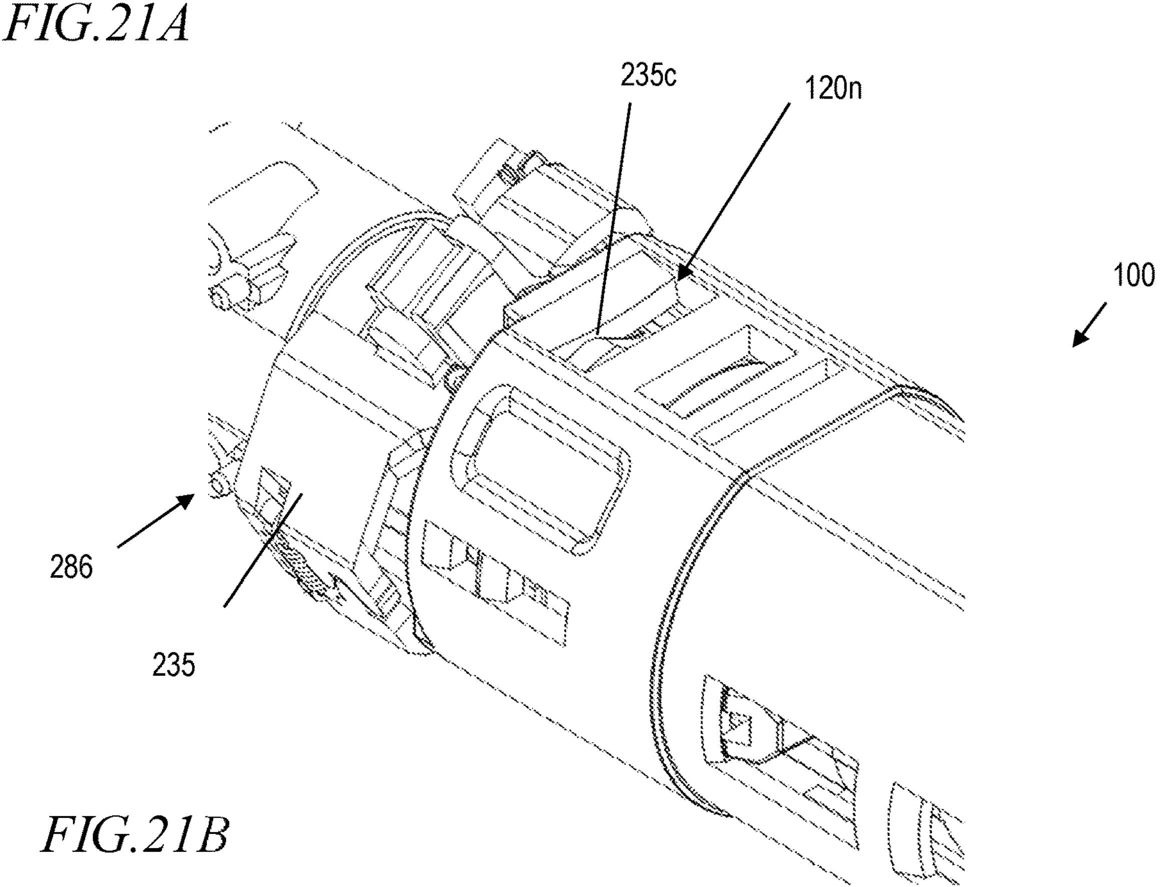
FIG. 21A is a perspective view showing the vicinity of the engagement portion between the piston unit and the drug cartridge when the drug cartridge is released by the piston unit.
Figure 21B:
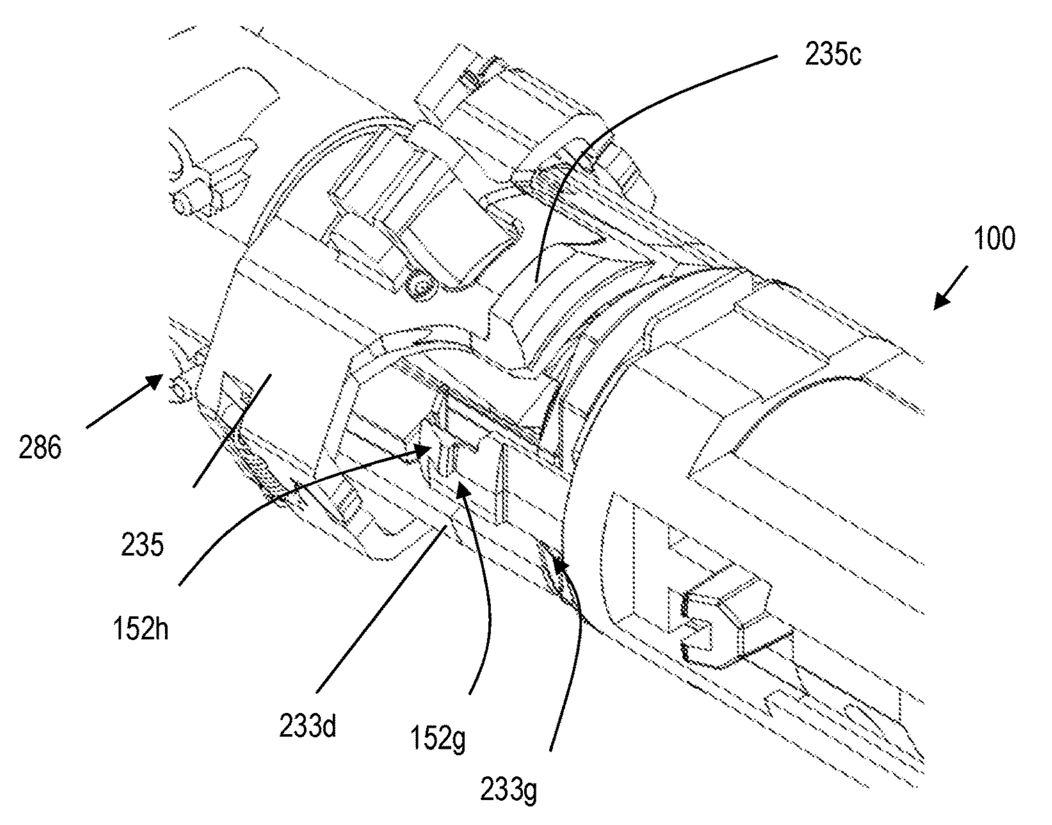
FIG. 21B is a perspective view showing the vicinity of the engagement portion between the piston unit and the drug cartridge when the drug cartridge is released by the piston unit.
Figures 22A, 22B:
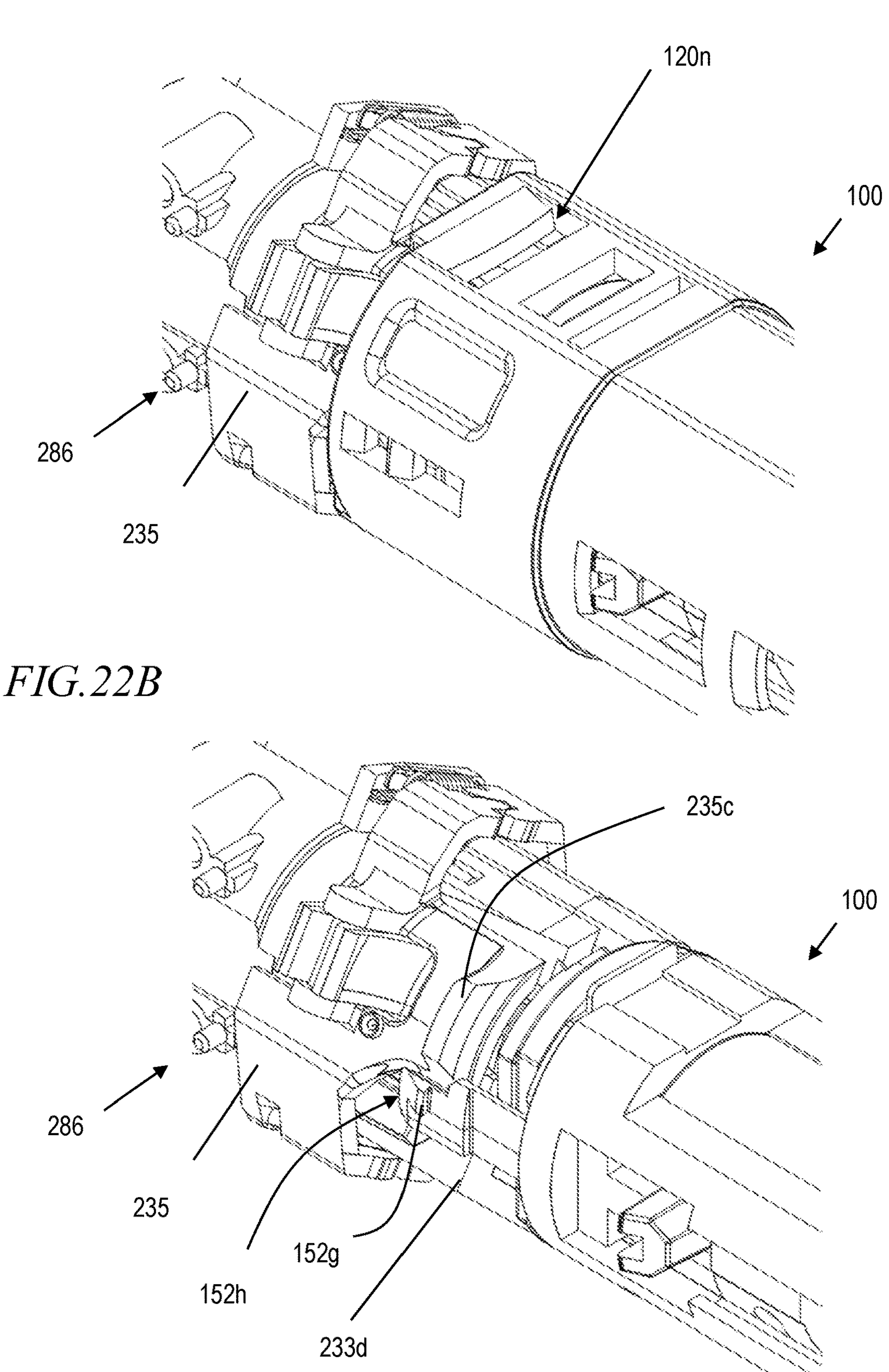
FIG. 22A is a perspective view showing the vicinity of the engagement portion between the piston unit and the drug cartridge when the drug cartridge is released by the piston unit.
FIG. 22B is a perspective view showing the vicinity of the engagement portion between the piston unit and the drug cartridge when the drug cartridge is released by the piston unit.

Release of the drug cartridge 100 by the piston unit 286 will be described. When the injection of the drug, i.e., injection, is completed, the piston unit 286 moves backward to remove the needle, and then the piston 221 moves backward causing the piston unit 286 to release the drug cartridge 100. FIG. 20A, FIG. 21A and FIG. 22A are perspective views showing the vicinity of the engaging portion between the piston unit 286 and the drug cartridge 100 at the time of releasing the drug cartridge 100 by the piston unit 286. FIG. 20B, FIG. 21B and FIG. 22B, corresponding to FIG. 20A, FIG. 21A and FIG. 22A, respectively, are perspective views of the drug cartridge 100 with the cassette outer sheath 120 removed.

FIG. 20A and FIG. 20B show the state where the piston unit 286 is gripping the drug cartridge 100. The sleeve contact portion 233*g* of the arm 233*d* of the piston unit 286 is in contact with the contact surface 152*h* of the engagement claw 152*g* of the sleeve 150, and the elastic support portion 152*f* is flexed inward. The protrusion 235*c* of the cartridge latch 235 is inserted into the piston unit engagement portion 120*n*, which is an opening.

Release of the drug cartridge 100 from this state is performed as the piston 221 moves backward to the needle guard ejection position and the cartridge ejection position to rotate the latch unit 230 around the piston axis 221*j*. As shown in FIG. 16B, FIG. 16C and FIG. 16E, the piston 221 has an I-shaped cross section, and is twisted over the tip portion 221*a*. As the piston 221 moves backward and the tip portion 221*a* passes through the through hole 233*c* of the latch base 233, the latch unit 230 rotates counterclockwise as viewed from the tip side in accordance with the orientations of the helical surface 222*d*, the second flat surface 222*b*, the helical surface 222*e* and the third flat surface 222*c*.

In a state where the restricting portion 233*e* located in the through hole 233*c* of the latch base 233 is close to or in contact with the second flat surface 222*b*, i.e., in a state where the piston 221 has moved backward to the needle guard ejection position, first, the contact between the sleeve contact portion 233*g* of the arm 233*d* of the piston unit 286 and the contact surface 152*h* of the elastic support portion 152*f* of the engagement claw 152*g* of the sleeve 150 is disengaged. Thus, the sleeve 150 is allowed to move backward, and as described with reference to FIG. 9D, the sleeve 150 moves backward by the biasing force of the cassette spring 140 and moves from the second position to the first position. FIG. 21A and FIG. 218 show the state after the sleeve 150 moves backward. At this point, the protrusion 235*c* of the cartridge latch 235 also rotates counterclockwise as viewed from the tip, but a part of the protrusion 235*c* is still located within the opening of the piston unit engagement portion 120*n*. Thus, the drug cartridge 100 is gripped by the piston unit 286.

In a state where the latch unit 230 further rotates and the restricting portion 233*e* located in the through hole 233*c* of the latch base 233 is close to or in contact with the third flat surface 222*c* (FIG. 16B, FIG. 16C, FIG. 16E), i.e., a state where the piston has moved backward to the cartridge ejection position, the protrusion 235*c* of the cartridge latch 235 detaches from the opening of the piston unit engagement portion 120*n* as shown in FIG. 22A and FIG. 22B. Thus, the drug cartridge 100 is released from the piston unit 286. That is, the drug cartridge 100 becomes unlocked and the operator can eject the drug cartridge 100, specifically, pick and remove the drug cartridge 100 from the drug injection device 200.

<Operation of Driver Device 284>

Referring to FIG. 23A to FIG. 23F, the operation of the driver device 284 will now be described. FIG. 23A to FIG. 23F are perspective views of the driver device 284. For ease of understanding, the piston case 220 is not shown in these figures. After the drug cartridge 100 is gripped by the piston unit 286 through the operation described above, the driver device 284 operates as follows.

Figure 23A:
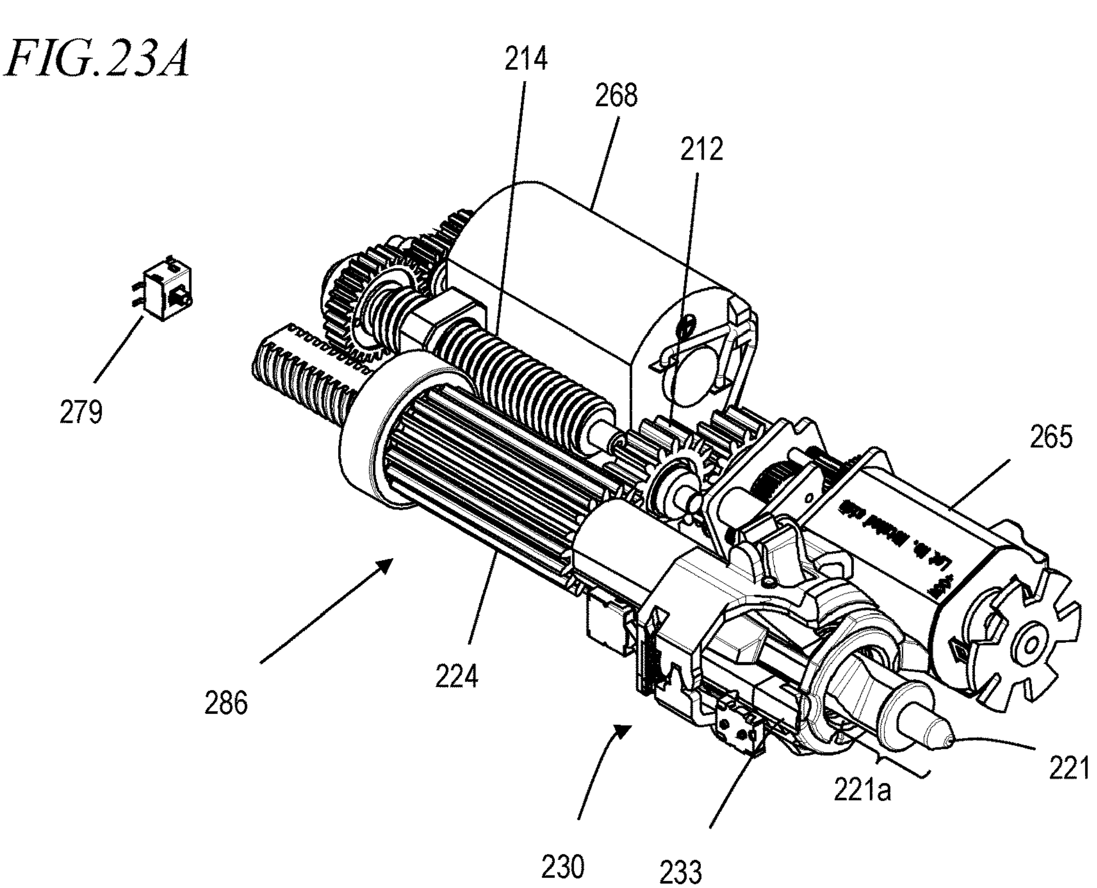
FIG. 23A is a perspective view of the driver device.

1. Initial State (FIG. 23A)

In the initial state where the drug cartridge 100 is loaded into the drug injection device 200, the tip portion 221*a* of the piston 221 is in a position further forward than the latch base 233 of the latch unit 230.

Figure 23B:
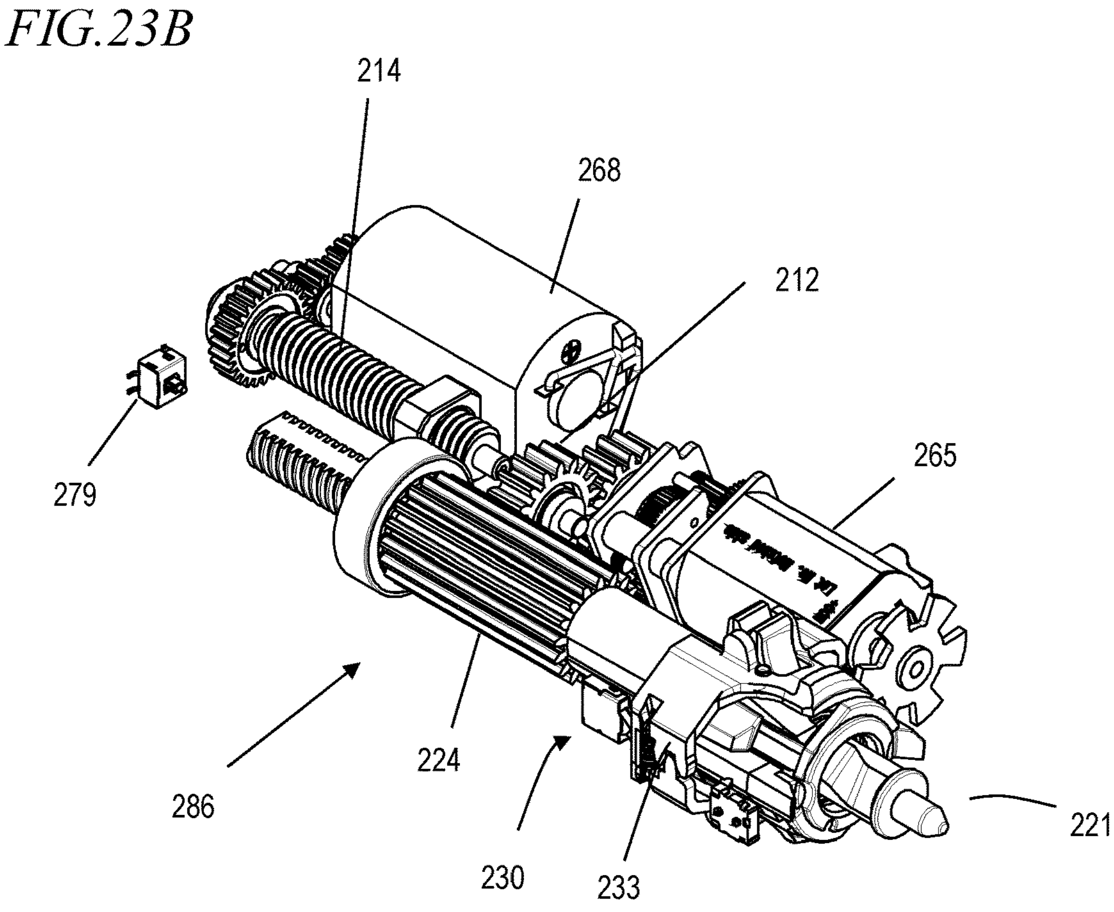
FIG. 23B is a perspective view of the driver device.

2. Needle Insertion (FIG. 23B)

When the operator presses the injection button 254, the needle insertion/removal motor 268 rotates the drive screw 214. Thus, the piston unit 286 moves forward. Since the tooth width of the spur gear of the piston gear 224 is wide, the drive gear 212 and the piston gear 224 remain meshed with each other even when the piston unit 286 moves forward.

Figures 23C, 23D:
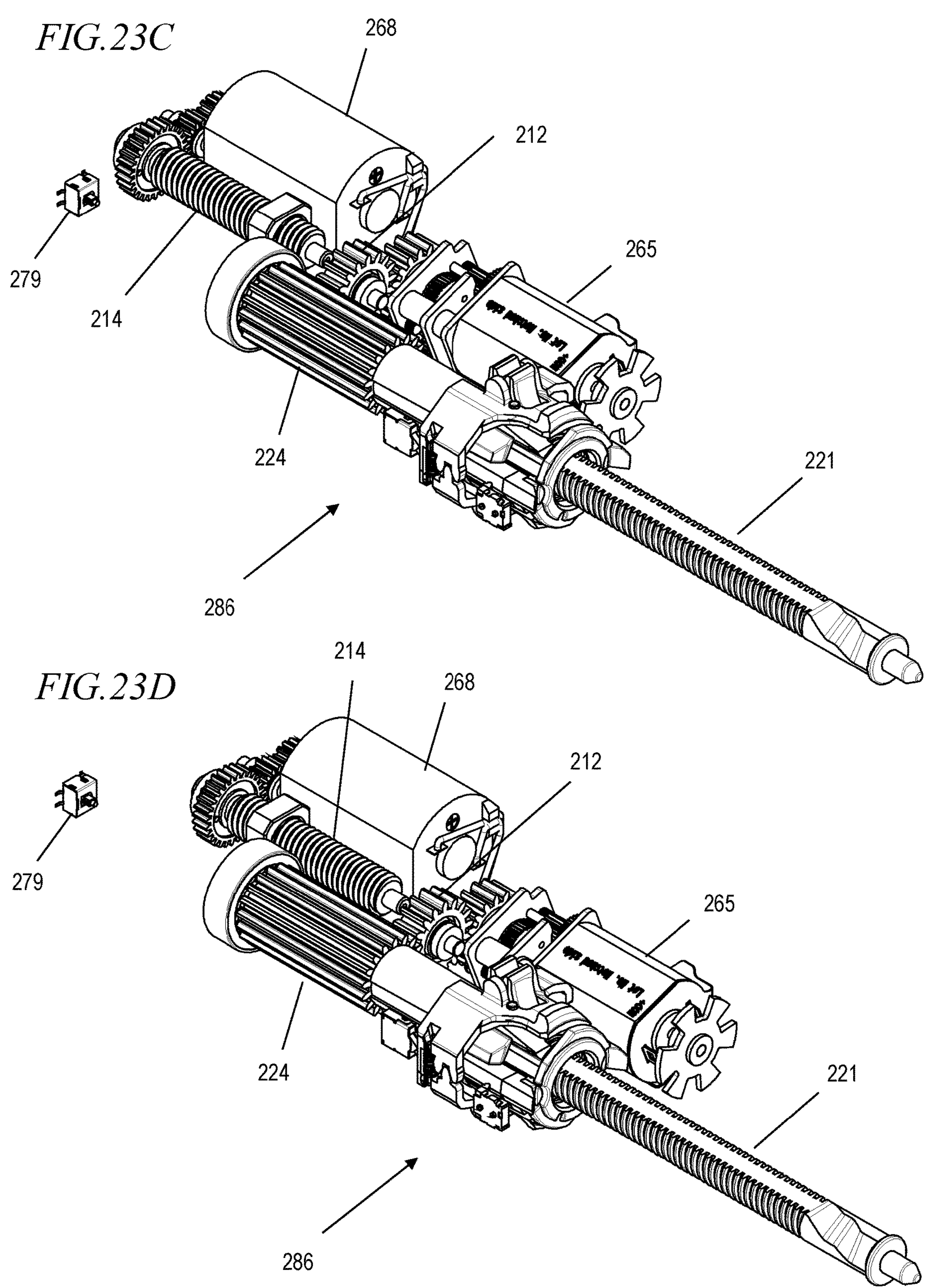
FIG. 23C is a perspective view of the driver device.
FIG. 23D is a perspective view of the driver device.

3. Drug Injection (FIG. 23C)

The injection motor 265 rotates the drive gear 212, and the piston gear 224, which is meshed with the drive gear 212 rotates. Thus, the piston 221 moves forward, and the piston 221 causes the stopper 13 (FIG. 2) of the pre-filled syringe to move forward. This allows the drug to be administered to the operator.

4. Needle Removal (FIG. 23D)

By causing the needle insertion/removal motor 268 to reverse in the state where the piston 221 has moved forward, the drive screw 214 also reverses, and the piston unit 286 moves backward. The drive gear 212 and piston gear 224 remain meshed with each other.

Figure 23E:
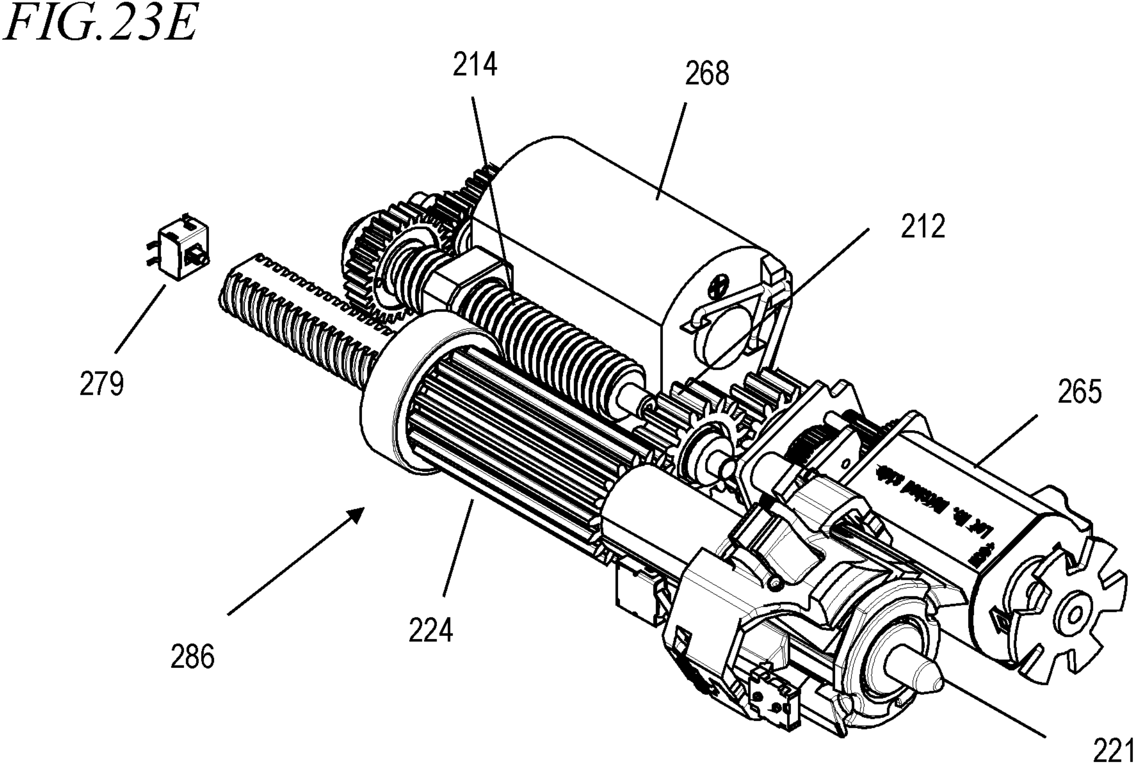
FIG. 23E is a perspective view of the driver device.

5. Sleeve Block Disengagement (FIG. 23E)

The injection motor 265 reverses the drive gear 212, and the piston gear 224, which is meshed with the drive gear 212, also reverses. This causes the piston 221 to move backward to the needle guard ejection position. As the tip portion 221*a* of the piston 221 passes through the through hole 233*c* of the latch base 233, the latch unit 230 rotates counterclockwise by an angle of $\alpha 1$ as viewed from the tip side. In the state shown in FIG. 23E, the second flat surface 222*b* close to or in contact with the restricting portion 233*e*, which is located in the through hole 233*c* of the latch base 233, and the contact between the sleeve contact portion 233*g* of the arm 233*d* of the piston unit 286 and the contact surface 152*h* of the elastic support portion 152*f* of the engagement claw 152*g* of the sleeve 150 is disengaged. As described above, in the drug cartridge 100, the sleeve 150 moves from the second position to the first position, and the needle guard 130 is ejected. Detection of the ejection of the needle guard 130 is done by the needle guard detector 276.

Figure 23F:
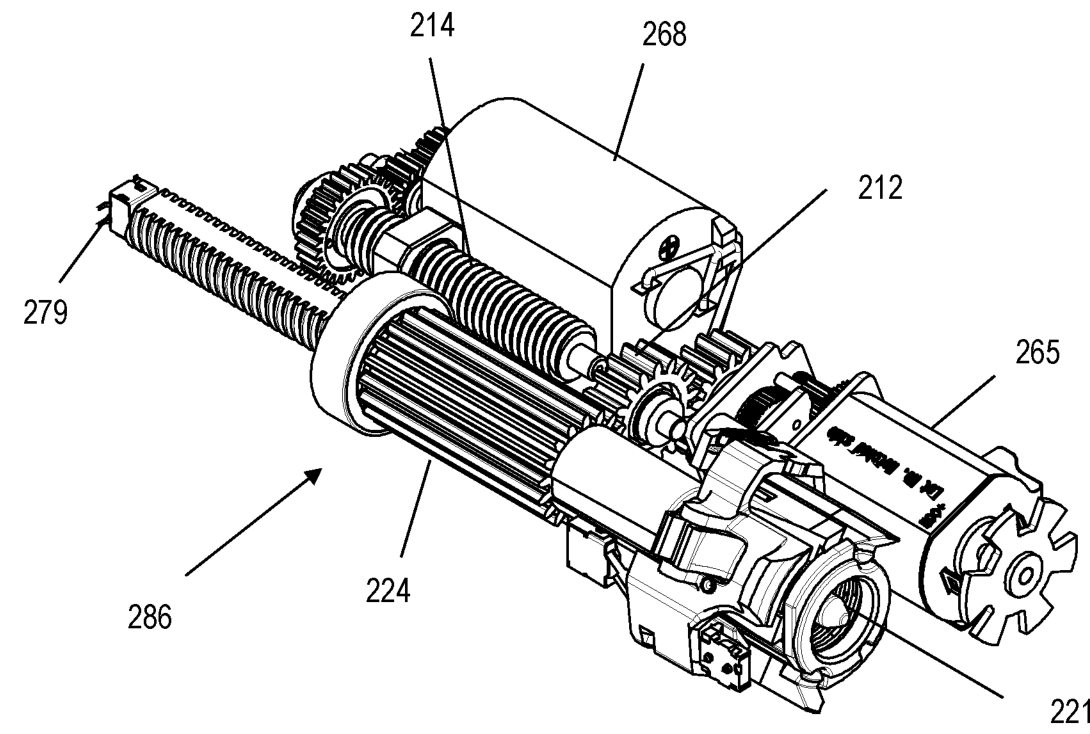
FIG. 23F is a perspective view of the driver device.

6. Unlatching (FIG. 23F)

The piston 221 further moves backward to the cartridge ejection position, and the latch unit 230 also further rotates counterclockwise by an angle of $(\alpha 2-\alpha 1)$. That is, the latch unit 230 has rotated by an angle of $\alpha 2$ from its initial state. The third flat surface 222*c* comes close to or into contact with the restricting portion 233*e* located in the through hole 233*c* of the latch base 233, and the protrusion 235*c* of the cartridge latch 235 is detached from the opening of the piston unit engagement portion 120n. Thus, the drug cartridge 100 is released from the piston unit 286. In this state, the rear end of the piston 221 presses down the origin detector 279, and the origin detector 279 detects that the piston 221 has moved backward to the origin position. Based on the output of the origin detector 279, the injection motor 265 stops and the piston 221 also stops moving backward.

7. Return to Initial Position (FIG. 23A)

After the drug cartridge 100 is removed, the injection motor 265 causes the drive gear 212 to rotate forward, and the piston gear 224, which is engaged with the drive gear 212, also rotates forward. Thus, as shown in FIG. 23A, the piston 221 moves forward to the initial position. The initial position is determined by a predetermined amount of movement based on the pulse output of the rotary encoder, using the position stopped by the origin detector 279 as the origin.

Thus, with the driver device of the present embodiment, by releasing the drug cartridge after ejection of the needle guard, it is possible to control the driver device so that the drug cartridge can be removed only when the ejection of the needle guard is confirmed. Thus, it is possible to treat the drug cartridge loaded in the drug injection device more safely.

<Other Structures>

<Slider Unit 288>

Referring to FIG. 24A to FIG. 24E, the structure and operation of the slider unit 288 will be described. The slider unit 288 biases the drug cartridge 100 inserted into the drug injection device 200 in the direction of ejection (forward). The slider unit 288 includes a slide member 241 adjacent to the cartridge space 280a and supported by the lower casing 280B (FIG. 13) so that it can move in the direction in which the cartridge space 280a extends, and a biasing member 242 that biases the slide member toward the front end of the drug injection device 200. In the present embodiment, the biasing member 242 is a torsion spring. The slide member 241 includes an engagement projection 241c on the rear end side.

As shown in FIG. 24A, before loading the drug cartridge 100 into the drug injection device 200, the biasing member 242 is biasing the slide member 241 toward the front end side. When the drug cartridge 100 is inserted through the cartridge opening 201a of the drug injection device 200, the rear end of the cassette outer sheath 120 of the drug cartridge 100 engages with the engagement projection 241c, as shown in FIG. 24B. As the drug cartridge 100 is further inserted, the slide member 241 moves together with the drug cartridge 100 toward the rear end side, against the biasing force of the biasing member 242.

Figure 24C:
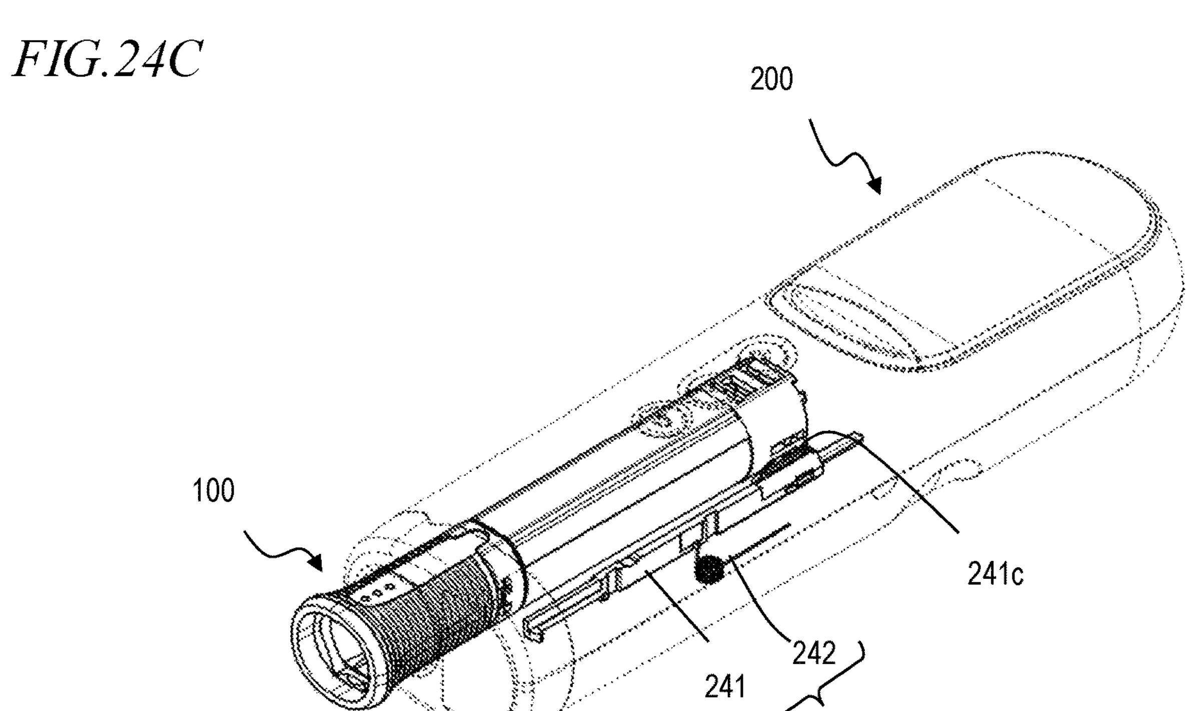
FIG. 24C is a perspective view illustrating the operation of the slider unit.

As shown in FIG. 24C, when the drug cartridge 100 is further inserted, the piston unit 286 grips the drug cartridge 100 and the loading of the drug cartridge 100 is completed. In this state, the slide member 241 is biased in the front end direction by the biasing member 242, but the drug cartridge 100 does not move because of the gripping by the piston unit 286.

Figure 24D:
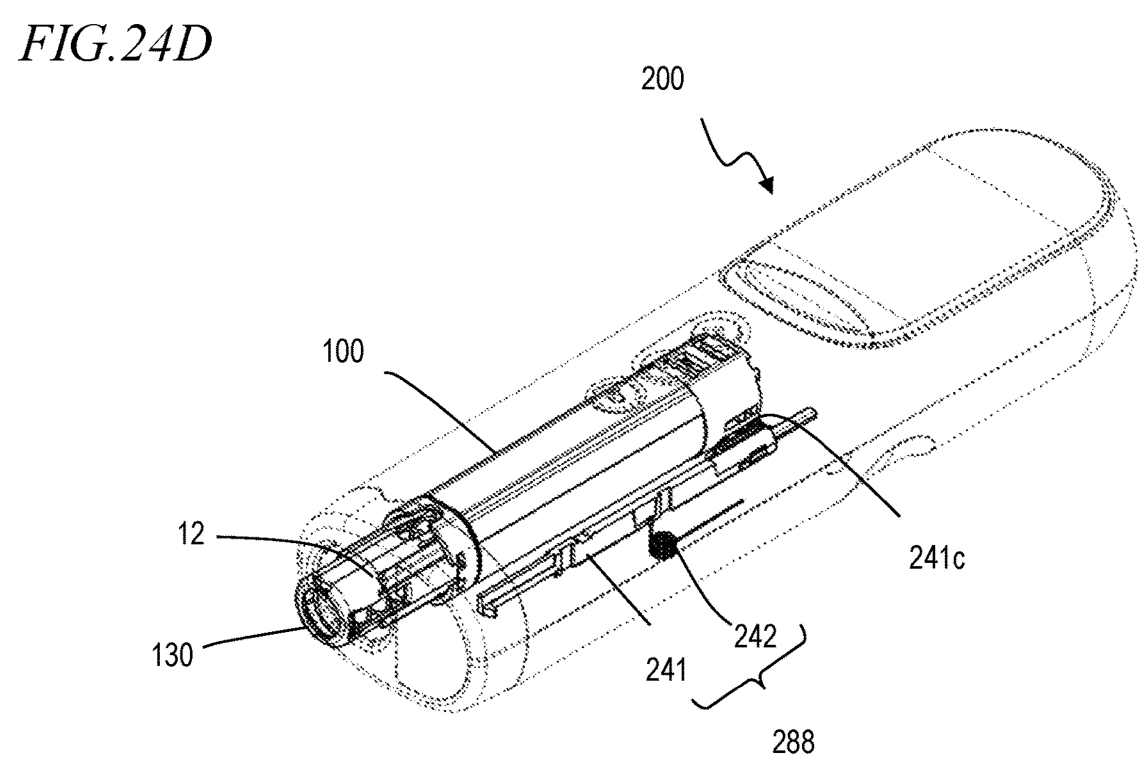
FIG. 24D is a perspective view illustrating the operation of the slider unit.

As described above, when the injection is completed and the latch unit 230 rotates, the contact between the arm 233d of the piston unit 286 and the engagement claw 152g of the sleeve 150 is disengaged, and the sleeve 150 moves to the first position. Thus, the needle guard 130 protrudes and covers the injection needle 12, as shown in FIG. 24D.

Figure 24E:
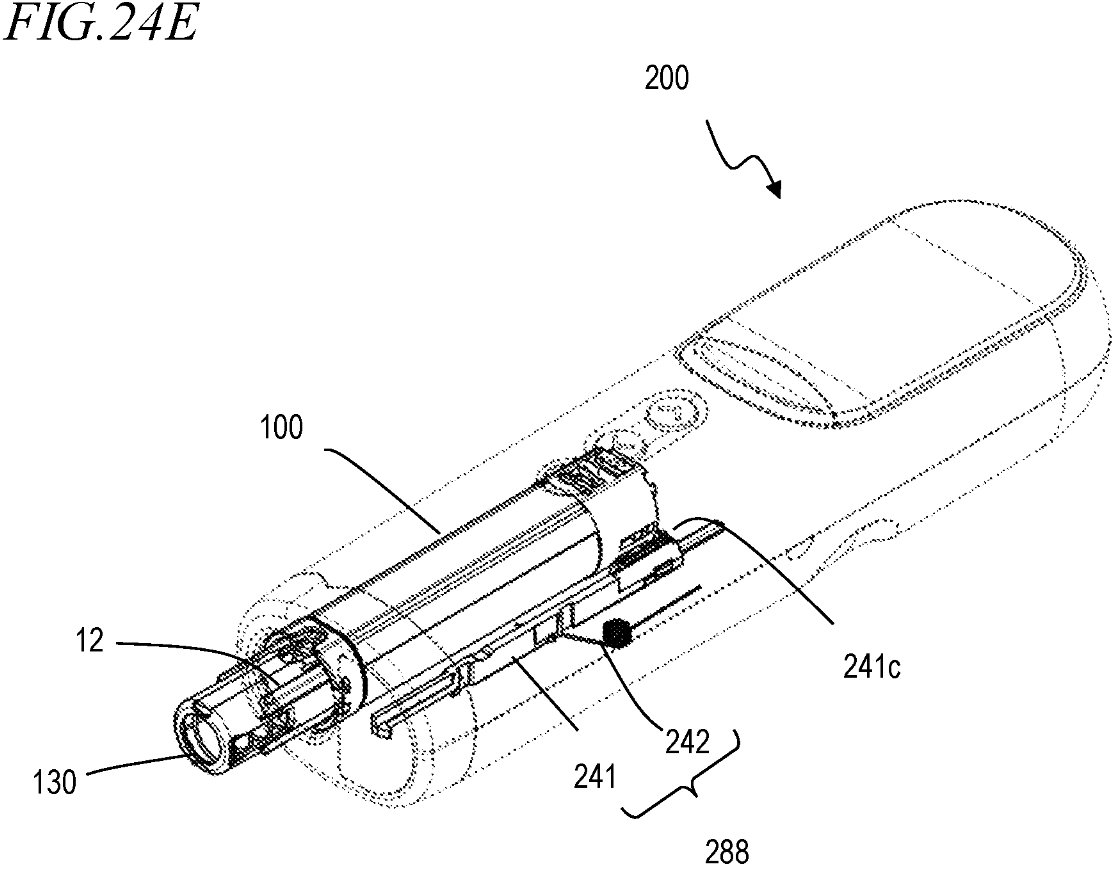
FIG. 24E is a perspective view illustrating the operation of the slider unit.

When the latch unit further rotates to disengage the engagement between the protrusion 235c of the cartridge latch 235 and the cassette outer sheath 120 of the drug cartridge 100, the drug cartridge 100 moves forward together with the slide member 241, which is biased toward the front end by the biasing member 242. As shown in FIG. 24E, the needle guard 130 of the drug cartridge 100 protrudes significantly from the cartridge opening 201a of the drug injection device 200, making it easier for the operator to pick and pull out the drug cartridge 100.

<Needle Insertion Completion Detector 277 and Needle Removal Completion Detector 278>

Figure 25A:
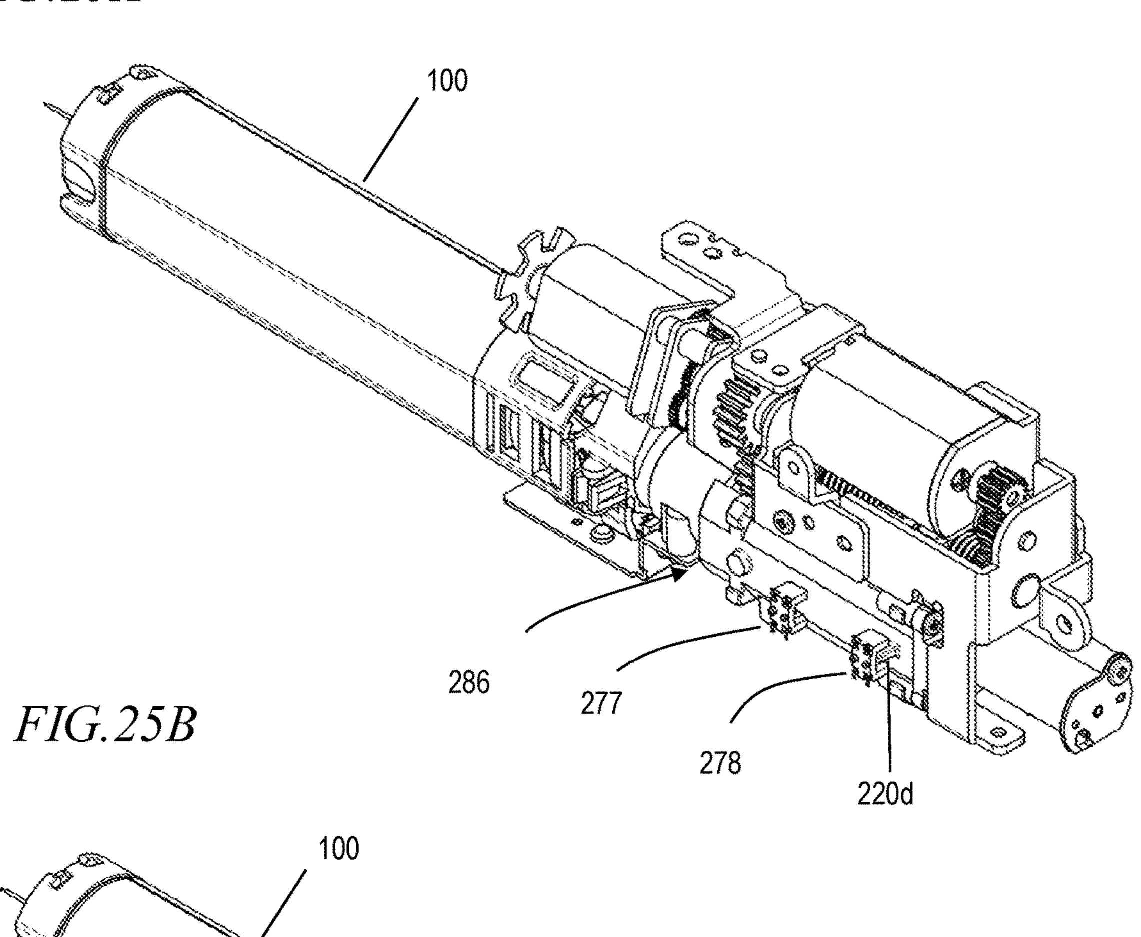
FIG. 25A is a perspective view illustrating the needle insertion completion detector and the needle removal completion detector.
Figure 25B:
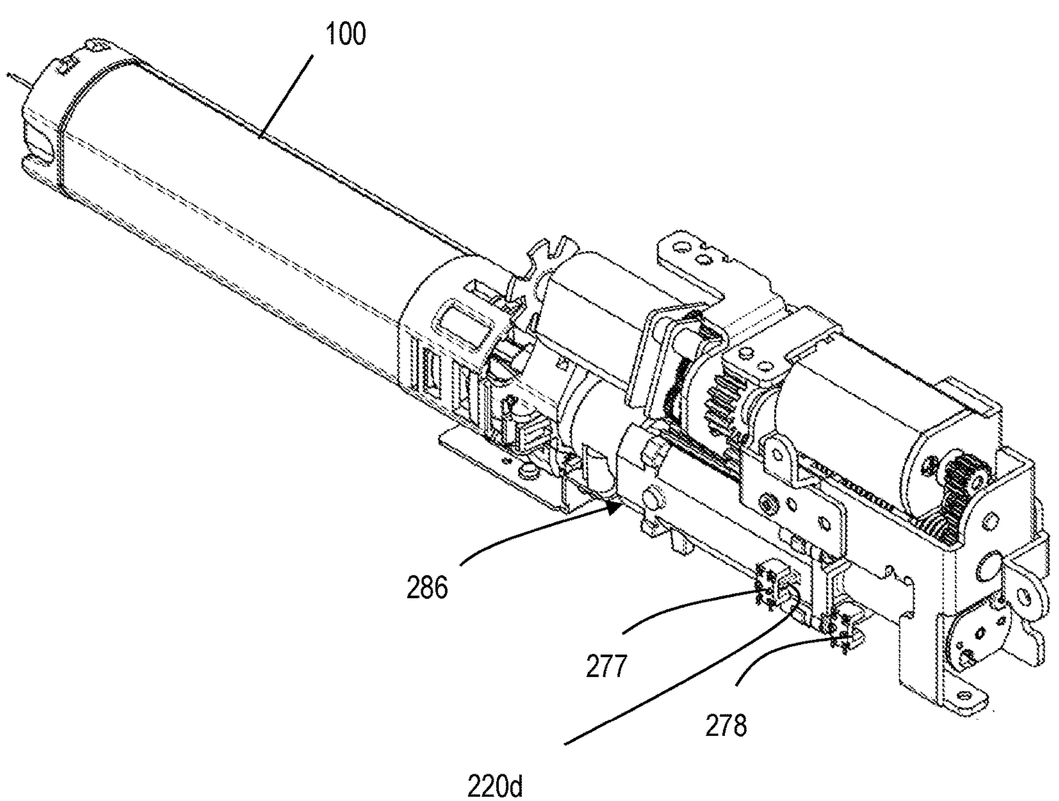
FIG. 25B is a perspective view illustrating the needle insertion completion detector and the needle removal completion detector.

FIG. 25A and FIG. 25B are perspective views of the driver device 284 with the piston unit 286 gripping the drug cartridge 100. The piston case 220 of the piston unit 286 includes a light-blocking portion 220d. The needle insertion completion detector 227 and the needle removal completion detector 278 are, for example, photo interrupters. The needle removal completion detector 278 detects the light-blocking portion 220d at the initial position of the drug cartridge 100, i.e., at the position where the drug cartridge 100 has been loaded into the drug injection device 200. The needle insertion completion detector 227 detects the light-blocking portion 220d at the position where the piston unit 286 has moved forward and the needle insertion is complete.

<Needle Guard Detector 276>

Figure 26A:
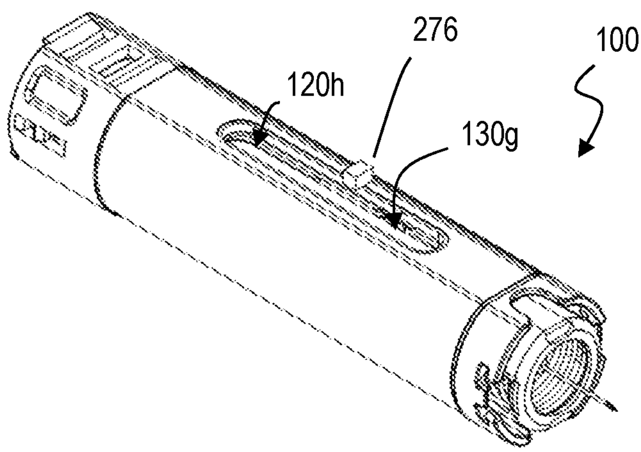
FIG. 26A is a perspective view illustrating the needle guard detector.
Figure 26B:
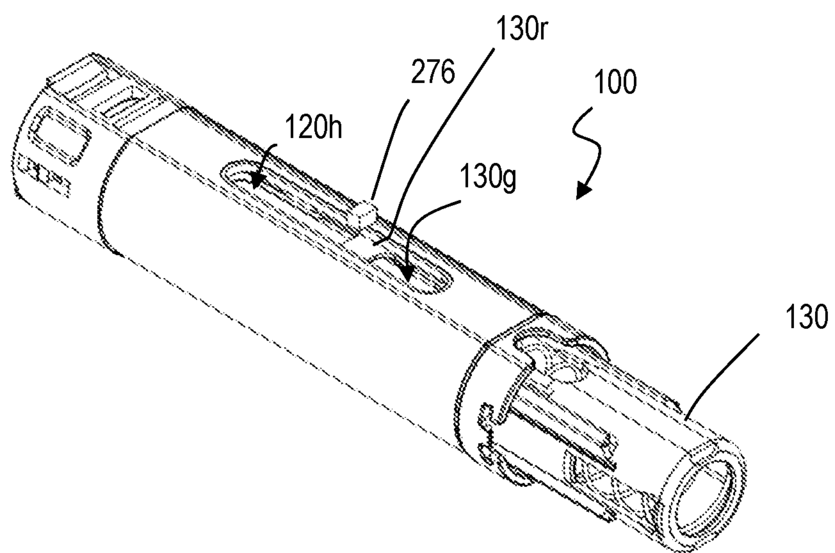
FIG. 26B is a perspective view illustrating the needle guard detector.

FIG. 26A and FIG. 26B are perspective views illustrating the needle guard detector 276. The needle guard detector 276 is, for example, a reflective photosensor that includes a light-emitting element and a light-receiving element, and detects the state of the needle guard 130 protruding (ejected) to protect the injection needle 12. The light-emitting element irradiates light onto a part of the needle guard 130, and the light-receiving element detects light emitted from the light-emitting element and reflected by the needle guard 130 or light transmitted through the needle guard 130. For example, as shown in FIG. 6, when detecting the reflective portion 130r located at the rear end of the needle guard 130, the needle guard detector 276 is arranged at a position close to the window 120h of the cassette outer sheath 120 of the drug cartridge 100 loaded in the drug injection device 200. The needle guard detector 276 may be located in the upper casing 280A or may be arranged on the flexible board 282 on which the antenna of the RF-ID reader/writer 263 is provided.

As shown in FIG. 26A, when the needle guard 130 is in the first engagement position, the needle guard detector 276 is located over the opening 130g of the needle guard 130. For this reason, the needle guard detector 276 does not detect ejection of the needle guard 130. As shown in FIG. 26B, when the needle guard 130 is ejected and in the second engagement position, the needle guard detector 276 is located over the reflective portion 130r of the needle guard 130. Thus, for example, the output signal of the needle guard detector 276 becomes larger and detects the ejection of the needle guard 130.

<Cap Detector 275, Cartridge Removal Detector 273>

The cap detector 275 and the cartridge removal detector 273 are, for example, microswitches. As shown in FIG. 13, the cap detector 275 and the cartridge removal detector 273 are close to cartridge space 280a of the casing 280 and are positioned so that the switches are depressed being in contact with the cap 110 and the cassette outer sheath 120 of the drug cartridge 100, respectively, when the drug cartridge 100 is loaded. The cartridge removal detector 273 outputs a detection signal (ON) while the drug cartridge 100 is loaded in the drug injection device 200, and the cap detector 275 outputs a detection signal (ON) while the cap 110 is attached to the drug cartridge 100. When the cap 110 is removed, the cap detector 275 turns OFF, and when the drug cartridge 100 is ejected, the cartridge removal detector 273 turns OFF.

<Skin Contact Detector 274>

As shown in FIG. 13, the skin contact detector 274 is arranged in the touch sensor unit 287. The skin contact detector 274 is a touch sensor, a capacitance sensor, or the like, and detects skin contact. The detection surface of the skin contact detector 274 is in contact with the skin contact surface 201*b* from the inside or the detection surface constitutes the skin contact surface 201*b*. The skin contact detector 274 is ON while the skin contact surface 201*b* is in contact with the skin.

(Operation of Drug Injection System 300)

Hereinafter, with reference to FIG. 14 and FIG. 27 to FIG. 39, an example of a method of controlling the drug injection device 200, the operation of the drug injection system 300 including the drug cartridge 100 and the drug injection device 200, the procedure for use, and the method of operation will be described. FIG. 27 to FIG. 39 are flow charts showing the control of the drug injection device 200 and the operation of the drug injection system 300.

The drug injection device 200 and the control circuit 251 can operate in the standby mode and the operating mode, and the control circuit 251 can switch between the standby mode and the operating mode. In the standby mode, only the output of the cartridge removal detector 273, for example, can be detected by the control circuit 251, and other detectors and other configurations are inoperative or in a power-saving standby mode.

Figure 27:
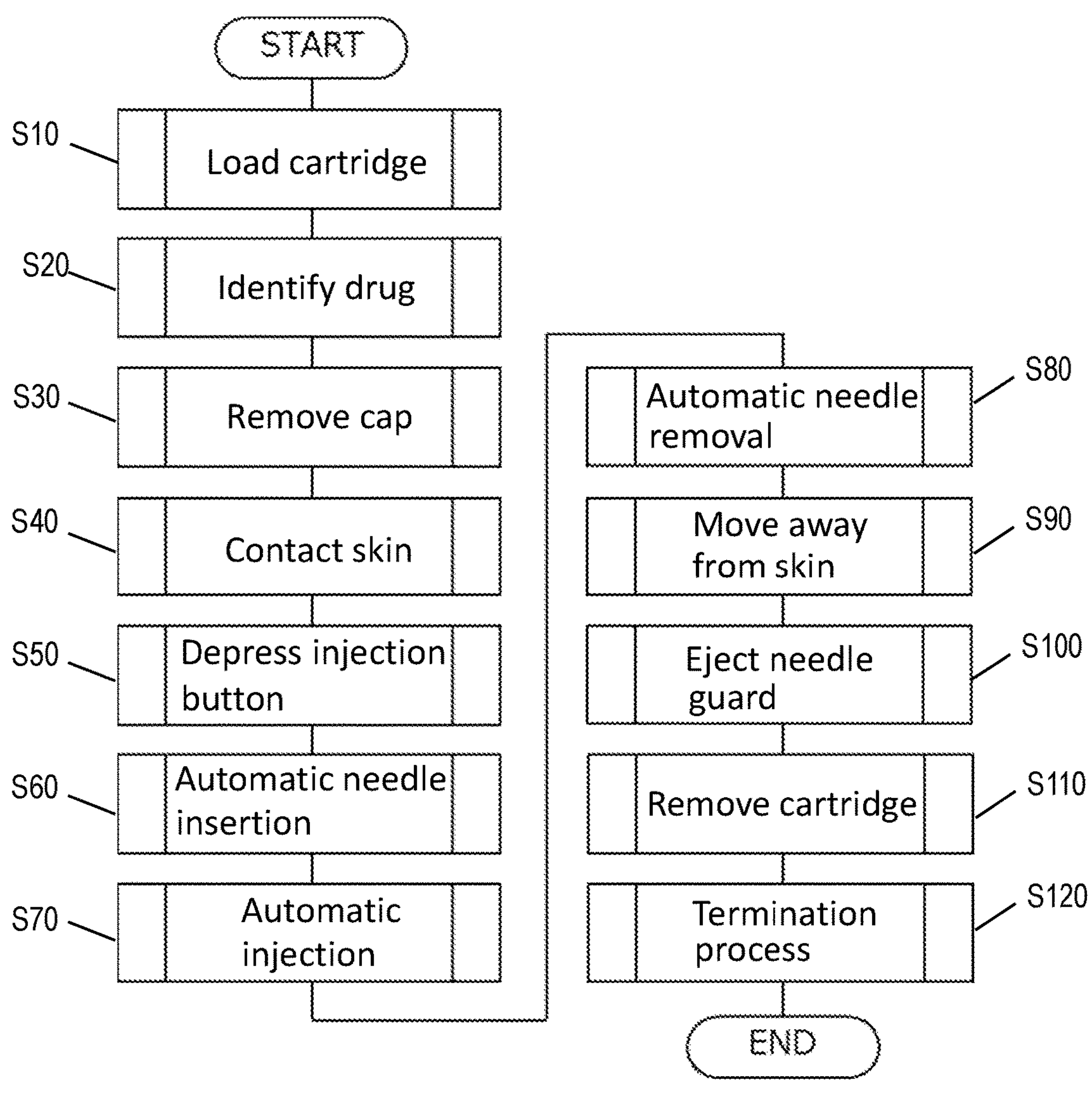
FIG. 27 is a flow chart illustrating an operation of the drug injection system.

<Main Flow Operation, FIG. 27>

The operator loads the drug cartridge 100 into the drug injection device 200 (S10). The drug injection device 200 identifies the loaded drug cartridge 100 (S20). The operator removes the cap 110 of the drug cartridge 100 (S30) and places the drug injection device 200 in contact with the skin (S40). The operator presses the injection button 254 (S50), and the needle is automatically inserted (S60). Further, the drug is injected (S70). After the drug injection is completed, the needle is automatically removed (S80). When the operator removes the drug injection device 200 from the injection site (S90), the needle guard 130 is ejected (S100). Then, when the operator removes the drug cartridge 100 (S110), the termination process is performed (S120). The subflows will be described in detail below.

Figure 28:
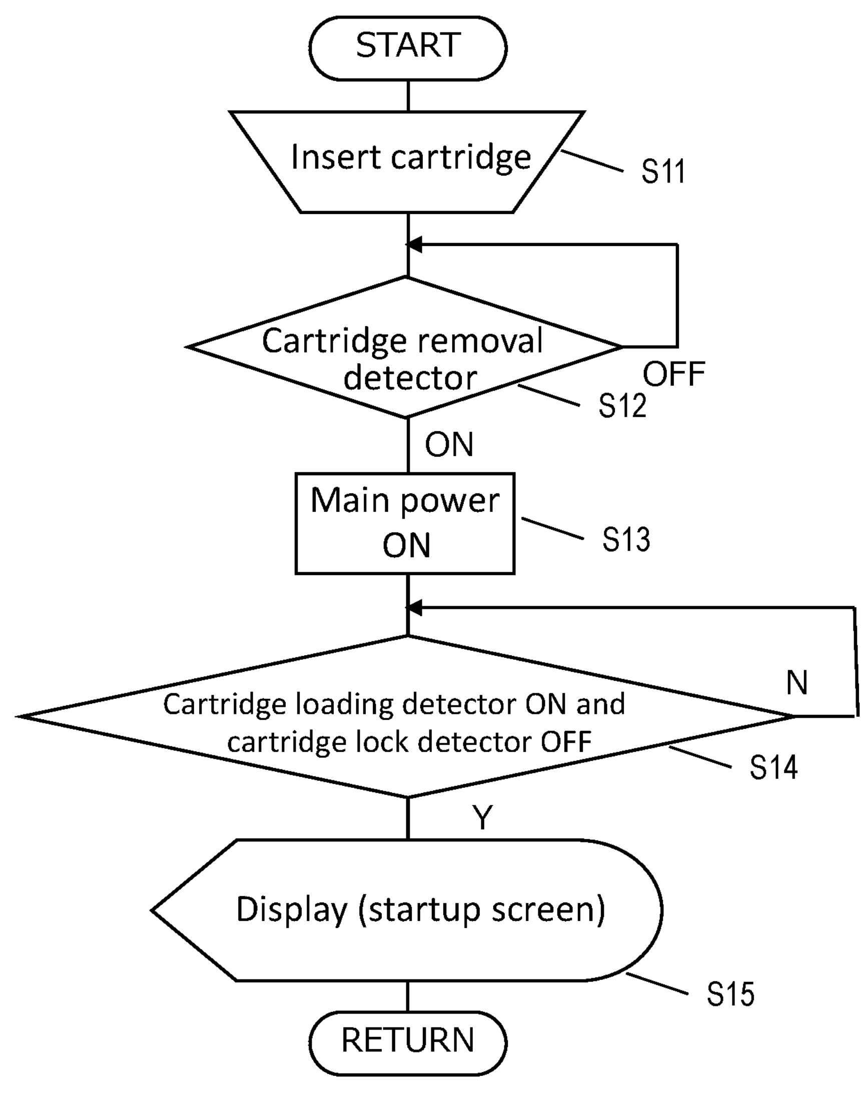
FIG. 28 is a flow chart illustrating an operation of the drug injection system.

<Cartridge Insertion Flow, FIG. 28>

The drug injection device 200 is operating in the standby mode. When the drug cartridge 100 is loaded into the drug injection device 200 while operating in the standby mode, the control circuit 251 switches from the standby mode to the operating mode based on the output (ON) of the cartridge removal detector 273. Specifically, the operator inserts the drug cartridge 100 through the cartridge opening 201*a* of the drug injection device 200 (S11). Based on the detection signal of the cartridge removal detector 273 (S12), the control circuit 251 switches from the standby mode to the operating mode, i.e., turns ON the main power (S13). The control circuit 251 remains in the standby mode until the cartridge removal detector 273 detects the loading of the drug cartridge 100. After the main power is turned ON, the control circuit 251 detects that the cartridge loading detector 271 is turned ON and the cartridge lock detector 272 is turned OFF (S14) in the order shown in Table 2 to detect that the drug cartridge 100 is correctly loaded. Note that as shown in Table 2, it can be confirmed that the drug cartridge 100 has been correctly loaded into the drug injection device 200 if only the cartridge loading detector 271 is ON and the cartridge lock detector 272 is OFF, so the main power may be turned ON to switch from the standby mode to the operating mode at the timing when the cartridge loading detector 271 or the cartridge lock detector 272 is turned ON. Then, the control circuit 251 displays the startup screen on the display device 258 (S15), and the process returns to the main flow.

Figure 29:
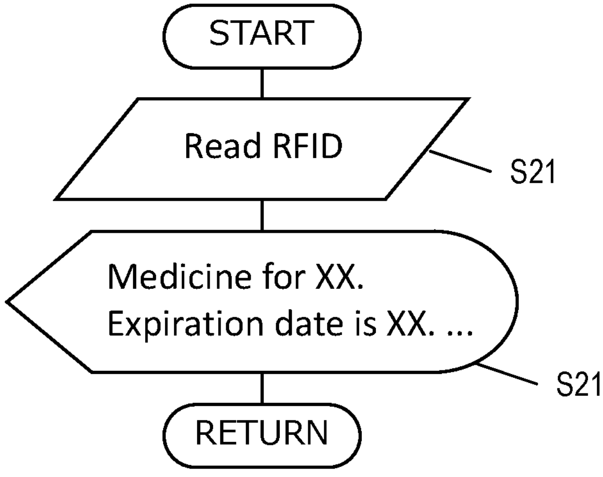
FIG. 29 is a flow chart illustrating an operation of the drug injection system.

<Drug Identification Flow, FIG. 29>

The control circuit 251 reads the information regarding the drug stored in the radio tag 190 of the drug cartridge 100 using the RF-ID reader/writer 263 (S21). Further, the control circuit 251 displays the read information on the display device 258 (S22). For example, the control circuit 251 displays text information such as "Medicine for XX. Expiration date is XX". Although not shown in FIG. 29, if the expiration date has passed, a used flag has been written, or the type of drug is not compatible with the drug injection device 200, the controller device 251 may display, on the display device 258, information informing the operator that the inserted drug cartridge cannot be used, and proceed to the cartridge removal flow (S11).

Figure 30:
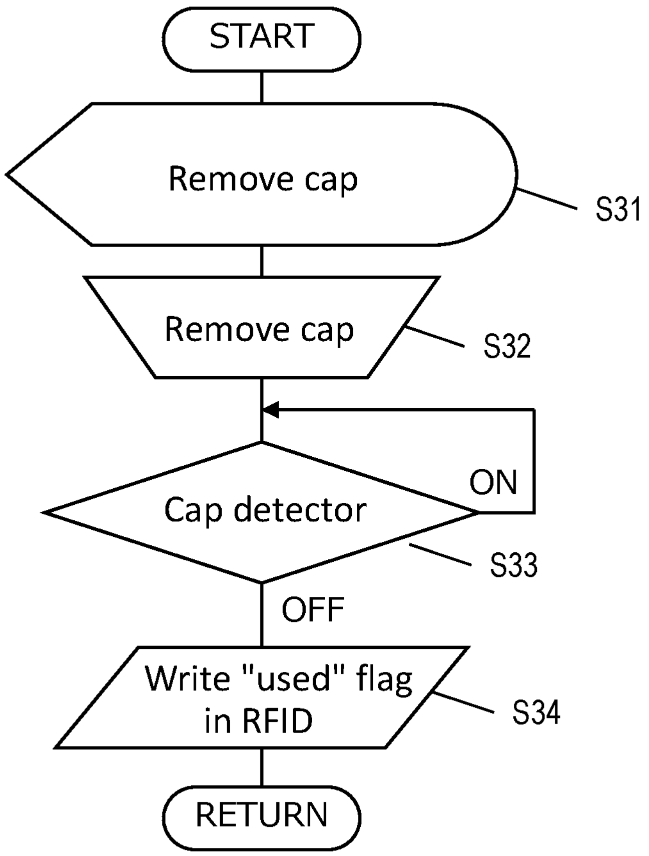
FIG. 30 is a flow chart illustrating an operation of the drug injection system.

<Cap 110 Removal Flow, FIG. 30>

The control circuit 251 causes the display device 258 to display a prompt for the operator to remove the cap 110 (S31). For example, the display device 258 is made to display text information such as "Remove cap". A graphic or animated display may be provided. The operator removes the cap 110 (S32). The control circuit 251 detects that the cap detector 275 is turned off (S33) and uses the RF-ID reader/writer 263 to write a flag to the radio tag 190 of the drug cartridge 100 indicating that it has been used. Thus, it is possible to identify a drug cartridge 100 that has been ejected after discontinuation of injection after the cap 110 is removed, and it is possible to avoid the use of the drug cartridge 100 that cannot be guaranteed to be clean due to the removal of the cap 110.

Figure 31:
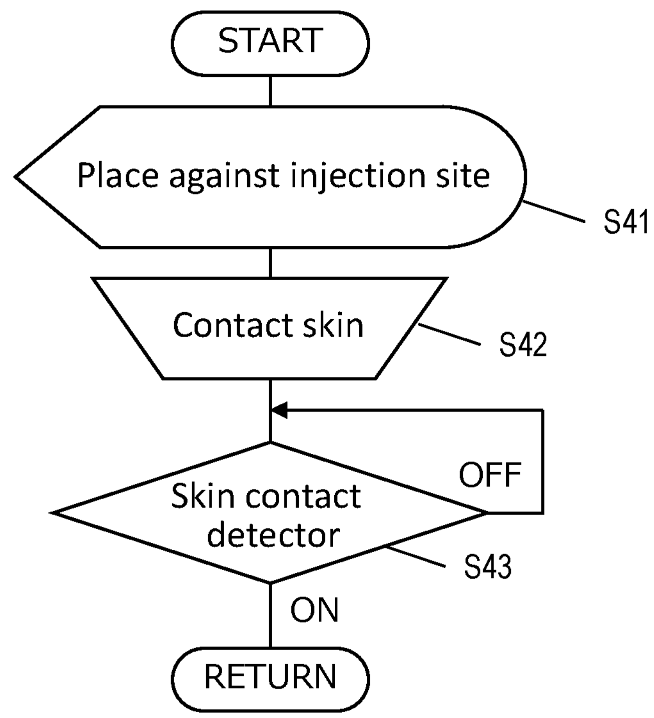
FIG. 31 is a flow chart illustrating an operation of the drug injection system.

<Skin Contact Flow, FIG. 31>

The control circuit 251 causes the display 258 to display information prompting the operator to press the drug injection device 200 against the injection site (S41). For example, the display device 258 is made to display a message such as "Press against injection site". The operator follows the display and presses the entire drug injection device 200 against the injection site (S42). The control circuit 251 determines whether the skin contact detector 274 has detected skin contact (S43). If detected, the control circuit 251 terminates this flow. If the skin contact detector 274 has not detected skin contact, this step is repeated.

Figure 32:
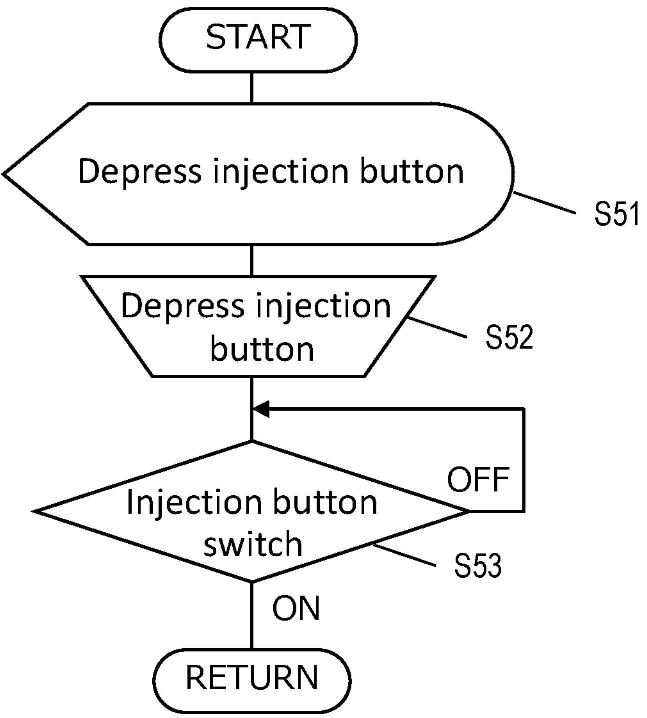
FIG. 32 is a flow chart illustrating an operation of the drug injection system.

<Injection Button Depressing Flow, FIG. 32>

The control circuit 251 causes the display device 258 to display information prompting the operator to depress the injection button 254 (S51). For example, the display device 258 is made to display a message such as "Press injection button". The operator follows the display and depresses the injection button 254 (S52). The control circuit 251 determines whether the injection button 254 has been depressed (S53). If the depression of the injection button 254 is detected, this flow is terminated. If the depression of the injection button 254 is not detected, this step is repeated.

Figure 33:
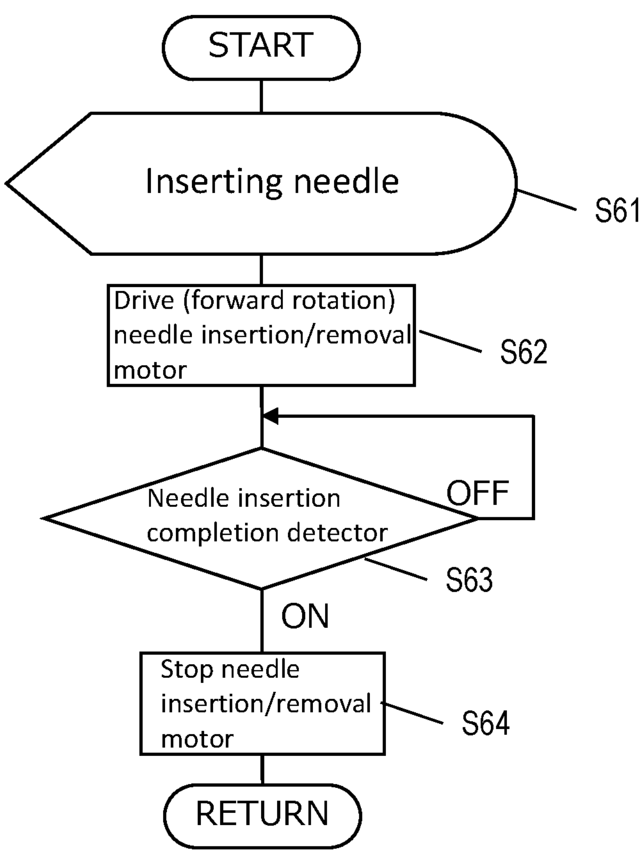
FIG. 33 is a flow chart illustrating an operation of the drug injection system.

<Automatic Needle Insertion Flow, FIG. 33>

The control circuit 251 causes the display device 258 to display information that alerts the operator that needle insertion is to be performed (S61). For example, the control circuit 251 causes the display device 258 to display a message such as "Inserting needle". Thereafter, the needle insertion/removal motor 268 is rotated forward (S62) to cause the piston unit 286 to move forward. When the needle insertion completion detector 277 detects that the piston unit 286 has moved to the needle insertion position (S63), the control circuit 251 stops the needle insertion/removal motor 268 (S64). This step is repeated until detection by the needle insertion completion detector 277.

Figure 34:
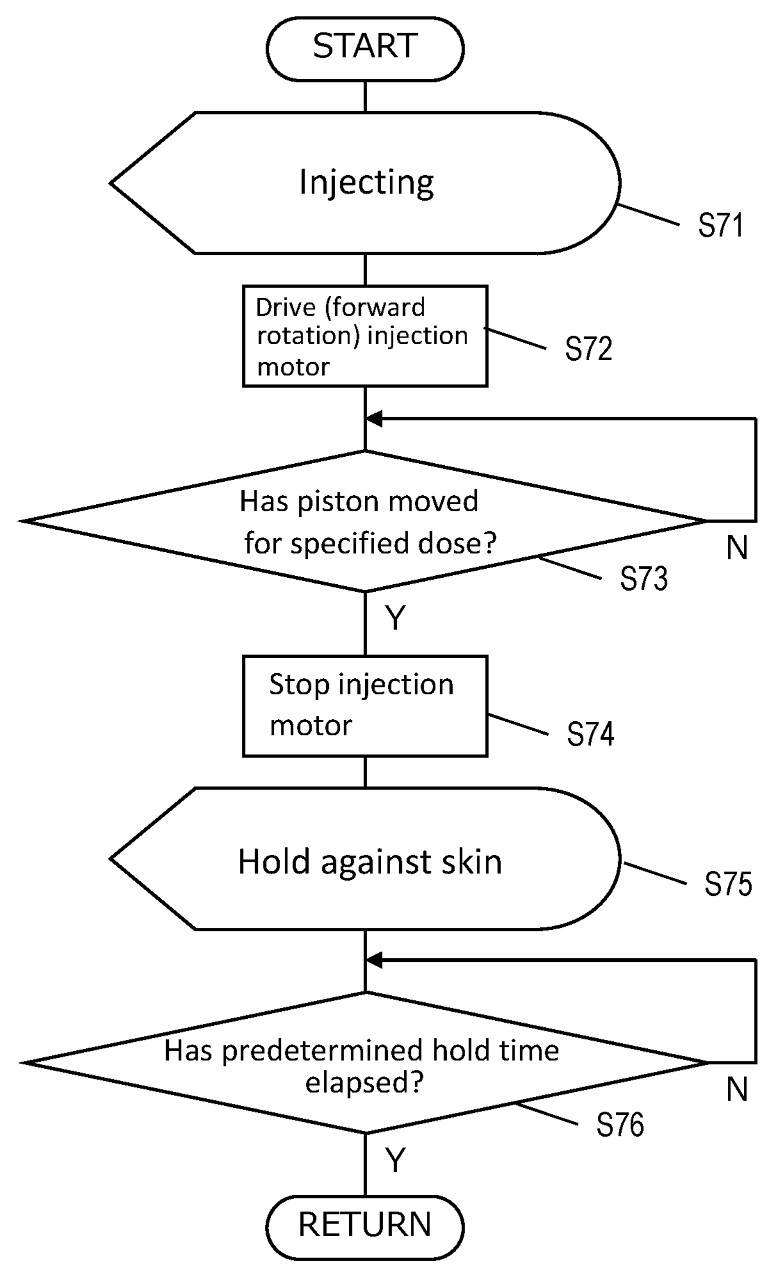
FIG. 34 is a flow chart illustrating an operation of the drug injection system.

<Automatic Injection Flow, FIG. 34>

The control circuit 251 causes the display device 258 to display information that alerts the operator that injection is to be performed (S71). For example, the control circuit 251 causes the display device 258 to display a message such as "Injecting". Thereafter, the injection motor 265 is rotated forward (S72) and the piston 221 is moved forward from the initial position, thereby moving the stopper 13 of the pre-filled syringe 10 to inject the drug. The control circuit 251 determines whether the piston 221 has moved forward over a distance for a specified dose (S73). For this determination, for example, the detection signal of the rotary encoder 266 can be used. Alternatively, where the entire amount of the drug filled in the pre-filled syringe 10 is administered, the control circuit 251 may detect the change in motor current caused by an increase of the load of the injection motor 265 after the stopper 13 (FIG. 2) of the pre-filled syringe 10 reaching the front end of the syringe columnar space 11*s*.

If the control circuit 251 determines that the piston has moved forward for a specified dose, the control circuit 251 stops the injection motor 265 (S74). The control circuit 251 causes the display 258 to display information prompting the operator not to remove the drug injection device 200 immediately (S75). For example, the control circuit 251 causes the display device 258 to display a message such as "Hold against skin". Then, the control circuit 251 determines, using the clock 260, whether or not a predetermined hold time has elapsed (S76). If the predetermined hold time has elapsed, this flow is terminated.

Figure 35:
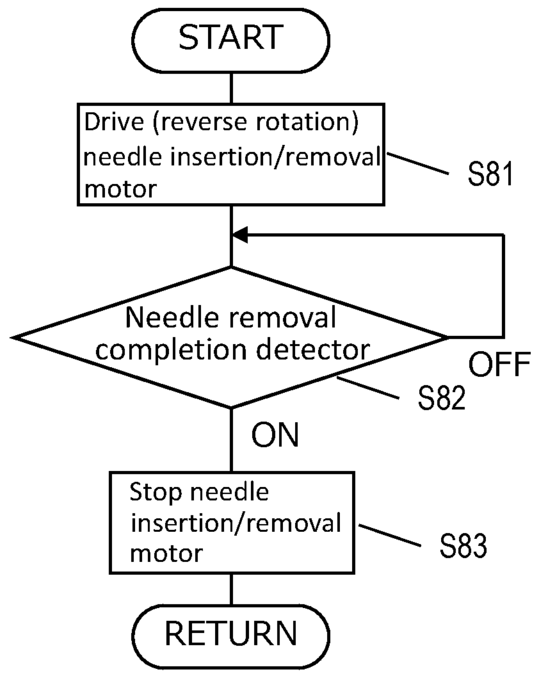
FIG. 35 is a flow chart illustrating an operation of the drug injection system.

<Automatic Needle Removal Flow, FIG. 35>

The control circuit 251 reverses the needle insertion/removal motor 268 (S81) to cause the piston unit 286 and the drug cartridge 100 gripped thereby to move backward. Moreover, it is determined whether the needle removal completion detector 278 detects that the piston unit 286 has moved to the needle removal position (S82). If detected, the control circuit 251 stops the needle insertion/removal motor 268 (S83) and terminates this flow.

Figure 36:
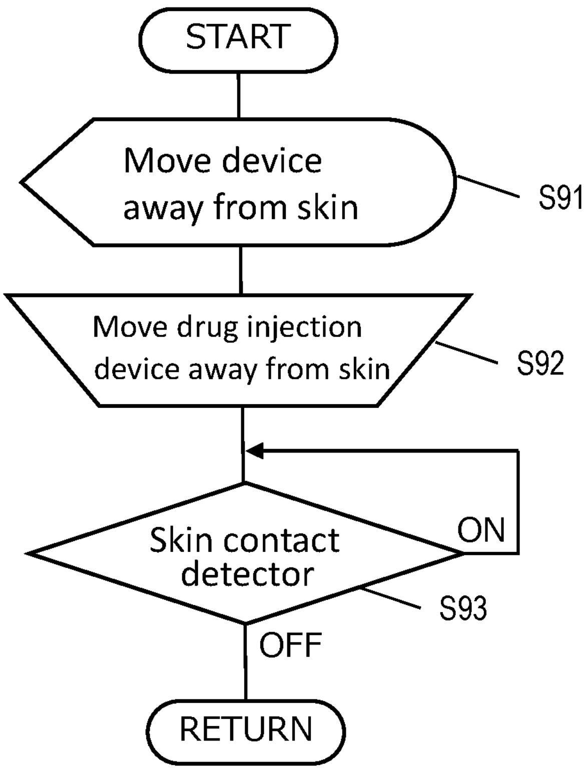
FIG. 36 is a flow chart illustrating an operation of the drug injection system.

<Move Away from Skin Flow, FIG. 36>

The control circuit 251 causes the display device 258 to display information prompting the operator to move the drug injection device 200 away from the skin (S91). For example, the control circuit 251 causes the display device 258 to display a message such as "Move device away from skin". When the operator moves the drug injection device 200 away from the skin (S92), the control circuit 251 determines whether the skin contact detector 274 has detected the separation from the skin (S93). If detected, this flow is terminated.

Figure 37:
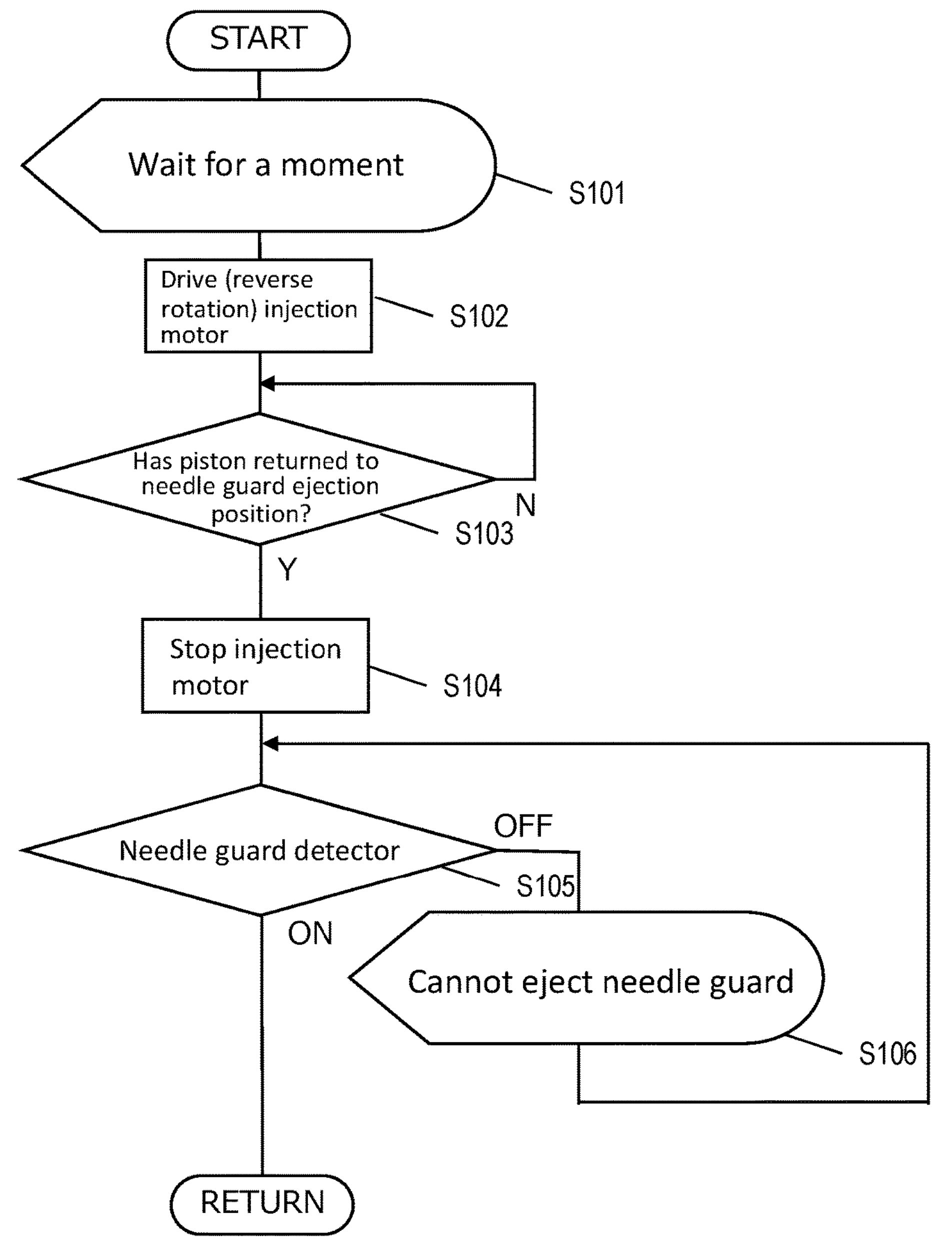
FIG. 37 is a flow chart illustrating an operation of the drug injection system.

<Needle Guard Eject Flow, FIG. 37>

The control circuit 251 causes the display device 258 to display information prompting the operator to wait for a while (S101). For example, the control circuit 251 causes the display device 258 to display a message such as "Wait for a moment". Then, the injection motor 265 is reversed (S102), and the piston is moved backward to the needle guard discharge position, which is further backward than the initial position.

As illustrated in Table 1 and in "(4) State where needle guard is ejected (FIG. 9D, FIG. 10D)" in the description of the drug cartridge 100 above, as the piston 221 moves backward, the latch unit 230 rotates around the piston axis 221*j*, and the contact between the sleeve contact portion 233*g* and the sleeve 150 is disengaged. The sleeve 150 moves from the second position to the first position by the biasing force of the cassette spring 140. This causes the needle guard 130 to be unlocked. The needle guard 130 moves from the first engagement position to the second engagement position by the biasing force of the cassette spring 140.

The control circuit 251 determines from the output of the rotary encoder whether the piston 221 has moved backward to the needle guard ejection position (S103). Specifically, the control circuit 251 determines whether the piston 221 has moved backward to the needle guard ejection position where the contact between the sleeve 150 of the drug cartridge 100 and the latch unit 230 is disengaged as described above. If the control circuit 251 detects that the piston 221 has moved backward to the needle guard discharge position, the control circuit 251 stops the injection motor 265 (S104). When the contact between the sleeve 150 of the drug cartridge 100 and the latch unit 230 is disengaged, the sleeve 150 of the drug cartridge 100 moves to the first position and the needle guard 130 is unlocked in the first engagement position, causing the needle guard 130 to move from the first engagement position to the second engagement position. That is, the needle guard 130 is ejected.

Then, the control circuit 251 determines whether the needle guard detector 276 has detected the ejection of the needle guard 130 (S105). If detected, this flow is terminated. If the ejection of the needle guard 130 cannot be detected, the display device 258 displays a message indicating that the needle guard has not been ejected (S106) to wait until ejection is detected. If the ejection of the needle guard 130 is not detected even after a certain period of time, the control circuit 251 may perform a process of abnormal termination by terminating this flow and discontinuing the processing of the main flow (FIG. 27). For example, the control circuit 251 causes the display device 258 to display a message indicating that an abnormality has occurred in the drug injection device 200 and prompting the operator to contact their treating physician, or other person.

Figure 38:
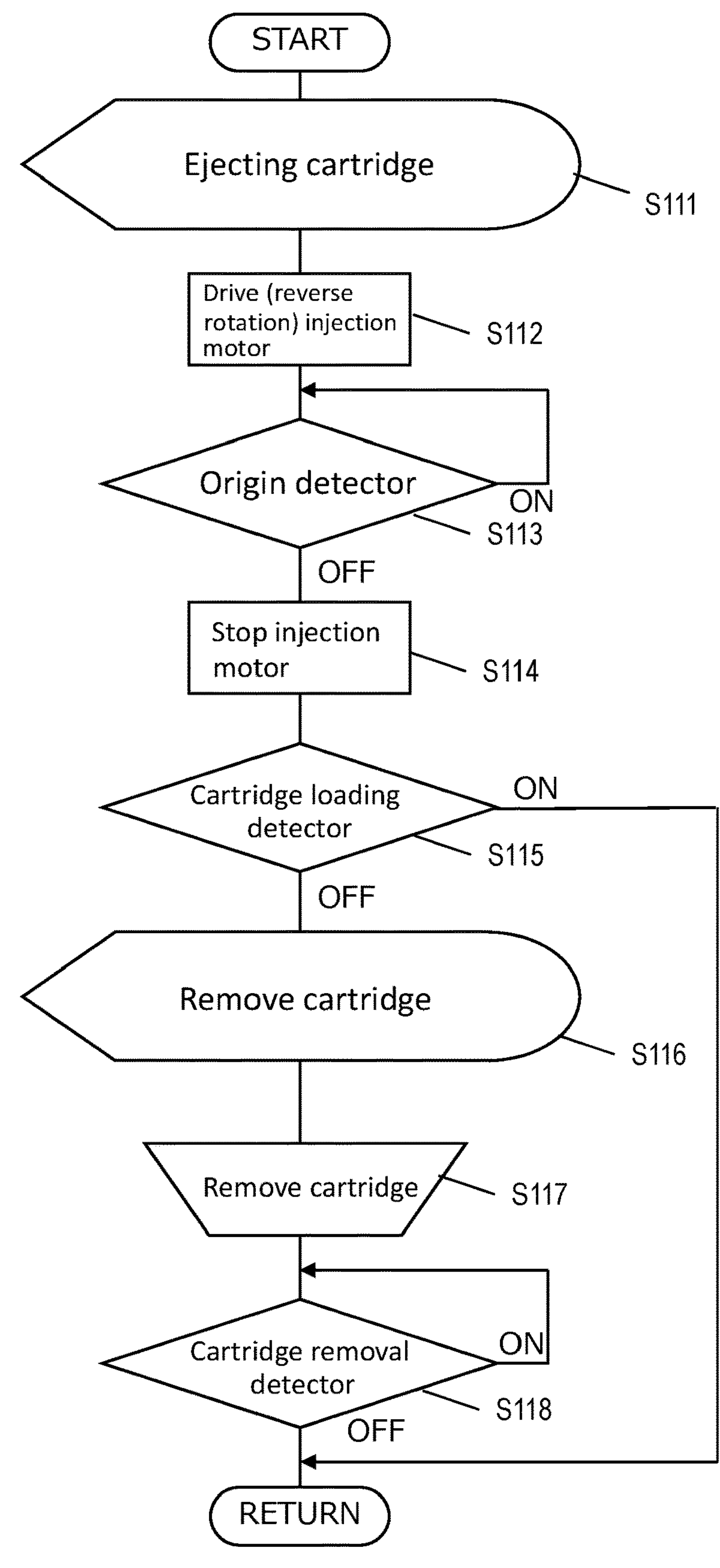
FIG. 38 is a flow chart illustrating an operation of the drug injection system.

<Cartridge Removal Flow, FIG. 38>

The control circuit 251 causes the display device 258 to display information that alerts the operator that an operation of removing the drug cartridge 100 is to be performed (S111). For example, the control circuit 251 causes the display device 258 to display a message such as "Ejecting cartridge". Then, the control circuit 251 reverses the injection motor 265 (S112). This causes the piston 221 to move backward to the cartridge ejection position, which is further backward from the needle guard ejection position. As the piston moves backward, the latch unit 230 rotates further around the piston axis 221*j*, disengaging the engagement between the cartridge latch 235 and the cassette outer sheath 120. This releases the drug cartridge 100 from the piston unit 286 and allows the drug cartridge 100 to be removed.

The control circuit 251 determines whether the origin detector 279 is in contact with the piston 221, i.e., whether the piston 221 has moved backward to the origin position (S113). If the origin detector 279 detects contact with the piston 221, the control circuit 251 stops the injection motor 265 (S114).

The control circuit 251 further determines whether the cartridge loading detector 271 detects the loading of the drug cartridge 100 (S115). If loading of the drug cartridge 100 is not detected, i.e., the drug cartridge 100 has been released from the piston unit 286, the control circuit 251 causes the display 258 to display information prompting the operator to remove the cartridge (S116). For example, the control circuit 251 causes the display device 258 to display a message such as "Remove cartridge".

When the operator removes the drug cartridge (S117), the control circuit 251 determines whether the cartridge removal detector 273 detects contact with the drug cartridge 100 (S118). If not detected, the drug cartridge 100 has been removed and this flow is terminated.

If the cartridge loading detector 271 is detecting the loading of the drug cartridge 100 (S115), the piston unit 286 remains gripping on the drug cartridge 100 for some reason, and the drug cartridge 100 cannot be removed. In this case, the control circuit 251 terminates this flow, discontinues the processing of the main flow (FIG. 27), and performs the abnormal termination process described above.

Figure 39:
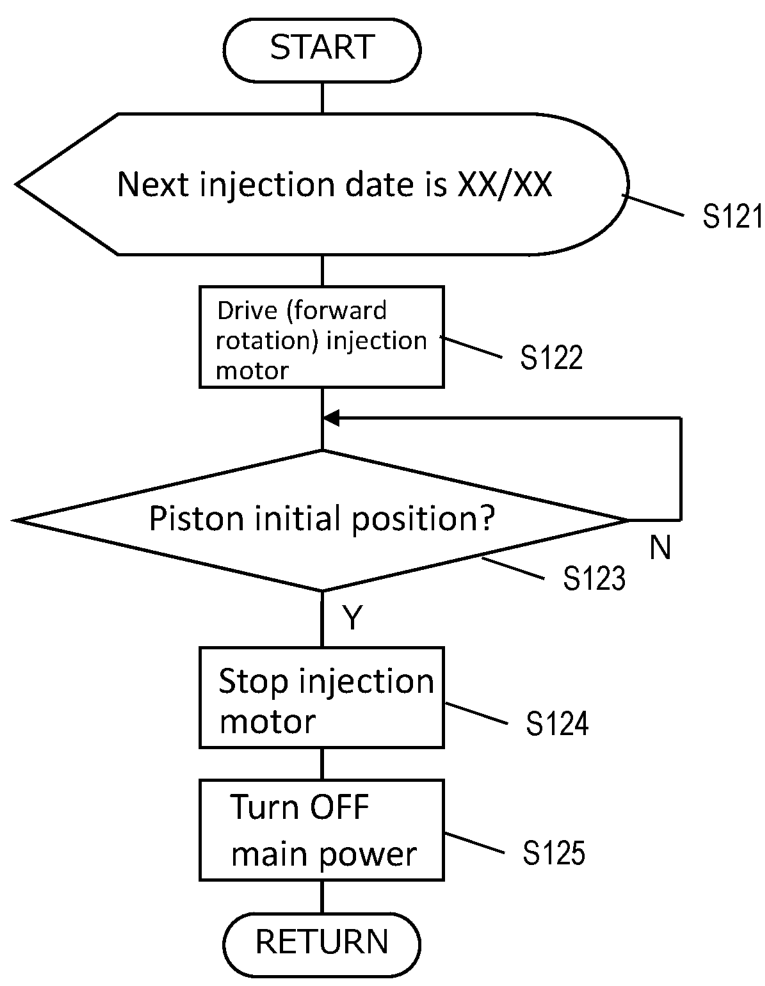
FIG. 39 is a flow chart illustrating an operation of the drug injection system.

<Termination Process Flow, FIG. 39>

The control circuit 251 causes the display device 258 to display that alerts the operator of the next injection schedule (S121). For example, the control circuit 251 causes the display device 258 to display a message such as "Next injection date is XX/XX". The control circuit 251 also causes the injection motor 265 to rotate forward (S122).

The control circuit 251 determines whether the piston 221 has moved forward to the initial position based on the output of the rotary encoder 266 based on the position of the piston 221 that has been stopped based on the detection of the origin detector 279 in the cartridge removal flow (S123). When the output of the rotary encoder 266 reaches a predetermined value, the control circuit 251 stops the injection motor 265 (S124). Then, the main power is turned OFF and the control switches from the operating mode to the standby mode (S125).

According to the operation of the drug injection system 300 of the present embodiment, the various detectors detect various states during the injection operation to alert the operator of the next operation according to the detection results. Therefore, the operator can perform the operation of injecting the drug easily and with peace of mind without having anxiety about whether the operation procedure is correct or not. After removing the cap 110 of the drug cartridge 100, the injection needle 12 is covered by the needle guard 130 and is not exposed during a series of operations of injecting the drug, removing the drug cartridge 100 from the drug injection device 200 and disposing the drug cartridge 100. Thus, the operator can use the drug injection system 300 with peace of mind, without having to take special precautions against pricking their fingers with the injection needle 12 or catching clothing with the exposed injection needle 12.

(Other Embodiments)

The structure of the drug cartridge 100 and the drug injection device 200 described in the embodiment above is an example, and various modifications are possible.

In particular, the shapes and positions of the various engagement portions and engagement claws are not limited to the examples illustrated in the figures and can be modified in various ways. The positions and detection methods of the various detectors are also not limited to the embodiment described above, but can be modified in various ways. The spring described as an example of the biasing member may be any of various springs such as coil springs, pull springs, plate springs, torsion springs, etc. In addition to metal springs, various springs made of resin may also be used. Elastic members composed of plate springs and resin are also not limited to the examples listed in the embodiment, and various elastic materials can be used.

The information displayed on the display device as described in the embodiment above is only one example, and other contents may be displayed, or the operator may be alerted by sounding a buzzer instead of or in conjunction with the display on the display device.

Although the drug cartridge 100 includes the pre-filled syringe 10, a drug cartridge without the pre-filled syringe 10 may be provided as a training drug cartridge. Such a training drug cartridge operates in the same manner as the drug cartridge 100, except that by not including the pre-filled syringe 10, the needle cannot actually be inserted/removed and the drug is not administered. Therefore, an operator new to handling the drug injection device 200 can use such a training drug cartridge for training to become familiar with its handling.

INDUSTRIAL APPLICABILITY

The drug cartridge, the drug injection device and the drug injection system of the present disclosure are suitably used in various drug injecting devices.

REFERENCE SIGNS LIST

10: Pre-filled syringe, 11: Syringe barrel, 12: Injection needle, 13: Stopper, 14: Needle shield, 100: Drug cartridge, 110: Cap, 120: Cassette outer sheath, 120*a*: Cassette front opening, 120*b*: Cassette rear opening, 120*c*: Cassette columnar space, 130; Needle guard, 130*c*: Guard portion, 140: Cassette spring, 150: Sleeve, 200: Drug injection device, 201: Outer case, 251: Control circuit, 265: Injection motor, 268: Needle insertion/removal motor, 283: Interface, 286: Piston unit, 300: Drug injection system

The invention claimed is:

1. A drug cartridge comprising:

a pre-filled syringe including a drug, a syringe barrel having a syringe columnar space in which the drug is arranged and a syringe opening located at one end of the syringe columnar space, an injection needle located on an opposite side of the syringe barrel from the syringe opening and being in communication with the syringe columnar space, a stopper movable in the syringe columnar space and arranged on the syringe opening side, and a needle shield that covers a tip of the injection needle and is removable;

a cassette outer sheath including a cassette front opening, a cassette rear opening and a cassette columnar space located between the cassette rear opening and the cassette front opening, wherein the cassette outer sheath holds the pre-filled syringe in the cassette columnar space so that a part of the injection needle and a part of the needle shield protrude from the cassette front opening;

a cap mated with the needle shield and fitted into the cassette front opening so as to cover the needle shield, wherein the cap is removable from the cassette outer sheath together with the needle shield;

a needle guard including a guard portion and movable in an axis direction of the cassette columnar space in the cassette columnar space, wherein the needle guard is movable between a first engagement position and a second engagement position, wherein in the first engagement position, a front end of the guard portion is further backward than the tip of the injection needle protruding from the cassette front opening, and in the second engagement position, the front end of the guard portion protrudes from the tip of the injection needle protruding from the cassette front opening where the cap is detached;

a sleeve movable in the axis direction in the cassette columnar space between a first position located on the cassette rear opening side and a second position located on the cassette front opening side relative to the first position, wherein the sleeve is engaged with the cassette outer sheath in the first position; and a cassette spring that biases the needle guard toward the cassette front opening, wherein when the cap is fitted into the cassette front opening, the cap is capable of assuming a locked state where the cap cannot be detached from the cassette outer sheath and an unlocked state where the cap can be detached from the cassette outer sheath, and the needle guard is in contact with the cap and is located in the first engagement position against a biasing force of the cassette spring, where the cap is fitted into the cassette front opening and the sleeve is in the first position, the cap is locked; and, where the cap is fitted into the cassette front opening and the sleeve is in the second position, the sleeve renders the cap in an unlocked state and the needle guard in a locked state in which the needle guard is unmovable in the first engagement position.

2. The drug cartridge according to claim 1, wherein:

one end of the cassette spring is in contact with the needle guard and the other end of the cassette spring is in contact with the sleeve; and where the cap is fitted into the cassette front opening, the sleeve moves from the first position to the second position by an external force against the biasing force of the cassette spring, thereby removing the cap.

3. The drug cartridge according to claim 2, wherein:

after the cap is removed, the external force is removed so that the sleeve moves from the second position to the first position by the biasing force of the cassette spring; and as the sleeve unlocks the needle guard, the needle guard moves from the first engagement position to the second engagement position by the biasing force of the cassette spring.

4. The drug cartridge according to claim 3, wherein in the second engagement position, the needle guard is engaged with the cassette outer sheath so that the needle guard is unmovable toward the first engagement position.

5. The drug cartridge according to claim 1, wherein:

the syringe barrel includes a flange arranged in the vicinity of the syringe opening;

the cassette outer sheath includes a slit located in the vicinity of the cassette rear opening; and as the flange of the syringe barrel is inserted into the slit of the cassette outer sheath, the pre-filled syringe is held in the cassette outer sheath.

6. The drug cartridge according to claim 1, wherein:

the cap includes a cap main body and a cap spring that mates with the needle shield, wherein the cap main body includes a cylindrical trunk portion, a first elastic support portion one end of which is located at one end of the trunk portion, and a first engagement claw located at the other end of the first elastic support portion and including a contact surface at a tip thereof, wherein the cap spring is arranged in the trunk portion;

the cassette outer sheath includes a cap engagement portion located on an inner surface on a side of the cassette front opening; and where the cap is fitted into the cassette front opening, the cap main body surrounds the cassette front opening, the first engagement claw is inserted into the cassette outer sheath through the cassette front opening, and the cap is engaged with the cap engagement portion so that the cap is undetachable from the cassette front opening.

7. The drug cartridge according to claim 6, wherein:

the guard portion of the needle guard includes an end face portion and a needle guard opening provided at the end face portion, and has a cylindrical shape that defines a needle guard columnar space capable of housing a part of the syringe barrel of the pre-filled syringe;

the needle guard further includes a second elastic support portion one end of which is connected to one end of the guard portion opposite from the needle guard opening, and a protrusion provided at the other end of the second elastic support portion;

the cassette outer sheath includes a first opening located on the cassette rear opening side, and a second opening located on the cassette front opening side relative to the first opening;

where the needle guard is in the first engagement position, the protrusion is engaged with the first opening; and where the needle guard is in the second engagement position, the protrusion is engaged with the second opening.

8. The drug cartridge according to claim 7, wherein:

the protrusion includes a slope portion located on the guard portion side and sloped on the cassette outer sheath side, a recess provided in the slope portion, an apex portion adjacent to the slope portion, a side portion adjacent to the apex portion on an opposite side from the slope portion, and an inner surface portion located on an inner side relative to the slope portion, the apex portion and the side portion;

the cassette outer sheath includes an in-opening protrusion protruding from an edge of the second opening on the cassette front opening side toward a center of the second opening; and where the protrusion is engaged with the second opening, the slope portion of the protrusion is in contact with an edge of the second opening on the cassette front opening side, and the in-opening protrusion is engaged with the recess of the slope portion.

9. The drug cartridge according to claim 8, wherein:

the sleeve includes an inner cylinder portion including a sleeve front opening and a space that houses a part of the pre-filled syringe, an outer cylinder portion arranged separated outward relative to the inner cylinder portion and including a sleeve rear opening, a sleeve contact surface located on the sleeve front opening side of the outer cylinder portion, and a slit provided in each of the inner cylinder portion and the outer cylinder portion; and in the cassette columnar space of the cassette outer sheath, the sleeve contact surface is located on the cassette front opening side, at least the protrusion and the second elastic support portion of the needle guard are located between the inner cylinder portion and the outer cylinder portion, and the slit of the inner cylinder portion and the slit of the outer cylinder portion are aligned in the radial direction with the second elastic support portion and the protrusion on a cross section perpendicular to an axis of the cassette columnar space.

10. The drug cartridge according to claim 9, wherein:

where the cap is fitted into the cassette front opening and the sleeve is in the second position, the sleeve contact surface of the sleeve is in contact with a contact surface of the first engagement claw of the cap;

engagement between the first engagement claw and a cap engagement portion of the cassette outer sheath is disengaged by deformation of the first elastic support portion; and the inner cylinder portion of the sleeve and an inner surface of the protrusion of the needle guard are in contact with each other, thereby suppressing deformation of the second elastic support portion.

11. The drug cartridge according to claim 9, wherein:

where the cap is removed from the cassette front opening and the sleeve is in the first position, an edge of the first opening and the slope portion of the protrusion are in contact with each other by the biasing force of the cassette spring, and the second elastic support portion deforms inward into the slit of the inner cylinder portion, thereby causing the protrusion to detach inward from the first opening, and the needle guard to move from the first engagement position to the second engagement position; and in the second engagement position, the inner cylinder portion of the sleeve and the inner surface of the protrusion of the needle guard are in contact with each other, thereby suppressing deformation of the second elastic support portion.

12. The drug cartridge according to claim 11, wherein:

the sleeve includes a third elastic support portion one end of which is located in the vicinity of the sleeve rear opening, and a second engagement claw located at the other end of the third elastic support portion and including a contact surface at a tip thereof;

the cassette outer sheath includes a sleeve engagement portion located on an inner surface on the cassette rear opening side; and where the sleeve is in the first position, the second engagement claw of the sleeve and the sleeve engagement portion of the cassette outer sheath are engaged with each other, thereby suppressing the sleeve from moving to the second position.

13. A drug injection device comprising:

a case including a cartridge space in which the drug cartridge according to claim 1 can be loaded, and a cartridge opening in communication with the cartridge space;

a piston unit including a piston, a piston gear that drives the piston in a piston axis direction, and a latch unit for gripping the drug cartridge, wherein a part of the latch unit is inserted into the cassette rear opening of the drug cartridge;

a needle insertion/removal motor causing the piston unit to move forward and move backward in the piston axis direction;

an injection motor causing the piston to move forward and move backward in the piston axis direction;

a control circuit for controlling the needle insertion/removal motor and the injection motor; and an interface for inputting a command to the control circuit, wherein the latch unit includes a cartridge latch to engage with the cassette outer sheath of the drug cartridge, and a sleeve contact portion to be in contact with the sleeve of the drug cartridge;

when the drug cartridge is inserted into the cartridge space through the cartridge opening, the sleeve contact portion of the latch unit enters inside through the cassette rear opening to be in contact with the sleeve of the drug cartridge, thereby disengaging the engagement between the sleeve and the cassette outer sheath;

in response to the insertion of the drug cartridge, the sleeve contact portion moves the sleeve toward the second position relative to the cassette outer sheath, and the cartridge latch enters inside through the cassette rear opening; and at completion of loading of the drug cartridge, the sleeve reaches the second position, and the cartridge latch engages with the cassette outer sheath.

14. The drug injection device according to claim 13, wherein:

based on an input from the interface, the control circuit is configured to:

rotate the needle insertion/removal motor and cause the piston unit to move forward, thereby performing needle insertion;

rotate the injection motor and cause the piston to move forward from an initial position, thereby moving the stopper and injecting the drug; and after rotating the injection motor by a predetermined amount, reversing the needle insertion/removal motor and cause the piston unit to move backward, thereby performing needle removal.

15. The drug injection device according to claim 14, further comprising:

a needle guard detector that detects ejection of the needle guard, wherein:

after the needle removal, the control circuit reverses the injection motor to cause the piston to move backward to a needle guard ejection position, which is further backward than the initial position;

in response the piston moving backward, the latch unit rotates around the piston axis, thereby disengaging the contact between the sleeve contact portion and the sleeve;

as the sleeve moves from the second position to the first position by the biasing force of the cassette spring to unlock the needle guard, the needle guard moves from the first engagement position to the second engagement position by the biasing force of the cassette spring; and the needle guard detector detects ejection of the needle guard.

16. The drug injection device according to claim 15, wherein the needle guard detector includes a light-emitting element that irradiates light onto a part of the needle guard, and a light-receiving element that detects light emitted from the light-emitting element and reflected by the needle guard or transmitted through the needle guard.

17. The drug injection device according to claim 16, wherein:

the control circuit reverses the injection motor based on a detection signal of the needle guard detector to cause the piston to move backward to a cartridge ejection position, which is further backward than the needle guard ejection position; and in response to the piston moving backward, the latch unit rotates around the piston axis, thereby disengaging the engagement of the cartridge latch with the cassette outer sheath.

18. The drug injection device according to claim 15, wherein:

the piston includes a helical contact surface located on the tip side;

the latch unit includes a through hole into which the piston is inserted, and a restricting portion located on an inner surface of the through hole; and as the contact surface of the piston and the restricting portion of the latch unit come into contact with each other, the piston moves forward and backward, thereby rotating the latch unit around the piston axis.

19. The drug injection device according to claim 13, further comprising a door capable of opening and closing to cover the cartridge opening.

* * * * *